United States Patent
Miller et al.

(10) Patent No.: US 11,072,602 B2
(45) Date of Patent: Jul. 27, 2021

(54) ANTIDIABETIC HETEROCYCLIC COMPOUNDS

(71) Applicants: Merck Sharp & Dohme Corp., Rahway, NJ (US); Michael Miller, Scotch Plains, NJ (US); Harry R. Chobanian, Aberdeen, NJ (US); Shuwen He, Fanwood, NJ (US); Jinsong Hao, Belle Mead, NJ (US); Barbara Pio, West Orange, NJ (US)

(72) Inventors: Michael Miller, Scotch Plains, NJ (US); Harry R. Chobanian, Aberdeen, NJ (US); Shuwen He, Fanwood, NJ (US); Jinsong Hao, Belle Mead, NJ (US); Barbara Pio, West Orange, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/461,569

(22) PCT Filed: Dec. 1, 2017

(86) PCT No.: PCT/US2017/064106
§ 371 (c)(1),
(2) Date: May 16, 2019

(87) PCT Pub. No.: WO2018/106518
PCT Pub. Date: Jun. 14, 2018

(65) Prior Publication Data
US 2019/0367495 A1    Dec. 5, 2019

Related U.S. Application Data

(60) Provisional application No. 62/430,625, filed on Dec. 6, 2016.

(51) Int. Cl.
| | | |
|---|---|---|
| *C07D 405/14* | (2006.01) |
| *C07D 311/04* | (2006.01) |
| *C07D 405/06* | (2006.01) |
| *C07D 451/02* | (2006.01) |
| *C07D 471/08* | (2006.01) |
| *C07D 471/10* | (2006.01) |
| *C07D 491/08* | (2006.01) |
| *A61K 31/366* | (2006.01) |
| *A61K 31/397* | (2006.01) |
| *A61K 31/4985* | (2006.01) |
| *A61K 45/06* | (2006.01) |

(52) U.S. Cl.
CPC .......... *C07D 405/14* (2013.01); *C07D 311/04* (2013.01); *C07D 405/06* (2013.01); *C07D 451/02* (2013.01); *C07D 471/08* (2013.01); *C07D 471/10* (2013.01); *C07D 491/08* (2013.01); *A61K 31/366* (2013.01); *A61K 31/397* (2013.01); *A61K 31/4985* (2013.01); *A61K 45/06* (2013.01)

(58) Field of Classification Search
CPC .. C07D 405/14; C07D 405/06; C07D 311/04; C07D 451/02; C07D 471/08; C07D 471/10; C07D 491/08; A61K 31/366; A61K 31/397; A61K 31/4985; A61K 45/06
See application file for complete search history.

(56) References Cited

U.S. PATENT DOCUMENTS

| | | | | |
|---|---|---|---|---|
| 4,654,362 A | * | 3/1987 | Van Lommen | C07D 307/81 514/452 |
| 4,873,255 A | * | 10/1989 | Yoshioka | C07D 417/12 514/369 |
| 6,469,031 B1 | | 10/2002 | Connell et al. | |

(Continued)

FOREIGN PATENT DOCUMENTS

| | | |
|---|---|---|
| CN | 103030646 A | 4/2013 |
| GB | 2498976 A | 7/2013 |

(Continued)

OTHER PUBLICATIONS

Nguyen et al., 13(12) Org. & Biomol. Chem. 3749-3756 (2015) (Year: 2015).*

(Continued)

*Primary Examiner* — Timothy R Rozof
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

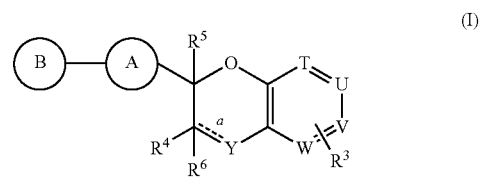

(I)

15 Claims, No Drawings

(56) References Cited

U.S. PATENT DOCUMENTS

| | | | |
|---|---|---|---|
| 2007/0219193 A1* | 9/2007 | Zhao | A61K 31/538 |
| | | | 514/230.5 |
| 2016/0002255 A1 | 1/2016 | Brockunier et al. | |
| 2016/0257701 A1 | 9/2016 | Desai et al. | |

FOREIGN PATENT DOCUMENTS

| | | |
|---|---|---|
| WO | 2002085900 A1 | 10/2002 |
| WO | WO2004022551 A1 | 3/2004 |
| WO | WO2004041266 A1 | 5/2004 |
| WO | 2004106298 A1 | 12/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007013689 A1 | 2/2007 |
| WO | WO2007033002 A1 | 3/2007 |
| WO | 2007109577 A1 | 9/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009111056 A1 | 9/2009 |
| WO | WO2010004347 A1 | 1/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | W02012072691 A1 | 6/2012 |
| WO | WO2012072691 A1 | 6/2012 |
| WO | 2012127385 A1 | 9/2012 |
| WO | WO2013122028 A1 | 8/2013 |
| WO | WO2013122029 A1 | 8/2013 |
| WO | WO2014130608 A1 | 8/2014 |
| WO | WO2015119899 A1 | 8/2015 |
| WO | WO2016019587 A1 | 2/2016 |
| WO | WO2016022448 A1 | 2/2016 |
| WO | WO2016022742 A1 | 2/2016 |
| WO | 2018106518 A1 | 6/2018 |

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.

Brown, S. P. et al., Discovery of AM-1638: A Potent and Orally Bioavailable GPR40/FFA1 Full Agonist, American Chemical Society, 2012, p. 726-730, vol. 3.

Executive Summary, Detection, Evaluation, and Treatment of High Blood Cholesterol in Adults (Adult Treatment Panel III), National Institutes of Health, 2001, pp. 1-40, NIH Publication No. 01-3670.

Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012,—.

Houze, J. B. et al., AMG 837: A potent, orally bioavailable GPR40 agonist, Bioorganic & Medicinal Chemistry Letters, 2012, p. 1267-1270, vol. 22.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS ONE, 2011, p. 1-10, vol. 6, No. 11.

Lou, J. et al., A Potent Class of GPR40 Full Agonist Engages the EnteroInsular Axis to Promote Glucose Control in Rodents, PLOS ONE, 2012, p. 6-12, vol. 7, Issue 10.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25,—.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

* cited by examiner

ANTIDIABETIC HETEROCYCLIC COMPOUNDS

CROSS-REFERENCE TO RELATED APPLICATIONS

This application is a U.S. National Phase application under 35 U.S.C. § 371 of PCT Application No. PCT/US2017/064106, filed on Dec. 1, 2017, which claims priority from and the benefit of U.S. Provisional Application Ser. No. 62/430,625, filed Dec. 6, 2016.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results induction and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); (5) inhibitors of incretin hormone degradation (DPP-4 inhibitors, such as sitagliptin, alogliptin, vildagliptin, linagliptin, denagliptin and saxagliptin); and SGLT2 inhibitors (canagliflozin, dapagliflozin and empagliflozin).

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature,* 422: 173 (2003); Briscoe, C. P. et al., *J. Biol. Chem.,* 278: 11303 (2003); Kotarsky, K. et al., *Biochem. Biophys. Res. Comm.,* 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/072691, WO 2013/122028, WO2013/122029, WO2014/130608, WO2016022448, WO2016022742 and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

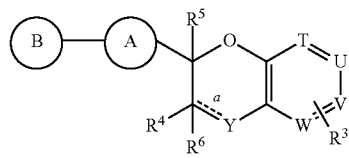

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

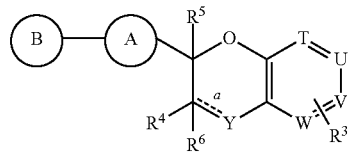

or a pharmaceutically acceptable salt thereof; wherein
"a" is a single bond or a double bond, provided that if "a" is a double bond, then $R^6$ is absent and Y is selected from the group consisting of: $C-R^g$, $-C-OC_{1-6}$alkyl, CF and N;
T is selected from the group consisting of:
 (1) CH,
 (2) N, and
 (3) N-oxide;
U is selected from the group consisting of:
 (1) $CR^1$,
 (2) N, and
 (3) N-oxide;
V is selected from the group consisting of:
 (1) $CR^2$,
 (2) N, and
 (3) N-oxide;
W is selected from the group consisting of:
 (1) CH,
 (2) N, and
 (3) N-oxide,
provided that no more than two of T, U, V and W are selected from N and N-oxide, further provided that if both T and W are N or N-oxide, then $R^3$ is absent, and further provided that both U and V are not N or N-oxide;
Y is selected from the group consisting of:
 (1) oxygen,
 (2) sulfur,
 (3) $-CR^gR^g$,
 (4) C=O,
 (5) $-C(R^g)OC_{1-6}$alkyl,
 (6) $-CF_2$, and
 (7) $-NR^c$;

A is selected from the group consisting of:
- (1) —$C_{1-6}$alkyl-N($R^n$)—,
- (2) —$C_{1-6}$alkyl-O—;
- (3) —$C_{1-6}$alkyl-$C_{7-15}$cycloalkyl,
- (4) —$C_{1-6}$alkyl-$C_{6-14}$cycloheteroalkyl,
- (5) —$C_{7-15}$cycloalkyl, and
- (6) —$C_{6-14}$cycloheteroalkyl, wherein A is unsubstituted or substituted with one to five substituents selected from $R^a$;

B is selected from the group consisting of:
- (1) hydrogen,
- (2) aryl,
- (3) aryl-O—,
- (4) aryl-$C_{1-10}$ alkyl-,
- (5) aryl-$C_{1-10}$ alkyl-O—,
- (6) $C_{3-6}$cycloalkyl,
- (7) $C_{3-6}$cycloalkyl-$C_{1-10}$alkyl-,
- (8) $C_{3-6}$cycloalkyl-$C_{1-10}$alkyl-O—,
- (9) $C_{3-6}$cycloalkenyl,
- (10) $C_{3-6}$cycloalkenyl-$C_{1-10}$alkyl-,
- (11) $C_{3-6}$cycloalkenyl-$C_{1-10}$alkyl-O—,
- (12) $C_{2-5}$cycloheteroalkyl,
- (13) $C_{3-6}$cycloheteroalkyl-$C_{1-10}$alkyl-,
- (14) $C_{3-6}$cycloheteroalkyl-$C_{1-10}$alkyl-O—,
- (15) heteroaryl,
- (16) heteroaryl-O—,
- (17) heteroaryl-$C_{1-10}$ alkyl-, and
- (18) heteroaryl-$C_{1-10}$ alkyl-O—, wherein B is unsubstituted or substituted with one to five substituents selected from $R^b$;

$R^1$ and $R^2$ are each independently selected from:
- (1) a bond,
- (2) hydrogen,
- (3) halogen,
- (4) —$OR^k$,
- (5) —CN,
- (6) —$C_{1-6}$alkyl,
- (7) —$C_{3-6}$cycloalkyl,
- (8) —$C_{3-6}$cycloalkyl-$C_{1-3}$alkyl-,
- (9) —$C_{2-6}$cycloheteroalkyl, and
- (10) —$C_{2-6}$cycloheteroalkyl-$C_{1-3}$alkyl-, wherein each —$OR^k$, alkyl, cycloalkyl and cycloheteroalkyl is unsubstituted or substituted with one to three substituents selected from $R^L$, and wherein one of $R^1$ and $R^2$ is selected from a bond, —$OR^k$, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein the bond, —$OR^k$, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl- is substituted with a substituent selected from $R^7$;

$R^3$ is selected from the group consisting of:
- (1) hydrogen,
- (2) halogen,
- (3) —$OR^e$,
- (4) —CN,
- (5) —$C_{1-6}$alkyl,
- (6) —$C_{3-6}$cycloalkyl, and
- (7) —$C_{3-6}$cycloalkyl-$C_{1-3}$alkyl-, wherein each alkyl and cycloalkyl is unsubstituted or substituted with one to three substituents selected from $R^i$;

$R^4$ is selected from the group consisting of:
- (1) hydrogen,
- (2) halogen,
- (3) $OR^e$,
- (4) $C_{1-6}$alkyl,
- (5) $C_{1-6}$alkyl-O—,
- (6) $C_{3-6}$cycloalkyl,
- (7) $C_{3-6}$cycloalkyl-O—,
- (8) $C_{3-6}$cycloalkyl-$C_{1-10}$alkyl-,
- (9) $C_{3-6}$cycloalkyl-$C_{1-10}$alkyl-O—,
- (10) $C_{2-5}$cycloheteroalkyl,
- (11) $C_{2-5}$cycloheteroalkyl-O—,
- (12) $C_{2-5}$cycloheteroalkyl-$C_{1-10}$alkyl-,
- (13) $C_{2-5}$cycloheteroalkyl-$C_{1-10}$alkyl-O—,
- (14) aryl,
- (15) aryl-O—,
- (16) aryl-$C_{1-10}$alkyl-,
- (17) heteroaryl,
- (18) heteroaryl-O—, and
- (19) heteroaryl-$C_{1-10}$alkyl-, wherein each alkyl, cycloalkyl, cycloheteroalkyl, aryl and heteroaryl is unsubstituted or substituted with one to three substituents selected from $R^j$, provided that when $R^4$ is selected from the group consisting of:
- (1) $OR^e$,
- (2) $C_{1-6}$alkyl-O—,
- (3) $C_{3-6}$cycloalkyl-O—,
- (4) $C_{3-6}$cycloalkyl-$C_{1-10}$alkyl-O—,
- (5) $C_{2-5}$cycloheteroalkyl-O—,
- (6) $C_{2-5}$cycloheteroalkyl-$C_{1-10}$alkyl-O—,
- (7) aryl-O—, and
- (8) heteroaryl-O—, then Y is selected from the group consisting of:
- (1) —$CR^gR^g$,
- (2) C=O,
- (3) —$C(R^g)OC_{1-6}$alkyl, and
- (4) —$CF_2$;

$R^5$ is selected from the group consisting of:
- (1) hydrogen,
- (2) —$C_{1-6}$alkyl, and
- (3) —$C_{3-6}$cycloalkyl, wherein each alkyl and cycloalkyl is unsubstituted or substituted with one to three substituents selected from $R^j$;

$R^6$ is selected from the group consisting of:
- (1) hydrogen,
- (2) —$C_{1-6}$alkyl, and
- (3) —$C_{3-6}$cycloalkyl, wherein each alkyl and cycloalkyl is unsubstituted or substituted with one to three substituents selected from $R^j$;

$R^7$ is selected from the group consisting of:
- (1) —$CO_2R^8$,
- (2) —$C_{1-6}$alkyl-$CO_2R^8$,
- (3) —$C_{1-6}$alkyl-$CONHSO_2R^m$,
- (4) —$C_{1-6}$alkyl-$SO_2NHCOR^m$,
- (5) —$C_{1-6}$alkyl-tetrazolyl, and
- (6) a cycloheteroalkyl selected from the group consisting of:

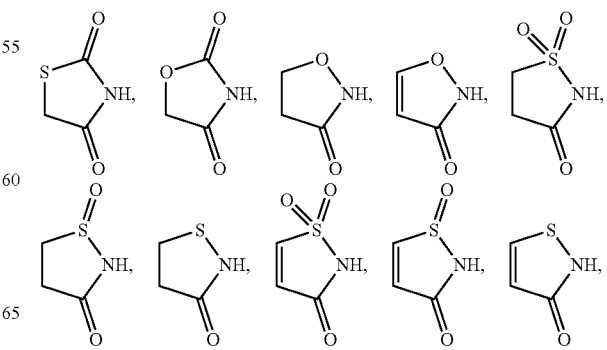

-continued

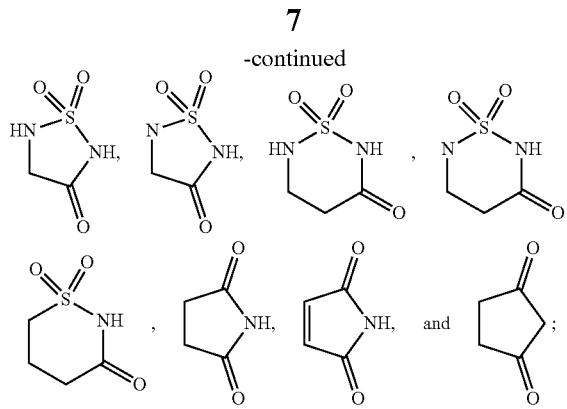

R⁸ is selected from the group consisting of:
(1) hydrogen,
(2) —$C_{1-6}$alkyl,
(3) —$C_{3-6}$cycloalkyl, and
(4) aryl-$C_{1-6}$-alkyl,
wherein each alkyl, cycloalkyl and aryl is unsubstituted or substituted with one to three substituents selected from $R^j$;
$R^a$ is selected from the group consisting of:
(1) —$C_{1-6}$alkyl,
(2) halogen,
(3) —$OR^e$,
(4) —$NR^cS(O)_nR^e$,
(5) —$S(O)_nR^e$,
(6) —$S(O)_nNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) aryl,
(20) heteroaryl,
(21) —$C_{3-6}$cycloalkyl,
(22) —$C_{3-6}$cycloalkenyl, and
(23) —$C_{2-5}$cycloheteroalkyl,
wherein each alkyl, cycloalkyl, cycloalkenyl, cycloheteroalkyl, aryl and heteroaryl is unsubstituted or substituted with —$C_{1-6}$alkyl, halogen, —O—$C_{1-6}$alkyl and —$CF_3$;
$R^b$ is independently selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)_pOC_{1-10}$alkyl,
(10) —$O(CH_2)_pC_{3-6}$cycloalkyl,
(11) —$O(CH_2)_pC_{3-6}$ cycloalkyl-$C_{1-10}$alkyl-,
(12) —$O(CH_2)_pC_{2-5}$cycloheteroalkyl,
(13) —$O(CH_2)_pC_{2-5}$cycloheteroalkyl-$C_{1-10}$alkyl-,
(14) —O-aryl,
(15) —O-heteroaryl,
(16) —O-aryl-$C_{1-10}$alkyl-,
(17) —O-heteroaryl-$C_{1-10}$alkyl-,
(18) —$O(CH_2)_pNR^cS(O)_mR^e$,
(19) —$O(CH_2)_pS(O)_mR^e$,
(20) —$O(CH_2)_pS(O)_mNR^cR^d$,
(21) —$O(CH_2)_pNR^cR^d$,
(22) —$C(O)R^e$,
(23) —$OC(O)R^e$,
(24) —$CO_2R^e$,
(25) —$C(O)NR^cR^d$,
(26) —$NR^cC(O)R^e$,
(27) —$NR^cC(O)OR^e$,
(28) —$NR^cC(O)NR^cR^d$,
(29) —$O(CH_2)_pO$—$C_{3-6}$cycloalkyl,
(30) —$O(CH_2)_pO$—$C_{2-5}$cycloheteroalkyl,
(31) —$OCF_3$,
(32) —$OCHF_2$,
(33) —$(CH_2)_pC_{3-6}$cycloalkyl,
(34) —$(CH_2)_pC_{2-5}$cycloheteroalkyl,
(35) aryl,
(36) heteroaryl,
(37) aryl-$C_{1-10}$alkyl-, and
(38) heteroaryl-$C_{1-10}$alkyl-,
wherein each CH, $CH_2$, alkyl, alkenyl, cycloalkyl, cycloheteroalkyl, aryl and heteroaryl is unsubstituted or substituted with —$C_{1-6}$alkyl, halogen, —O—$C_{1-6}$alkyl and —$CF_3$;
$R^c$ and $R^d$ are each independently selected from the group consisting of:
(1) hydrogen,
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl,
(7) $C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents independently selected from $R^f$;
each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) aryl-$C_{1-10}$alkyl-,
(10) heteroaryl, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents selected from $R^h$;
each $R^f$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;

each $R^g$ is selected from the group consisting of:
(1) hydrogen,
(2) —C(O)$R^e$, and
(3) —C$_{1-10}$alkyl,
wherein each alkyl is unsubstituted or substituted with one to five halogens;
each $R^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
$R^i$ is independently selected from the group consisting of:
(1) —C$_{1-6}$alkyl,
(2) —O$R^e$,
(3) —N$R^c$S(O)$_m R^e$,
(4) halogen,
(5) —S(O)$_m R^e$,
(6) —S(O)$_m$N$R^c R^d$,
(7) —N$R^c R^d$,
(8) —C(O)$R^e$,
(9) —OC(O)$R^e$,
(10) —CO$_2 R^e$,
(11) —CN,
(12) —C(O)N$R^c R^d$,
(13) —N$R^c$C(O)$R^e$,
(14) —N$R^c$C(O)O$R^e$,
(15) —N$R^c$C(O)N$R^c R^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
$R^j$ is independently selected from the group consisting of:
(1) —C$_{1-6}$alkyl,
(2) —O$R^e$,
(3) —N$R^c$S(O)$_m R^e$,
(4) halogen,
(5) —S(O)$_m R^e$,
(6) —S(O)$_m$N$R^c R^d$,
(7) —N$R^c R^d$,
(8) —C(O)$R^e$,
(9) —OC(O)$R^e$,
(10) —CO$_2 R^e$,
(11) —CN,
(12) —C(O)N$R^c R^d$,
(13) —N$R^c$C(O)$R^e$,
(14) —N$R^c$C(O)O$R^e$,
(15) —N$R^c$C(O)N$R^c R^d$,
(16) —CF$_3$,
(17) —OCF$_3$,
(18) —OCHF$_2$,
(19) —C$_{3-6}$cycloalkyl, and
(20) —C$_{2-5}$ cycloheteroalkyl;
each $R^k$ is independently selected from the group consisting of:
(1) hydrogen,
(2) —C$_{1-6}$ alkyl,
(3) —C$_{1-6}$alkyl-SO$_2$C$_{1-6}$alkyl,
(4) —CF$_3$, and
(5) —CHF$_2$,
wherein each alkyl is unsubstituted or substituted with one to three substituents independently selected from: —OH, —OC$_{1-6}$alkyl, halogen, cyano, and —S(O)$_2$C$_{1-6}$alkyl;
each $R^L$ is independently selected from the group consisting of:
(1) —CO$_2$C$_{1-6}$alkyl,
(2) —C$_{1-10}$alkyl,
(3) —C$_{2-10}$ alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with 1-4 substituents selected from C$_{1-6}$alkyl, halogen, and —OC$_{1-6}$alkyl;
each $R^m$ is independently selected from the group consisting of:
(1) —C$_{1-10}$alkyl,
(2) —C$_{2-10}$ alkenyl,
(3) —C$_{3-6}$ cycloalkyl,
(4) —C$_{3-6}$ cycloalkyl-C$_{1-10}$alkyl-,
(5) —C$_{2-5}$cycloheteroalkyl,
(6) —C$_{2-5}$cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;
$R^n$ is selected from the group consisting of:
(1) hydrogen, and
(2) —C$_{1-10}$alkyl,
wherein each alkyl is unsubstituted or substituted with one to five halogens;
each n is independently selected from: 0, 1 or 2;
each m is independently selected from: 0, 1 or 2; and
each p is independently selected from: 0, 1, 2, 3, 4, 5 or 6.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, "a" is a single bond.

In another embodiment of the present invention, "a" is a single bond, and Y is selected from the group consisting of: oxygen, sulfur, —C$R^g R^g$, C=O, —C($R^g$)OC$_{1-6}$alkyl, —CF$_2$, and —N$R^c$. In another embodiment of the present invention, "a" is a single bond and $R^6$ is present. In another embodiment of the present invention, "a" is a double bond and $R^6$ is absent.

In another embodiment of the present invention, "a" is a double bond, $R^6$ is absent and Y is selected from the group consisting of: C—$R^g$, CF, and N. In a class of this embodiment, Y is selected from the group consisting of: —CH, —CF, and —N. In another class of this embodiment, Y is selected from the group consisting of: —C—$R^g$. In a subclass of this class, Y is —CH.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: $CR^1$, N and N-oxide. In a class of this embodiment, U is selected from the group consisting of: $CR^1$ and N. In another class of this embodiment, U is $CR^1$. In another class of this embodiment, U is N or N-oxide. In another class of this embodiment, U is N.

In another class of this embodiment, U is N-oxide.

In another embodiment of the present invention, V is selected from the group consisting of: $CR^2$, N and N-oxide. In a class of this embodiment, V is selected from the group consisting of: $CR^2$ and N. In another class of this embodiment, V is $CR^2$. In another class of this embodiment, V is N or N-oxide. In another class of this embodiment, V is N. In another class of this embodiment, V is N-oxide.

In another embodiment of the present invention, W is selected from the group consisting of: CH, N and N-oxide, provided that no more than two of T, U, V and W are selected from N and N-oxide, further provided that if both T and W are N or N-oxide, then $R^3$ is absent, and further provided that both U and V are not N or N-oxide. In a class of this embodiment, W is selected from the group consisting of: CH and N, provided that no more than two of T, U, V and W are selected from N and N-oxide, further provided that if both T and W are N or N-oxide, then $R^3$ is absent, and further provided that both U and V are not N or N-oxide. In another class of this embodiment, W is CH, provided that no more than two of T, U, V and W are selected from N and N-oxide, further provided that if both T and W are N or N-oxide, then $R^3$ is absent, and further provided that both U and V are not N or N-oxide. In another class of this embodiment, W is N or N-oxide, provided that no more than two of T, U, V and W are selected from N and N-oxide, further provided that if both T and W are N or N-oxide, then $R^3$ is absent, and further provided that both U and V are not N or N-oxide. In another class of this embodiment, W is N, provided that no more than two of T, U, V and W are selected from N and N-oxide, further provided that if both T and W are N or N-oxide, then $R^3$ is absent, and further provided that both U and V are not N or N-oxide.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T is CH, U is $CR^1$, V is $CR^2$, and W is CH. In a class of this embodiment, T is CH, U is $CR^1$, V is CH, and W is CH. In another class of this embodiment, T is CH, U is CH, V is $CR^2$, and W is CH. In another embodiment of the present invention, T is N or N-oxide, U is $CR^1$, V is $CR^2$, and W is CH. In a class of this embodiment, T is N, U is $CR^1$, V is $CR^2$, and W is CH. In another embodiment of the present invention, T is CH, U is N or N-oxide, and V is $CR^2$, and W is CH. In a class of this embodiment, T is CH, U is N, V is $CR^2$, and W is CH. In another embodiment of the present invention, T is CH, U is $CR^1$, V is N or N-oxide, and W is CH. In a class of this embodiment, T is CH, U is $CR^1$, and V is N or N-oxide, and W is CH. In another embodiment of the present invention, T is CH, U is $CR^1$, V is $CR^2$, and W is CH, N or N-oxide. In another embodiment of the present invention, T is CH, U is $CR^1$, V is $CR^2$, and W is N or N-oxide. In a class of this embodiment, T is CH, U is $CR^1$, V is $CR^2$, and W is N. In another embodiment of the present invention, T is N or N-oxide, U is N or N-oxide, V is $CR^2$, and W is CH. In a class of this embodiment, T is N, U is N, V is $CR^2$, and W is CH. In another embodiment of the present invention, T is N or N-oxide, U is $CR^1$, V is N or N-oxide, and W is CH. In a class of this embodiment, T is N, U is $CR^1$, V is N, and W is CH.

In another embodiment of the present invention, T is N or N-oxide, U is $CR^1$, V is $CR^2$, and W is N or N-oxide. In a class of this embodiment, T is N, U is $CR^1$, V is $CR^2$, and W is N. In another embodiment of the present invention, T is N or N-oxide, U is $CR^1$, V is $CR^2$, and W is N or N-oxide; and $R^3$ is absent. In a class of this embodiment, T is N, U is $CR^1$, V is $CR^2$, and W is N; and $R^3$ is absent. In another embodiment of the present invention, T is CH, U is N or N-oxide, V is $CR^2$, and W is N or N-oxide. In a class of this embodiment, T is CH, U is N, V is $CR^2$, and W is N. In another embodiment of the present invention, T is CH, U is $CR^1$, V is N or N-oxide, and W is N or N-oxide. In a class of this embodiment, T is CH, U is $CR^1$, V is N, and W is N. In another embodiment of the present invention, T is CH; U is $CR^1$; V is $CR^2$; and W is CH, N or N-oxide.

In another embodiment of the present invention, Y is selected from the group consisting of: oxygen and sulfur.

In another embodiment of the present invention, Y is selected from the group consisting of: $—CR^gR^g$, $C=O$, $—CF_2$, and $—NR^c$. In a class of this embodiment, Y is selected from the group consisting of: $—CH_2$, $C=O$, $—CF_2$, and $—NH$. In another embodiment of the present invention, Y is selected from the group consisting of: $—CR^gR^g$, $C=O$, and $—CF_2$. In a class of this embodiment, Y is selected from the group consisting of: $—CH_2$, $C=O$, and $—CF_2$. In another embodiment of the present invention, Y is selected from the group consisting of: $—CR^gR^g$. In a class of this embodiment, Y is $—CH_2$.

In another embodiment of the present invention, A is selected from the group consisting of: $—C_{1-6}alkyl-N(R'')—$, $—C_{1-6}alkyl-C_{7-15}cycloalkyl$, $—C_{1-6}alkyl-C_{6-14}cycloheteroalkyl$, $—C_{7-15}cycloalkyl$, and $—C_{6-14}cycloheteroalkyl$, wherein A is unsubstituted or substituted with one to five substituents selected from $R^a$.

In another embodiment of the present invention, A is selected from the group consisting of: $—C_{1-6}alkyl-N(R'')—$, $—C_{1-6}alkyl-C_{6-14}cycloheteroalkyl$, and $—C_{6-14}cycloheteroalkyl$, wherein A is unsubstituted or substituted with one to five substituents selected from $R^a$. In a class of this embodiment, A is selected from the group consisting of: $—CH_2CH_2—N(CH_3)—$, $—CH_2$-piperidine, 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane, wherein A is unsubstituted or substituted with one to five substituents selected from $R^a$. In another class of this embodiment, A is selected from the group consisting of: $—CH_2CH_2—N(CH_3)—$, $—CH_2$-piperidine, 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane.

In another embodiment of the present invention, A is $—C_{1-6}alkyl-N(R'')—$, wherein A is unsubstituted or substituted with one to five substituents selected from $R^a$. In a class of this embodiment, A is $—CH_2CH_2—N(CH_3)—$, wherein A is unsubstituted or substituted with one to five substituents selected from $R^a$. In another class of this embodiment, A is $—CH_2CH_2—N(CH_3)—$.

In another embodiment of the present invention, A is selected from the group consisting of: $—C_{1-6}alkyl-C_{6-14}cycloheteroalkyl$, and $—C_{6-14}cycloheteroalkyl$, wherein A is unsubstituted or substituted with one to five substituents selected from $R^a$. In a class of this embodiment, A is selected from the group consisting of: —CH$_2$-piperidine, 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane, wherein A is unsubstituted or substituted with one to five substituents selected from $R^a$. In another class of this embodiment, A is selected from the group consisting of: —CH$_2$-piperidine, 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane.

In another embodiment of the present invention, A is —C$_{1-6}$alkyl-C$_{6-14}$cycloheteroalkyl, wherein A is unsubstituted or substituted with one to five substituents selected from $R^a$. In a class of this embodiment, A is —CH$_2$-piperidine-, wherein A is unsubstituted or substituted with one to five substituents selected from $R^a$. In another class of this embodiment, A is —CH$_2$-piperidine-.

In another embodiment of the present invention, A is —C$_{6-14}$cycloheteroalkyl-, wherein A is unsubstituted or substituted with one to five substituents selected from $R^a$. In a class of this embodiment, A is selected from the group consisting of: 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane, wherein A is unsubstituted or substituted with one to five substituents selected from $R^a$. In another class of this embodiment, A is selected from the group consisting of: 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane.

In another embodiment of the present invention, A is selected from the group consisting of: —C$_{1-6}$alkyl-N(R")—, and —C$_{6-14}$cycloheteroalkyl-, wherein A is unsubstituted or substituted with one to five substituents selected from $R^a$. In a class of this embodiment, A is unsubstituted or substituted with one to three substituents selected from $R^a$. In another class of this embodiment, A is unsubstituted or substituted with one to two substituents selected from $R^a$.

In another embodiment of the present invention, A is selected from the group consisting of —(CH$_2$)$_2$—N(CH$_3$)—, 2-aza-bicyclo[2.2.1]heptane, and 2-azabicyclo-[3.1.1]heptane, wherein A is unsubstituted or substituted with one to five substituents selected from $R^a$. In a class of this embodiment, A is unsubstituted or substituted with one to three substituents selected from $R^a$. In another class of this embodiment, A is unsubstituted or substituted with one to two substituents selected from $R^a$.

In another embodiment of the present invention, A is —C$_{1-6}$alkyl-N(R")—, wherein A is unsubstituted or substituted with one to five substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is —(CH$_2$)$_2$—N(CH$_3$)—, wherein A is unsubstituted or substituted with one to five substituents selected from $R^a$. In a subclass of this class, A is unsubstituted or substituted with one to three substituents selected from $R^a$. In another subclass of this class, A is unsubstituted or substituted with one to two substituents selected from $R^a$.

In another embodiment of the present invention, A is —C$_{6-14}$cycloheteroalkyl-, wherein A is unsubstituted or substituted with one to five substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is 2-aza-bicyclo[2.2.1]heptane or 2-azabicyclo[3.1.1]heptane, wherein A is unsubstituted or substituted with one to five substituents selected from $R^a$. In a subclass of this class, A is unsubstituted or substituted with one to three substituents selected from $R^a$. In another subclass of this class, A is unsubstituted or substituted with one to two substituents selected from $R^a$.

In another embodiment of the present invention, B is selected from the group consisting of aryl, aryl-O—, aryl-C$_{1-10}$ alkyl-, aryl-C$_{1-10}$ alkyl-O—, C$_{3-6}$cycloalkyl, C$_{3-6}$cycloalkyl-C$_{1-10}$alkyl-, C$_{3-6}$cycloalkyl-C$_{1-10}$alkyl-O—, C$_{3-6}$cycloalkenyl, C$_{3-6}$cycloalkenyl-C$_{1-10}$alkyl-, C$_{3-6}$cycloalkenyl-C$_{1-10}$alkyl-O—, C$_{2-5}$cycloheteroalkyl, C$_{3-6}$cycloheteroalkyl-C$_{1-10}$alkyl-, C$_{3-6}$cycloheteroalkyl-C$_{1-10}$alkyl-O—, heteroaryl, heteroaryl-O—, heteroaryl-C$_{1-10}$ alkyl-, and heteroaryl-C$_{1-10}$ alkyl-O—, wherein B is unsubstituted or substituted with one to five substituents selected from $R^b$.

In another embodiment of the present invention, B is selected from the group consisting of aryl, aryl-C$_{1-10}$ alkyl-, C$_{3-6}$cycloalkyl, C$_{3-6}$cycloalkyl-C$_{1-10}$alkyl-, C$_{3-6}$cycloalkenyl, C$_{3-6}$cycloalkenyl-C$_{1-10}$alkyl-, C$_{2-5}$cycloheteroalkyl, C$_{3-6}$cycloheteroalkyl-C$_{1-10}$alkyl-, heteroaryl and heteroaryl-C$_{1-10}$ alkyl-, wherein B is unsubstituted or substituted with one to five substituents selected from $R^b$.

In another embodiment of the present invention, B is selected from the group consisting of: aryl, aryl-C$_{1-10}$ alkyl-, heteroaryl, and heteroaryl-C$_{1-10}$ alkyl-, wherein B is unsubstituted or substituted with one to five substituents selected from $R^b$.

In another embodiment of the present invention, B is selected from the group consisting of: aryl-C$_{1-10}$ alkyl-, and heteroaryl, wherein B is unsubstituted or substituted with one to five substituents selected from $R^b$. In a class of this embodiment, B is selected from the group consisting of: phenyl-CH$_2$—, and pyridine, wherein B is unsubstituted or substituted with one to five substituents selected from $R^b$.

In another embodiment of the present invention, B is heteroaryl, wherein B is unsubstituted or substituted with one to five substituents selected from $R^b$. In a class of this embodiment, B is pyridine, wherein pyridine is unsubstituted or substituted with one to five substituents selected from $R^b$.

In another embodiment of the present invention, B is aryl-C$_{1-10}$ alkyl-, wherein B is unsubstituted or substituted with one to five substituents selected from $R^b$. In a class of this embodiment, B is unsubstituted or substituted with one to three substituents selected from $R^b$. In another class of this embodiment, B is unsubstituted or substituted with one to two substituents selected from $R^b$.

In another embodiment of the present invention, B is phenyl-C$_{1-10}$ alkyl-, wherein B is unsubstituted or substituted with one to five substituents selected from $R^b$. In a class of this embodiment, B is unsubstituted or substituted with one to three substituents selected from $R^b$. In another class of this embodiment, B is unsubstituted or substituted with one to two substituents selected from $R^b$.

In another embodiment of the present invention, B is phenyl-CH$_2$—, wherein B is unsubstituted or substituted with one to five substituents selected from $R^b$. In a class of this embodiment, B is unsubstituted or substituted with one to three substituents selected from $R^b$. In another class of this embodiment, B is unsubstituted or substituted with one to two substituents selected from $R^b$.

In another embodiment of the present invention, B is aryl-$C_{1-10}$ alkyl-, wherein aryl and alkyl are unsubstituted or substituted with one to five substituents selected from $R^b$. In a class of this embodiment, B is phenyl-$CH_2$—, wherein B is unsubstituted or substituted with one to five substituents selected from $R^b$.

In another embodiment of the present invention, B is heteroaryl, wherein heteroaryl is unsubstituted or substituted with one to five substituents selected from $R^b$. In a class of this embodiment, B is pyridine, wherein pyridine is unsubstituted or substituted with one to five substituents selected from $R^b$.

In another embodiment of the present invention, $R^1$ and $R^2$ are each independently selected from: a bond, hydrogen, —$OR^k$, and —$C_{1-6}$alkyl, wherein each —$OR^k$ and alkyl is unsubstituted or substituted with one to three substituents selected from $R^L$, and wherein one of $R^1$ and $R^2$ is selected from a bond, —$OR^k$, and —$C_{1-6}$alkyl, wherein the bond, —$OR^k$, -and —$C_{1-6}$alkyl is substituted with $R^7$.

In another embodiment of the present invention, $R^1$ and $R^2$ are each independently selected from: hydrogen, —$OR^k$, and —$C_{1-6}$alkyl, wherein each —$OR^k$ and alkyl is unsubstituted or substituted with one to three substituents selected from $R^L$, and wherein one of $R^1$ and $R^2$ is selected from —$OR^k$ and —$C_{1-6}$alkyl, wherein —$OR^k$ and —$C_{1-6}$alkyl is substituted with a substituent selected from $R^7$.

In another embodiment of the present invention, $R^1$ and $R^2$ are each independently selected from: a bond, hydrogen, and —$C_{1-6}$alkyl, wherein each alkyl is unsubstituted or substituted with one to three substituents selected from $R^L$, and wherein one of $R^1$ and $R^2$ is selected from a bond and —$C_{1-6}$alkyl, wherein the bond and —$C_{1-6}$alkyl is substituted with a substituent selected from $R^7$.

In another embodiment of the present invention, $R^1$ and $R^2$ are each independently selected from: hydrogen and —$C_{1-6}$alkyl, wherein each alkyl is unsubstituted or substituted with one to three substituents selected from $R^L$, and wherein at least one of $R^1$ and $R^2$ is $C_{1-6}$alkyl, wherein —$C_{1-6}$alkyl is substituted with a substituent selected from $R^7$.

In another embodiment of the present invention, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is $C_{1-6}$alkyl, wherein —$C_{1-6}$alkyl is substituted with a substituent selected from $R^7$.

In another embodiment of the present invention, $R^1$ and $R^2$ are each independently selected from: hydrogen and —$C_2$alkyl, wherein each alkyl is unsubstituted or substituted with one to three substituents selected from $R^L$, and wherein at least one of $R^1$ and $R^2$ is $C_2$alkyl, wherein —$C_2$alkyl is substituted with a substituent selected from $R^7$.

In another embodiment of the present invention, $R^1$ and $R^2$ are each independently selected from: hydrogen and —$C_2$alkyl, wherein each alkyl is unsubstituted or substituted with one to three substituents selected from $R^L$, and wherein one of $R^1$ and $R^2$ is $C_2$alkyl, wherein —$C_2$alkyl is substituted with a substituent selected from $R^7$.

In another embodiment of the present invention, $R^1$ and $R^2$ are each independently selected from: hydrogen and —$C_2$alkyl, wherein each alkyl is substituted with one to three substituents selected from $R^L$, and wherein at least one of $R^1$ and $R^2$ is $C_2$alkyl, wherein —$C_2$alkyl is substituted with a substituent selected from $R^7$.

In another embodiment of the present invention, $R^1$ and $R^2$ are each independently selected from: hydrogen and —$C_2$alkyl, wherein each alkyl is substituted with one to three substituents selected from $R^L$, and wherein one of $R^1$ and $R^2$ is $C_2$alkyl, wherein —$C_2$alkyl is substituted with a substituent selected from $R^7$.

In another embodiment, $R^1$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$ cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is selected from: a bond, hydrogen, —$OR^k$ and —$C_{1-6}$alkyl, wherein each alkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is selected from: a bond, hydrogen and —$C_{1-6}$alkyl, wherein each alkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is selected from: hydrogen, and —$C_{1-6}$alkyl, wherein each alkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is selected from: hydrogen and —$C_2$alkyl-, wherein each alkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is selected from: —$C_{1-6}$alkyl, wherein each alkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is —$C_2$alkyl-, wherein each alkyl is unsubstituted or substituted with one to three substituents selected from $R^L$, and wherein $R^1$ is unsubstituted or substituted with a substituent selected from $R^7$. In a class of this embodiment, $R^1$ is substituted with a substituent selected from $R^7$.

In another embodiment of the present invention, $R^1$ is hydrogen. In another embodiment, $R^2$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is selected from: a bond, hydrogen, —$OR^k$ and —$C_{1-6}$alkyl, wherein each alkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is selected from: a bond, hydrogen and —$C_{1-6}$alkyl, wherein each alkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is selected from: hydrogen and —$C_{1-6}$alkyl, wherein each alkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is selected from: hydrogen and —$C_2$alkyl-, wherein each alkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is selected from: —$C_{1-6}$alkyl, wherein each alkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is —$C_2$alkyl-, wherein each alkyl is unsubstituted or substituted with one to three substituents selected from $R^L$, and wherein $R^2$ is unsubstituted or substituted with a substituent selected from $R^7$. In a class of this embodiment, $R^2$ is substituted with a substituent selected from $R^7$.

In another embodiment of the present invention, $R^2$ is hydrogen.

In another embodiment, $R^1$ is independently selected from: a bond, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with a substituent selected from $R^7$; and $R^2$ is hydrogen.

In another embodiment of the present invention, $R^1$ is selected from: a bond, —$OR^k$ and —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen.

In another embodiment of the present invention, $R^1$ is selected from: a bond and —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen. In a class of this embodiment, $R^1$ is selected from: a bond and —$C_2$alkyl-, wherein each alkyl is unsubstituted or substituted with one to three substituents selected from $R^L$, and wherein $R^1$ is substituted with a substituent selected from $R^7$; and $R^2$ is hydrogen.

In another embodiment of the present invention, $R^1$ is selected from: —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen. In a class of this embodiment, $R^1$ is selected from: —$C_2$alkyl-, wherein each alkyl is unsubstituted or substituted with one to three substituents selected from $R^L$, and wherein $R^1$ is substituted with a substituent selected from $R^7$; and $R^2$ is hydrogen.

In another embodiment, $R^2$ is independently selected from: a bond, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with a substituent selected from $R^7$; and $R^1$ is hydrogen.

In another embodiment of the present invention, $R^2$ is selected from: a bond, —$OR^k$ and —$C_{1-6}$alkyl, wherein each alkyl is unsubstituted or substituted with one to three substituents selected from $R^L$, and wherein $R^2$ is substituted with a substituent selected from $R^7$; and $R^1$ is hydrogen.

In another embodiment of the present invention, $R^2$ is selected from: a bond and —$C_{1-6}$alkyl, wherein each alkyl is unsubstituted or substituted with one to three substituents selected from $R^L$, and wherein $R^2$ is substituted with a substituent selected from $R^7$; and $R^1$ is hydrogen. In a class of this embodiment, $R^2$ is selected from: a bond and —$C_2$alkyl-, wherein each alkyl is unsubstituted or substituted with one to three substituents selected from $R^L$, and wherein $R^2$ is substituted with a substituent selected from $R^7$; and $R^1$ is hydrogen.

In another embodiment of the present invention, $R^2$ is selected from: —$C_{1-6}$alkyl, wherein each alkyl is unsubstituted or substituted with one to three substituents selected from $R^L$, and wherein $R^2$ is substituted with a substituent selected from $R^7$; and $R^1$ is hydrogen. In a class of this embodiment, $R^2$ is selected from: —$C_2$alkyl-, wherein each alkyl is unsubstituted or substituted with one to three substituents selected from $R^L$, and wherein $R^2$ is substituted with a substituent selected from $R^7$; and $R^1$ is hydrogen.

In another embodiment, $R^3$ is absent or when present is selected from the group consisting of: hydrogen, halogen, —$OR^e$, —CN, —$C_{1-6}$alkyl, —$C_{3-6}$cycloalkyl, and —$C_{3-6}$cycloalkyl-$C_{1-3}$alkyl-, wherein each alkyl and cycloalkyl is unsubstituted or substituted with one to three substituents selected from $R^i$.

In another embodiment of the present invention, when present, $R^3$ is selected from the group consisting of: hydrogen, halogen, —$OR^e$, —CN and —$C_{1-6}$alkyl, wherein each alkyl is unsubstituted or substituted with one to three substituents selected from $R^i$.

In another embodiment of the present invention, when present, $R^3$ is selected from the group consisting of: hydrogen, halogen and —$C_{1-6}$alkyl, wherein each alkyl is unsubstituted or substituted with one to three substituents selected from $R^i$. In a class of this embodiment, when present, $R^3$ is selected from the group consisting of: hydrogen and —$C_{1-6}$alkyl, wherein each alkyl is unsubstituted or substituted with one to three substituents selected from $R^i$. In another class of this embodiment, when present, $R^3$ is selected from the group consisting of: —$C_{1-6}$alkyl, wherein each alkyl is unsubstituted or substituted with one to three substituents selected from R$^i$. In another class of this embodiment, when present R$^3$ is hydrogen.

In another embodiment of the present invention, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$, and —C$_{1-6}$alkyl-O—, then Y is selected from the group consisting of: —CR$^g$R$^g$, C=O, —C(R$^g$)OC$_{1-6}$alkyl, and —CF$_2$. In a class of this embodiment, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$, and —C$_{1-6}$alkyl-O—, then Y is selected from the group consisting of: —CR$^g$R$^g$, C=O and —CF$_2$. In another class of this embodiment, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CH$_2$, C=O, and —CF$_2$.

In another embodiment of the present invention, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CR$^g$R$^g$. In another class of this embodiment, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^i$, provided that when R$^4$ is selected from the group consisting of: OR$^e$ and —C$_{1-6}$alkyl-O—, then Y is —CH$_2$.

In another embodiment of the present invention, R$^4$ is selected from the group consisting of: hydrogen, halogen and C$_{1-6}$alkyl, wherein each alkyl is unsubstituted or substituted with one to three substituents selected from R$^j$.

In another embodiment of the present invention, R$^4$ is selected from the group consisting of: hydrogen and C$_{1-6}$alkyl, wherein each alkyl is unsubstituted or substituted with one to three substituents selected from R$^j$.

In another embodiment of the present invention, R$^4$ is selected from the group consisting of: —C$_{1-6}$alkyl, wherein each alkyl is unsubstituted or substituted with one to three substituents selected from R$^j$.

In another embodiment of the present invention, R$^4$ is hydrogen.

In another embodiment of the present invention, R$^5$ is selected from the group consisting of: hydrogen, —C$_{1-6}$alkyl and —C$_{3-6}$cycloalkyl, wherein each alkyl and cycloalkyl is unsubstituted or substituted with one to three substituents selected from R$^j$.

In another embodiment of the present invention, R$^5$ is selected from the group consisting of: hydrogen and —C$_{1-6}$alkyl, wherein each alkyl is unsubstituted or substituted with one to three substituents selected from R$^j$. In another embodiment of the present invention, R$^5$ is selected from the group consisting of: —C$_{1-6}$alkyl, wherein each alkyl is unsubstituted or substituted with one to three substituents selected from R$^j$. In another embodiment of the present invention, R$^5$ is hydrogen.

In another embodiment of the present invention, R$^6$ is absent, or when present R$^6$ is selected from the group consisting of: hydrogen, —C$_{1-6}$alkyl, and —C$_{3-6}$cycloalkyl, wherein each alkyl and cycloalkyl is unsubstituted or substituted with one to three substituents selected from R$^j$.

In another embodiment of the present invention, R$^6$ is absent, or when present R$^6$ is selected from the group consisting of: hydrogen and —C$_{1-6}$alkyl, wherein each alkyl is unsubstituted or substituted with one to three substituents selected from R$^j$. In a class of this embodiment, R$^6$ is absent, or when present R$^6$ is selected from the group consisting of: —C$_{1-6}$alkyl, wherein each alkyl is unsubstituted or substituted with one to three substituents selected from R$^j$. In another class of this embodiment, R$^6$ is absent, or when present R$^6$ is hydrogen.

In another embodiment of the present invention, R$^6$ is selected from the group consisting of: hydrogen, —C$_{1-6}$alkyl, and —C$_{3-6}$cycloalkyl, wherein each alkyl and cycloalkyl is unsubstituted or substituted with one to three substituents selected from R$^j$.

In another embodiment of the present invention, R$^6$ is selected from the group consisting of: hydrogen and —C$_{1-6}$alkyl, wherein each alkyl is unsubstituted or substituted with one to three substituents selected from R$^j$. In a class of this embodiment, R$^6$ is selected from the group consisting of: —C$_{1-6}$alkyl, wherein each alkyl is unsubstituted or substituted with one to three substituents selected from R$^j$. In another class of this embodiment, R$^6$ is hydrogen.

In another embodiment of the present invention, R$^7$ is selected from the group consisting of: —CO$_2$R$^8$, —C$_{1-6}$alkyl-CO$_2$R$^8$, and a cycloheteroalkyl selected from the group consisting of:

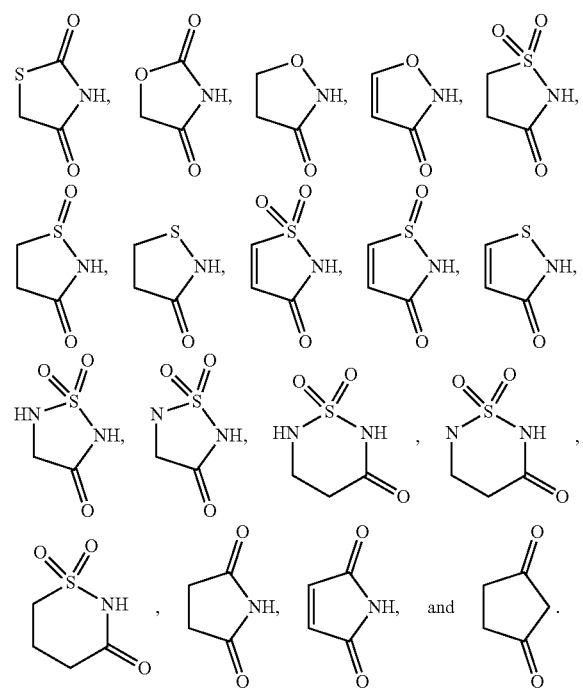

In another embodiment of the present invention, R$^7$ is —CO$_2$R$^8$. In a class of this embodiment, R$^7$ is —CO$_2$H.

In another embodiment of the present invention, R$^8$ is selected from the group consisting of: hydrogen, —C$_{1-6}$alkyl and —C$_{3-6}$cycloalkyl, wherein each alkyl and cycloalkyl is unsubstituted or substituted with one to three substituents selected from $R^j$. In a class of this embodiment, $R^8$ is selected from the group consisting of: hydrogen and —$C_{1-6}$alkyl, wherein each alkyl is unsubstituted or substituted with one to three substituents selected from $R^j$. In another class of this embodiment, $R^8$ is selected from the group consisting of: hydrogen and —$C_{1-6}$alkyl. In another class of this embodiment, $R^8$ is —$C_{1-6}$alkyl, wherein each alkyl is unsubstituted or substituted with one to three substituents selected from $R^j$. In another class of this embodiment, $R^8$ is hydrogen.

In another embodiment of the present invention, $R^a$ is selected from the group consisting of: —$C_{1-6}$alkyl, halogen, —$OR^e$, —$NR^cS(O)_nR^e$, —$S(O)_nR^e$, —$S(O)_nNR^cR^d$, —$NR^c R^d$, —$C(O)R^e$, —$OC(O)R^e$, —$CO_2R^e$, —$CN$, —$C(O)NR^c R^d$, —$NR^cC(O)R^e$, —$NR^cC(O)OR^e$, —$NR^cC(O)NR^cR^d$, —$CF_3$, —$OCF_3$, and —$OCHF_2$, wherein each alkyl is unsubstituted or substituted with —$C_{1-6}$alkyl, halogen, —O—$C_{1-6}$alkyl and —$CF_3$. In another embodiment of the present invention, $R^a$ is selected from the group consisting of: —$C_{1-6}$alkyl, halogen, —$OR^e$, —$NR^cR^d$, —$CN$, —$CF_3$, —$OCF_3$, and —$OCHF_2$, wherein each alkyl is unsubstituted or substituted with —$C_{1-6}$alkyl, halogen, —O—$C_{1-6}$alkyl and —$CF_3$. In another embodiment of the present invention, $R^a$ is selected from the group consisting of: —$C_{1-6}$alkyl, and halogen, wherein each alkyl is unsubstituted or substituted with —$C_{1-6}$alkyl, halogen, —O—$C_{1-6}$alkyl and —$CF_3$. In another embodiment of the present invention, $R^a$ is —$C_{1-6}$alkyl, wherein each alkyl is unsubstituted or substituted with —$C_{1-6}$alkyl, halogen, —O—$C_{1-6}$alkyl and —$CF_3$. In another embodiment of the present invention, $R^a$ is halogen.

In another embodiment, $R^a$ is —$C_{1-6}$alkyl, wherein each alkyl is unsubstituted or substituted with —$C_{1-6}$alkyl, halogen, —O—$C_{1-6}$alkyl and —$CF_3$.

In another embodiment, $R^a$ is —$C_{1-6}$alkyl. In a class of this embodiment, $R^a$ is —$CH_3$.

In another embodiment of the present invention, $R^b$ is independently selected from the group consisting of: —$C_{1-10}$alkyl, —$C_{2-10}$alkenyl, —$CF_3$, halogen, —$CN$, —$OH$, —$OC_{1-10}$alkyl, —$OC_{2-10}$alkenyl, —$O(CH_2)_p OC_{1-10}$alkyl, —$O(CH_2)_p NR^cS(O)_mR^e$, —$O(CH_2)_pS(O)_mR^e$, —$O(CH_2)_pS(O)_mNR^cR^d$, —$O(CH_2)_pNR^cR^d$, —$C(O)R^e$, —$OC(O)R^e$, —$CO_2R^e$, —$C(O)NR^cR^d$, —$NR^cC(O)R^e$, —$NR^cC(O)OR^e$, —$NR^cC(O)NR^cR^d$, —$OCF_3$, and —$OCHF_2$, wherein each CH, $CH_2$, alkyl and alkenyl is unsubstituted or substituted with —$C_{1-6}$alkyl, halogen, —O—$C_{1-6}$alkyl and —$CF_3$.

In another embodiment of the present invention, $R^b$ is independently selected from the group consisting of: —$C_{1-10}$alkyl, —$C_{2-10}$alkenyl, —$CF_3$, halogen, —$CN$, —$OH$, —$OC_{1-10}$alkyl, —$OC_{2-10}$alkenyl, —$OCF_3$, and —$OCHF_2$, wherein each CH, alkyl and alkenyl is unsubstituted or substituted with —$C_{1-6}$alkyl, halogen, —O—$C_{1-6}$ alkyl and —$CF_3$.

In another embodiment of the present invention, $R^b$ is independently selected from the group consisting of: —$C_{1-10}$alkyl, —$CF_3$, halogen, —$CN$, —$OH$, —$OCF_3$, and —$OCHF_2$. In another embodiment of the present invention, $R^b$ is independently selected from the group consisting of: —$C_{1-10}$alkyl, —$CF_3$, halogen, —$OCF_3$ and —$OC_{1-10}$alkyl, wherein each alkyl is unsubstituted or substituted with —$C_{1-6}$alkyl, halogen, —O—$C_{1-6}$alkyl and —$CF_3$. In a class of this embodiment, each alkyl is unsubstituted or substituted with —$C_{1-6}$alkyl. In a subclass of this class, each alkyl is unsubstituted or substituted with —$CH_3$.

In another embodiment of the present invention, $R^b$ is independently selected from the group consisting of: —$C_{1-10}$alkyl, —$CF_3$, halogen, and —$OCF_3$, wherein each alkyl is unsubstituted or substituted with —$C_{1-6}$alkyl, halogen, —O—$C_{1-6}$alkyl and —$CF_3$. In a class of this embodiment of the present invention, $R^b$ is independently selected from the group consisting of: —$C_{1-10}$alkyl, —$CF_3$, halogen, and —$OCF_3$. In another class of this embodiment, $R^b$ is independently selected from the group consisting of: —$CH_3$, —$CF_3$, F, Cl and —$OCF_3$.

In another embodiment, $R^b$ is independently selected from the group consisting of: —$C_{1-10}$alkyl, —$CF_3$, halogen, and —$OCF_3$, wherein alkyl is unsubstituted or substituted with —$C_{1-6}$alkyl, halogen, —O—$C_{1-6}$alkyl and —$CF_3$. In another embodiment, $R^b$ is independently selected from the group consisting of: —$CH_3$, —$CF_3$, F, and —$OCF_3$.

In another embodiment of the present invention, $R^c$ and $R^d$ are each independently selected from the group consisting of: hydrogen, $C_{1-10}$alkyl, and $C_{2-10}$alkenyl, wherein each alkyl and alkenyl is unsubstituted or substituted with one to three substituents independently selected from $R^f$. In another embodiment of the present invention, $R^c$ and $R^d$ are each independently selected from the group consisting of hydrogen and $C_{1-10}$alkyl, wherein each alkyl and alkenyl is unsubstituted or substituted with one to three substituents independently selected from $R^f$. In another embodiment of the present invention, $R^c$ and $R^d$ are each —$C_{1-10}$alkyl, wherein each alkyl and alkenyl is unsubstituted or substituted with one to three substituents independently selected from $R^f$. In another embodiment of the present invention, $R^c$ and $R^d$ are each hydrogen.

In another embodiment of the present invention, $R^c$ is independently selected from the group consisting of: hydrogen, $C_{1-10}$alkyl, and $C_{2-10}$alkenyl, wherein each alkyl and alkenyl is unsubstituted or substituted with one to three substituents independently selected from $R^f$. In another embodiment of the present invention, $R^c$ is independently selected from the group consisting of: hydrogen and $C_{1-10}$alkyl, wherein each alkyl and alkenyl is unsubstituted or substituted with one to three substituents independently selected from $R^f$. In another embodiment of the present invention, $R^c$ is —$C_{1-10}$alkyl, wherein each alkyl and alkenyl is unsubstituted or substituted with one to three substituents independently selected from $R^f$. In another embodiment of the present invention, $R^c$ is hydrogen.

In another embodiment of the present invention, $R^d$ is independently selected from the group consisting of: hydrogen, $C_{1-10}$alkyl, and $C_{2-10}$alkenyl, wherein each alkyl and alkenyl is unsubstituted or substituted with one to three substituents independently selected from $R^f$. In another embodiment of the present invention, $R^d$ is independently selected from the group consisting of: hydrogen and $C_{1-10}$alkyl, wherein each alkyl and alkenyl is unsubstituted or substituted with one to three substituents independently selected from $R^f$. In another embodiment of the present invention, $R^d$ is —$C_{1-10}$alkyl, wherein each alkyl and alkenyl is unsubstituted or substituted with one to three substituents independently selected from $R^f$. In another embodiment of the present invention, $R^d$ is hydrogen.

In another embodiment of the present invention, each $R^e$ is independently selected from the group consisting of: hydrogen, —$C_{1-10}$alkyl and —$C_{2-10}$ alkenyl, wherein each alkyl, and alkenyl is unsubstituted or substituted with one to three substituents selected from $R^h$. In another embodiment of the present invention, each $R^e$ is independently selected from the group consisting of: hydrogen, and —$C_{1-10}$alkyl, wherein each alkyl is unsubstituted or substituted with one to three substituents selected from $R^h$. In another embodiment, each $R^e$ is —$C_{1-10}$alkyl-, wherein each alkyl is unsubstituted or substituted with one to three substituents selected from $R^h$. In a class of this embodiment, each $R^e$ is —$CH_3$.

In another embodiment of the present invention, each $R^e$ is hydrogen.

In another embodiment of the present invention, each $R^f$ is selected from the group consisting of: halogen, $C_{1-10}$alkyl, —OH, —O—$C_{1-4}$alkyl, —CN, —$CF_3$, —$OCHF_2$ and —$OCF_3$, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen, $C_{1-10}$alkyl and —OH, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen and $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^f$ is $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a subclass of this class, each $R^f$ is selected from the group consisting of: $C_{1-10}$alkyl. In another class of this embodiment, each $R^f$ is halogen.

In another embodiment of the present invention, each $R^g$ is selected from the group consisting of: hydrogen and —$C_{1-10}$alkyl, wherein each alkyl is unsubstituted or substituted with one to five halogens. In another embodiment of the present invention, each $R^g$ is selected from the group consisting of: —$C_{1-10}$alkyl, wherein each alkyl is unsubstituted or substituted with one to five halogens. In another embodiment of the present invention, each $R^g$ is selected from the group consisting of: —$C_{1-10}$alkyl. In another embodiment of the present invention, each $R^g$ is hydrogen.

In another embodiment of the present invention, each $R^h$ is selected from the group consisting of: halogen, $C_{1-10}$alkyl and —OH, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^h$ is selected from the group consisting of: halogen and $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^h$ is selected from the group consisting of: $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In another class of this embodiment, each $R^h$ is halogen.

In another embodiment of the present invention, $R^1$ is independently selected from the group consisting of: —$C_{1-6}$alkyl, —$OR^e$, —$NR^cS(O)_mR^e$, halogen, —$S(O)_mR^e$, —$S(O)_m$ $NR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$ and —$OCHF_2$. In another embodiment of the present invention, $R^1$ is independently selected from the group consisting of: —$C_{1-6}$alkyl, —$OR^e$, —$NR^cS(O)_mR^e$, halogen, —$NR^cR^d$, —$C(O)R^e$, —$OC(O)R^e$, —$CO_2R^e$, —CN, —$CF_3$, —$OCF_3$ and —$OCHF_2$. In another embodiment of the present invention, $R^1$ is independently selected from the group consisting of: —$C_{1-6}$alkyl, —$OR^e$, and halogen. In another embodiment of the present invention, $R^1$ is independently selected from the group consisting of: —$C_{1-6}$alkyl and halogen. In another embodiment of the present invention, $R^1$ is —$C_{1-6}$alkyl. In another embodiment of the present invention, $R^1$ is halogen.

In another embodiment of the present invention, $R^j$ is independently selected from the group consisting of: —$C_{1-6}$alkyl, —$OR^e$, —$NR^cS(O)_mR^e$, halogen, —$S(O)_mR^e$, —$S(O)_m$ $NR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$ and —$OCHF_2$. In another embodiment of the present invention, $R^j$ is independently selected from the group consisting of: —$C_{1-6}$alkyl, —$OR^e$, halogen, —$NR^cR^d$, —$C(O)R^e$, —$OC(O)R^e$, —$CO_2R^e$, —CN, —$CF_3$, —$OCF_3$, and —$OCHF_2$. In another embodiment of the present invention, $R^j$ is independently selected from the group consisting of: —$C_{1-6}$alkyl, —$OR^e$, and halogen. In another embodiment of the present invention, $R^j$ is independently selected from the group consisting of: —$C_{1-6}$alkyl and halogen. In another embodiment of the present invention, $R^j$ is —$C_{1-6}$alkyl. In another embodiment of the present invention, $R^j$ is halogen.

In another embodiment of the present invention, each $R^k$ is independently selected from the group consisting of: hydrogen, —$C_{1-6}$ alkyl, —$CF_3$ and —$CHF_2$, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is independently selected from the group consisting of: hydrogen and —$C_{1-6}$ alkyl, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is independently selected from the group consisting of: —$C_{1-6}$ alkyl, wherein each alkyl is unsubstituted or substituted with one to three substituents independently selected from: —OH, —$OC_{1-6}$alkyl, halogen, cyano, and —$S(O)_2C_{1-6}$ alkyl. In a class of this embodiment, each $R^k$ is independently selected from the group consisting of: —$C_{1-6}$alkyl.

In another embodiment of the present invention, each $R^k$ is hydrogen.

In another embodiment of the present invention, each $R^L$ is independently selected from the group consisting of: —$C_{1-10}$alkyl, —$C_{2-10}$ alkenyl, —$C_{2-10}$alkynyl, and —$C_{3-6}$cycloalkyl, wherein each alkyl, alkenyl, alkynyl, and cycloalkyl is unsubstituted or substituted with 1-4 substituents selected from $C_{1-6}$alkyl, halogen, and —$OC_{1-6}$alkyl.

In another embodiment of the present invention, each $R^L$ is independently selected from the group consisting of: —$C_{1-10}$alkyl and —$C_{3-6}$cycloalkyl, wherein each alkyl and cycloalkyl is unsubstituted or substituted with 1-4 substituents selected from $C_{1-6}$alkyl, halogen, and —$OC_{1-6}$alkyl.

In another embodiment of the present invention, each $R^L$ is independently selected from the group consisting of: —$C_{1-10}$alkyl and —$C_{3-6}$cycloalkyl. In a class of this embodiment, each $R^L$ is independently selected from the group consisting of: —$CH_3$ and cyclopropyl.

In another embodiment of the present invention, $R^L$ is —$C_{1-10}$alkyl. In a class of this embodiment, each $R^L$ is —$CH_3$.

In another embodiment of the present invention, $R^L$ is —$C_{3-6}$cycloalkyl. In a class of this embodiment, $R^L$ is cyclopropyl.

In another embodiment of the present invention, each $R^m$ is independently selected from the group consisting of: —$C_{1-10}$alkyl, —$C_{2-10}$ alkenyl, —$C_{3-6}$ cycloalkyl, —$C_{2-5}$cycloheteroalkyl, aryl and heteroaryl. In another embodiment of the present invention, each $R'''$ is independently selected from the group consisting of: —$C_{1-10}$alkyl and —$C_{2-10}$alkenyl. In another embodiment of the present invention, each $R'''$ is independently selected from the group consisting of: —$C_{1-10}$alkyl.

In another embodiment of the present invention, $R''$ is selected from the group consisting of: hydrogen, and —$C_{1-10}$alkyl, wherein each alkyl is unsubstituted or substituted with one to five halogens. In a class of this embodiment, $R''$ is selected from the group consisting of: hydrogen and —$CH_3$. In another class of this embodiment, $R''$ is hydrogen. In another class of this embodiment, $R''$ is —$CH_3$.

In another embodiment, $R''$ is —$C_{1-10}$alkyl, wherein each alkyl is unsubstituted or substituted with one to five halogens. In a class of this embodiment, $R''$ is —$CH_3$.

In another embodiment of the present invention, n is 0, 1 or 2. In a class of this embodiment, n is 0 or 1. In another class of this embodiment, n is 1 or 2. In another class of this embodiment, n is 0. In another class of this embodiment, n is 1. In another class of this embodiment, n is 2.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, each p is independently selected from: 0, 1, 2, 3, 4, 5 or 6. In another embodiment of the present invention, p is 0, 1, 2, 3 or 4. In a class of this embodiment, p is 0, 1, 2 or 3. In a class of this embodiment, p is 0, 1 or 2. In another embodiment of the present invention, p is 1, 2, 3 or 4. In a class of this embodiment, p is 1, 2 or 3. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6.

In another embodiment of the present invention, the invention relates to compounds of structural formula Ia:

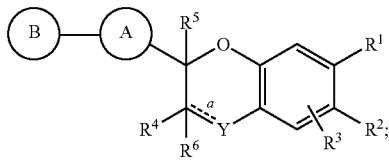

Ia or a pharmaceutically acceptable salt thereof.

In another embodiment of the present invention, the invention relates to compounds of structural formula Ib:

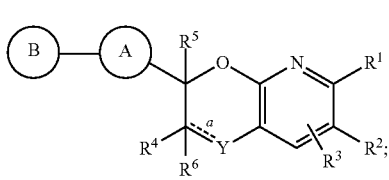

Ib or a pharmaceutically acceptable salt thereof.

In another embodiment of the present invention, the invention relates to compounds of structural formula Ic:

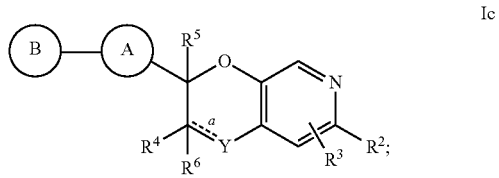

Ic or a pharmaceutically acceptable salt thereof.

In another embodiment of the present invention, the invention relates to compounds of structural formula Id:

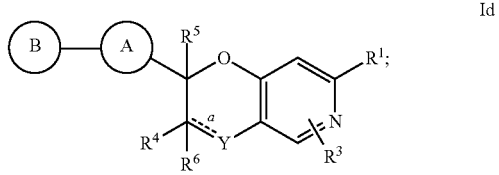

Id or a pharmaceutically acceptable salt thereof.

In another embodiment of the present invention, the invention relates to compounds of structural formula Ie:

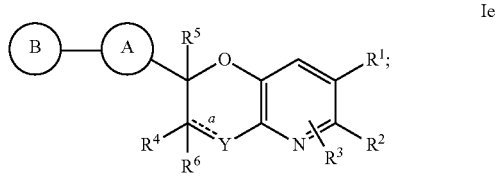

Ie or a pharmaceutically acceptable salt thereof.

In another embodiment of the present invention, the invention relates to compounds of structural formula If:

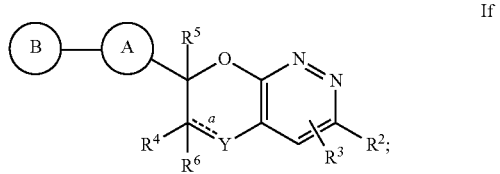

If or a pharmaceutically acceptable salt thereof.

In another embodiment of the present invention, the invention relates to compounds of structural formula Ig:

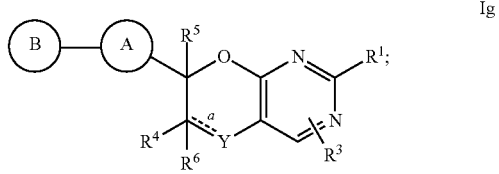

Ig or a pharmaceutically acceptable salt thereof.

In another embodiment of the present invention, the invention relates to compounds of structural formula Ih:

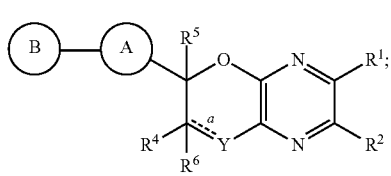

or a pharmaceutically acceptable salt thereof.

In another embodiment of the present invention, the invention relates to compounds of structural formula Ii:

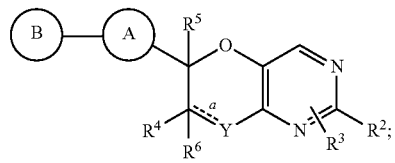

or a pharmaceutically acceptable salt thereof.

In another embodiment of the present invention, the invention relates to compounds of structural formula Ij:

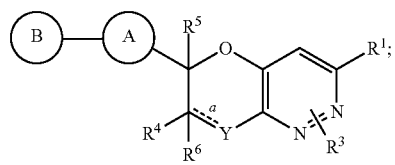

or a pharmaceutically acceptable salt thereof.

In another embodiment of the present invention, the invention relates to compounds of structural formula Ik:

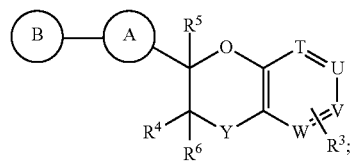

or a pharmaceutically acceptable salt thereof.

In another embodiment of the present invention, the invention relates to compounds of structural formula Il:

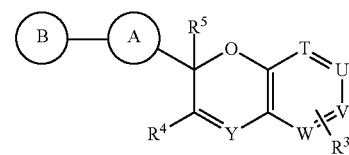

or a pharmaceutically acceptable salt thereof.

In another embodiment of the present invention, the invention relates to compounds of structural formula Im:

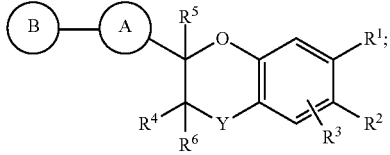

or a pharmaceutically acceptable salt thereof.

In another embodiment of the present invention, the invention relates to compounds of structural formula In:

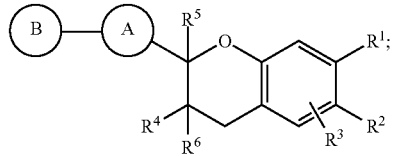

or a pharmaceutically acceptable salt thereof.

The compound of structural formula I includes the compounds of structural formulas Ia, Ib, Ic, Id, Ie, If, Ig, Ih, Ii, Ij, Ik, Il, Im and In, and pharmaceutically acceptable salts, hydrates and solvates thereof.

Another embodiment of the present invention relates to compounds of structural formula Ik:

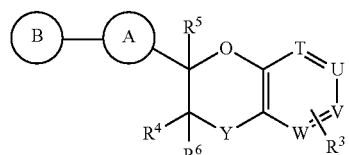

wherein
T is CH;
U is $CR^1$;
V is $CR^2$;
W is CH;
Y is selected from the group consisting of: —$CR^gR^g$;
A is selected from the group consisting of:
  (1) —$C_{1-6}$alkyl-N($R^n$)—,
  (2) —$C_{1-6}$alkyl-$C_{6-14}$cycloheteroalkyl, and
  (3) —$C_{6-14}$cycloheteroalkyl,
wherein A is unsubstituted or substituted with one to five substituents selected from $R^a$;
B is selected from the group consisting of:
  (1) aryl-$C_{1-10}$ alkyl-, and
  (2) heteroaryl,
wherein B is unsubstituted or substituted with one to five substituents selected from $R^b$;
$R^1$ and $R^2$ are each independently selected from:
  (1) hydrogen, and
  (2) —$C_{1-6}$alkyl,
wherein each alkyl is unsubstituted or substituted with one to three substituents selected from $R^L$, and wherein one of $R^1$ and $R^2$ is $C_{1-6}$alkyl, wherein —$C_{1-6}$alkyl is substituted with a substituent selected from $R^7$;
$R^3$ is hydrogen;
$R^4$ is hydrogen;
$R^5$ is hydrogen;

$R^6$ is hydrogen;
$R^7$ is —$CO_2R^8$;
$R^8$ is hydrogen;
or a pharmaceutically acceptable salt thereof.

Another embodiment of the present invention relates to compounds of structural formula Ik:

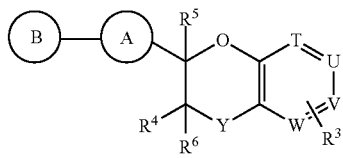

Ik wherein
T is CH;
U is $CR^1$;
V is $CR^2$;
W is CH;
Y is —$CH_2$;
A is selected from the group consisting of:
(1) —$C_{1-6}$alkyl-N(R'')—, and
(2) —$C_{6-14}$cycloheteroalkyl,
wherein A is unsubstituted or substituted with one to five substituents selected from $R^a$;
B is aryl-$C_{1-10}$ alkyl-, wherein B is unsubstituted or substituted with one to five substituents selected from $R^b$;
$R^1$ is selected from —$C_{1-6}$alkyl, wherein each alkyl is unsubstituted or substituted with one to three substituents selected from $R^L$, and wherein $R^1$ is substituted with a substituent selected from $R^7$;
$R^2$ is hydrogen;
$R^3$ is hydrogen;
$R^4$ is hydrogen;
$R^5$ is hydrogen;
$R^6$ is hydrogen;
$R^7$ is —$CO_2R^8$;
$R^8$ is hydrogen;
or a pharmaceutically acceptable salt thereof.

Illustrative, but non-limiting, examples of the compounds of the present invention that are useful as agonists of G-protein-coupled receptor 40 (GPR40) are the following compounds:

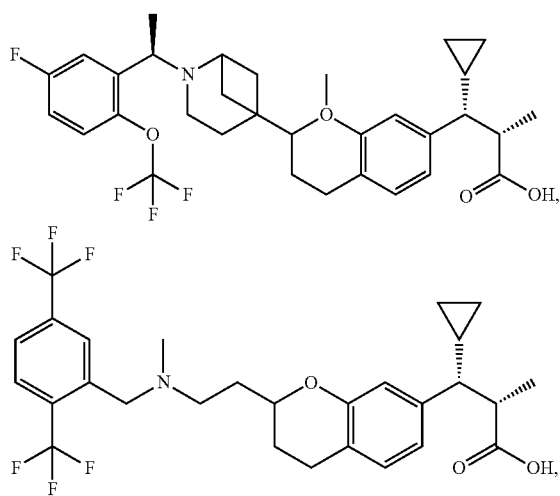

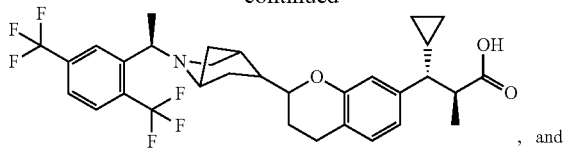

, and

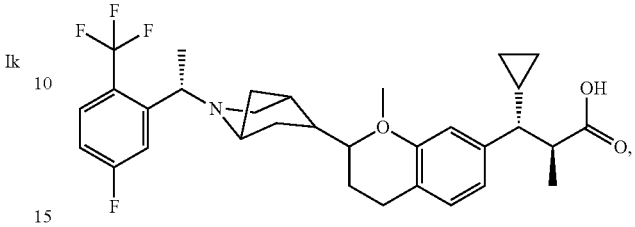

and pharmaceutically acceptable salts thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is 2-methyl-1-propenyl.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like. In one embodiment, alkynyl is —$C_2$alkyne-$CH_3$.

"Cycloalkyl" means a saturated monocyclic, bicyclic, tricyclic, fused, spirocyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from:

cyclopropane, cyclobutane and cyclohexane. In another embodiment of the present invention, cycloalkyl is selected from: cyclopropane.

"Cycloalkenyl" means a nonaromatic monocyclic, bicyclic, tricyclic, fused, spirocyclic or bridged carbocyclic ring containing at least one double bond. Examples of cycloalkenyl include cyclopropenyl, cyclobutenyl, cyclopentenyl, cyclohexenyl, cycloheptenyl, cyclooxtenyl and the like. In one embodiment of the present invention, cycloalkenyl is cyclopentenyl. "Cycloheteroalkyl" means a saturated or partly unsaturated non-aromatic monocyclic, bicyclic, tricyclic, fused, spirocyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran. In one embodiment of the present invention, cycloheteroalkyl is selected from: piperidine, 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane. In another embodiment of the present invention, cycloheteroalkyl is piperidine. In another embodiment of the present invention, cycloheteroalkyl is selected from: 2-azaspiro[3.3]heptane, 3-oxa-7-azabicyclo[3.3.1]nonane, 8-azabicyclo[3.2.1]octane, 2-aza-bicyclo-[2.2.1]heptane, 3-azabicyclo[3.2.1]octane, 9-azabicyclo[3.3.1]nonane, and 2-azabicyclo[3.1.1]heptane.

"Cycloheteroalkenyl" means a non-aromatic monocyclic, bicyclic, tricyclic, fused, spirocyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), fuoro(2,3-b)pyridyl, quinolyl, indolyl, isoquinolyl, quinazolinyl, dibenzofuranyl, and the like. In one embodiment of the present invention, heteroaryl is selected from: pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

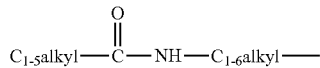

For example, —$NR^cC(O)R^e$ is equivalent to —$N(R^c)C(O)R^e$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

The present invention includes the pharmaceutically acceptable salts of the compounds of formula I, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:
(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapo-B liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:
(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The chroman compounds of the present invention have the unexpected benefit of increased potency in the FLIPR Assay (see Biological Assays) compared to the corresponding compounds in which the chroman core is replaced with a 2,3,4,5-tetrahydrobenzo[b]oxepine core or a 2,3-dihydrobenzofuran core.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated ($\geq 140$ mmHg/$\geq 90$ mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e., cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dyslipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.
Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, $C_7$, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATI-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl) phenyl)-methoxy)phenyl)iso, 5-(4-((3-(2-methyl-6-(3-hydroxypropoxy)pyridine-3-yl)-2-methylphenyl)methoxy) phenyl)-isothiazole-3-ol 1-oxide, and 5-[4-[[3-[4-(3-aminopropoxy)-2,6-dimethylphenyl]phenyl]-methoxy] phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC591, SC795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, and the like; (29) IBAT inhibitors such as BARI143/HMR145A/HMR1453 (Sanofi-Aventis), PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, bamidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (*Vernalis*), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552, 524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vemalis/Roche) YM 348; and those disclosed in U.S. Pat. No. 3,914,250; and PCT Publications 01/66,548, 02/36,596, 02/48,124, 02/10,169, 02/44,152; 02/51,844, 02/40,456, 02/40,457, 03/057,698, 05/000,849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436, 272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) 03 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone 3 agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 113 HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11, 12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) McSr (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-diabetic compounds, anti-obesity compounds and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

List of Abbreviations

Ac is acetyl; AcCN is acetonitrile; AcO is acetoxy; Alk is alkyl; anh. is anhydrous; APCI is atmospheric pressure chemical ionization; aq or aq. is aqueous; Ar is aryl; atm is atmosphere; $BH_3DMS$ is borane dimethyl sulfide complex; Boc is tert-butoxycarbonyl; Bn-O is phenyl-$CH_2$—O or benzyloxy; Br is broad; BrettPhos palladacycle precatalyst is Brettphos Pd G1 precatalyst (Aldrich); n-BuLi is n-butyl lithium; $Bu_3P$ is tributylphosphine; t-BuOK is potassium tert-butoxide; C—C refers to a carbon-carbon bond cross coupling reaction; C—N refers to a carbon-nitrogen bond cross coupling reaction; ° C. is degrees celsius; Cataxium precatalyst or Cataxium Pd precat or precatalyst is cataCXium A Pd G3 (Aldrich); Cbz is benzyloxycarbonyl; $CH_2Cl_2$ is dichloromethane; conc or conc. is concentrated; CV is column volumes; d is doublet; DAST is (diethylamino)sulfur trifluoride; DIBAL-H ix diisobutylaluminum hydride; DIAD is diisopropyl azodicarboxylate; DCM is dichloromethane; DEA is diethyl amine; DIPEA is N,N-diisopropylethylamine; DIPA is diisopropyl amine; DMAP is 4-dimethylaminopyridine; DMF is N,N-dimethylformamide; DMP is Dess-Martin periodinane; DMS is dimethyl sulfide; DMSO is dimethylsulfoxide; dppf is 1,1'-Bis(diphenyl-phosphino)ferrocene; ESI is electrospray ionization; EA or EtOAc is ethyl acetate; Et is ethyl; $Et_2O$ is diethyl ether; EtMgBr is ethyl magnesium bromide; EtOH is ethanol; g is gram(s); h or hr or hrs is hour(s); hex is hexanes; HPLC is high pressure liquid chromatography; HOAc or AcOH is acetic acid; kg is kilogram(s); IPA is isopropanol; KOH ispotassium hydroxide; KOAc is potassium acetate; KOtBu is potassium tert-butoxide; L is liter; LAH is lithium aluminum hydride; LC-M is molar; MS is liquid chromatography-mass spectroscopy; LDA is lithium diisopropyl amide; LiOH is lithium hydroxide; m is multiplet; Me is methyl; MeCN is acetonitrile; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeMgBr is methyl magnesium bromide; MeOH is methyl alcohol or methanol; $MgSO_4$ is magnesium sulfate; MPLC is medium pressure liquid chromatography; MS is mass spectroscopy; MsCl or Ms-Cl is methane sulfonyl chloride; MeCN is acetonitrile; MeI is methyl iodide; MsCl is methane sulfonyl chloride; MTBE is methyl tert-butyl ether; N is normal; $Na(AcO)_3BH$ is sodium triacetoxy borohydride; NaHMDS is sodium hexamethyl disilazide; NaOH is sodium hydroxide; $Na_2SO_4$ is sodium sulfate; $NH_4OAc$ is ammonium acetate; NBS is N-bromo succinamide; $NEt_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; paraform is paraform-aldehyde; PE is petroleum ether; PG is protecting group; i-PrOH is isopropanol; $P(Cy)_3$ is tricyclohexyl phosphine; $Pd_2(dba)_3$ is tris(dibenzylidene-acetone)-dipalladium (0); $Pd(OAc)_2$ is palladium acetate; $Pd[P(t-Bu)_3]_2$ is bis(tri-tert-butylphosphine)palladium (0); $Pd(dppf)Cl_2$ is [1,1'-bis(diphenylphosphino)-ferrocene]dichloro-palladium (II); $PdCl_2(dppf)_2CH_2Cl_2$ is [1,1'-Bis(diphenylphosphino)-ferrocene]dichloropalladium(II), complex with dichloromethane (Aldrich); $Pd(PPh_3)_4$ is tetrakis or tetrakis(triphenylphosphine)palladium (0); $PPh_3$ is triphenyl phosphine; $Pd(t-Bu_2P)_2FerrCl_2$ is bis-tri-tert-butylphosphino ferrocene dichloro palladium (II); PMB is para-methoxybenzyl; PMBCl is para-methoxybenzyl chloride; precat is precatalyst; prep is preparative; prep. TLC or prep-TLC, or prep TCL is preparative thin layer chromatography; rbf or RBF is round bottom flask; RCM is ring closing metathesis reaction; rt or r.t. or RT isroom temperature; RuCl[(R,R)-TSDPEN](mesitylene) is [N-[(1R,2R)-2-(Amino-κN)-1,2-diphenylethyl]-4-methylbenzenesulfonamidato-κN]chloro[(1,2,3,4,5,6-η)-1,3,5-trimethylbenzene]-ruthenium; Ru-Josiphos is generated using (Me-allyl)₂Ru(COD) (Aldrich) and Josiphos SL-J502-2 (Aldrich); R_f is retention factor; s is singlet; sat or sat. is saturated; SEM is trimethylsilyl ethoxy methyl, SEMCl is trimethylsilyl ethoxy methyl chloride; SFC is supercritical fluid chromatography; S-Phos is 2-dicyclohexylphosphino-2',6'-dimethoxy-biphenyl; S-Phos(Pd) is chloro(2-dicyclohexylphosphino-2',6'-dimethoxy-1,1'-biphenyl)[2-(2-aminoethylphenyl)]palladium(II) [CAS-No. 1028206-58-7]; S-Phos precatalyst is S-Phos Pd G2 precatalyst-Aldrich; S-Phos second generation precatalyst is Chloro(2-dicyclohexyl-phosphino-2',6'-dimethoxy-1,1'-biphenyl)[2-(2'-amino-1,1'-biphenyl)]palladium-(II), SPhos-Pd-G2) [CAS-No. 1375325-64-6]; t is triplet; TBAF is tetrabutylammonium fluoride; TBSCl is tert-butyl dimethylsilyl chloride; TBTU is N,N,N',N'-Tetramethyl-O-(benzotriazol-1-yl)uronium tetrafluoroborate; TEA is triethyl amine; Tf is trifluoromethane sulfonyl; THF is tetrahydrofuran; Ti(OiPr)₄ is titanium isopropoxide; TFA is trifluoroacetic acid; TLC is thin-layer chromatography; Trixiephos is racemic-2-di-I-butylphosphino-1,1'-binaphthyl; TosCl and TsCl is p-toluene sulfonyl chloride; pTSA, pTsOH and TsOH is p-toluenesulfonic acid, Ts₂O is tosic anhydride orp-toluene sulfonic anhydride; and xphos is 2-dicyclohexylphosphino-2',4',6'-triisopropyl-biphenyl.

Several methods for preparing the compounds of this invention are illustrated in the following Schemes, Intermediates and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided for the purpose of illustration only and are not to be construed as limitations on the disclosed invention. All temperatures are degrees Celsius unless otherwise noted.

SCHEME 1

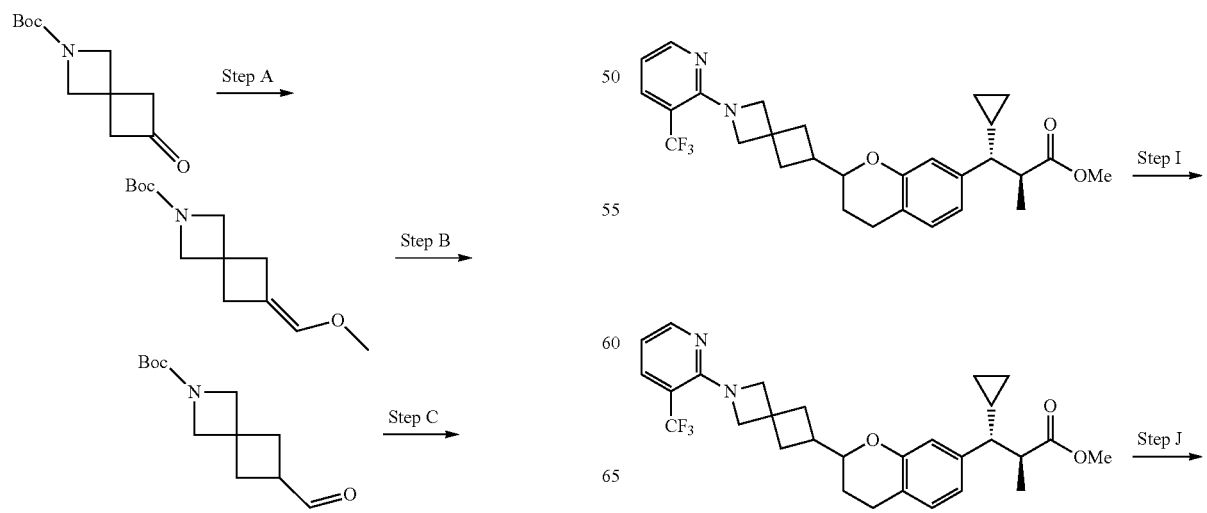

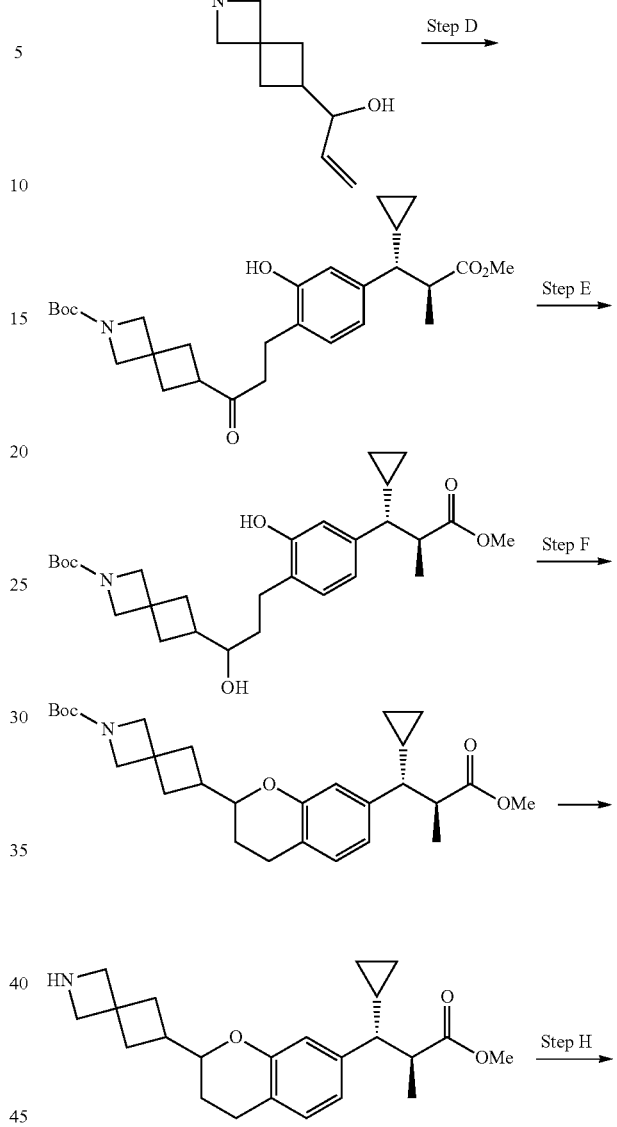

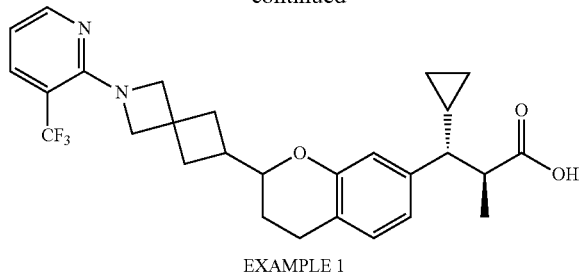

EXAMPLE 1

Example 1

(2S,3R)-3-cyclopropyl-2-methyl-3-((R or S)-2-(2-(3-(trifluoro-methyl)pyridin-2-yl)-2-azaspiro[3.3]heptan-6-yl)chroman-7-yl)propanoic Acid

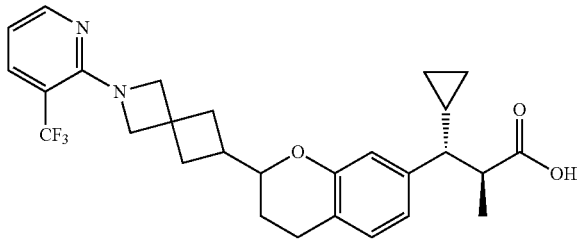 [SMILES: C[C@H](C(=O)O)[C@H](c1ccc2c(c1)OC(C1CC3(C1)CN(c1ncccc1C(F)(F)F)C3)CC2)C1CC1]

Step A: tert-butyl 6-(methoymethylene)-2-azaspiro[3.3]heptane-2-carboxylate

To a solution of (methoxymethyl)triphenylphosphonium chloride (2.92 g, 8.52 mmol) in THF (20 mL) was added dropwise LDA (4.47 ml, 8.95 mmol, 1.0 M in THF) over 20 min under $N_2$ at 0° C. The reaction mixture was stirred at room temperature for 2 h. Then a solution of tert-butyl 6-oxo-2-azaspiro[3.3]heptane-2-carboxylate (900 mg, 4.26 mmol) in THF (10 mL) was added dropwise to the mixture. The reaction mixture was stirred at 60° C. for 3 h, then quenched with water (30 mL) and extracted with ethyl acetate (20 mL×3). The combined organic layers were washed with water (40 mL) and brine (40 mL), dried over anhydrous $MgSO_4$ and filtered. The filtrate was concentrated under reduced pressure. The resulting residue was purified by column chromatography on silica gel eluted with PE/EtOAc (50:1-20:1, v/v) to give the title compound. $^1$H NMR (400 MHz, CDCl3): δ=5.81 (s, 1H), 3.93 (s, 4H), 3.56 (s, 3H), 2.87 (s, 2H), 2.79 (s, 2H), 1.44 (s, 12H).

Step B: tert-butyl 6-formyl-2-azaspiro[3.3]heptane-2-carboxylate

To a solution of tert-butyl 6-(methoxymethylene)-2-azaspiro[3.3]heptane-2-carboxylate (850 mg, 3.55 mmol) in DCM (8.0 mL) and $H_2O$ (4.0 mL) was added trichloroacetic acid (2.32 g, 14.2 mmol) under nitrogen. The reaction mixture was stirred at room temperature (20° C.) for 1 h, then quenched with water (5.0 mL) and was extracted with DCM (5.0 mL×3). The combined organic layers were washed by brine (10 mL), dried over anhydrous $MgSO_4$ and filtered. The filtrate was concentrated under reduced pressure. The resulting residue was purified by preparative HPLC (preparative HPLC on a GILSON 281 instrument fitted with YMC-Actus Triart C18 150*30 mm*5 m, mobile phase A: water (containing 0.1% TFA, v/v), mobile phase B: acetonitrile; gradient: 25-55% B, 0-10 min; 100% B, 10.5-12.5 min; 5% B, 13-15 min) to give the title compound. $^1$H NMR (400 MHz, CDCl3): δ=9.72 (s, 1H), 3.95 (s, 2H), 3.90 (s, 2H), 3.13-3.06 (m, 1H), 2.46-2.33 (m, 4H), 1.43 (s, 12H).

Step C: tert-butyl 6-(1-hydroxyallyl)-2-azaspiro[3.3]heptane-2-carboxylate

To a solution of tert-butyl 6-formyl-2-azaspiro[3.3]heptane-2-carboxylate (550 mg, 2.44 mmol) in THF (10.0 mL) was added dropwise vinylmagnesium bromide (4.88 ml, 4.88 mmol, 1M in THF) over 10 min at 0° C. under nitrogen atmosphere. The reaction mixture was stirred at 0° C. for 30 min, then was warmed to room temperature (25° C.) and stirred for 30 min. The reaction mixture was quenched with saturated aqueous solution of $NH_4Cl$ (10 mL) and extracted with EtOAc (10 mL×2). The combined organic layers were washed with brine (15 mL), dried over anhydrous $Na_2SO_4$ and filtered. The filtrate was concentrated in vacuo to afford the title compound, which was used directly for the next step.

Step D: tert-butyl 6-(3-(4-((1R,2S)-1-cyclopropyl-3-methoxy-2-methyl-3-oxopropyl)-2-hydroxyphenyl)propanoyl)-2-azaspiro[3.3]heptane-2-carboxylate To a solution of tert-butyl 6-(1-hydroxyallyl)-2-azaspiro[3.3]heptane-2-carboxylate (480 mg, 1.90 mmol) and (2S,3R)-methyl 3-cyclopropyl-3-(3-hydroxy-4-iodophenyl)-2-methylpropanoate (350 mg, 0.972 mmol) in toluene (8.0 mL) were added N-cyclohexyl-N-methylcyclohexanamine (380 mg, 1.94 mmol) and chloro(2-di-t-butylphosphino-2',4',6'-tri-i-propyl-1,1'-biphenyl)-palladium(II) (66.9 mg, 0.0972 mmol) under nitrogen atmosphere. The reaction mixture was stirred at 100° C. for 2 h, then water (5.0 mL) was added to the mixture. The aqueous phase was separated and extracted with EtOAc (5 mL×3). The combined organic layers were washed with water (5.0 mL) and brine (5.0 mL), dried over anhydrous $MgSO_4$ and filtered. The filtrate was concentrated under reduced pressure. The resulting residue was purified by preparative TLC (PE:EtOAc=2:1, v/v) to give the title compound. MS (ESI) m/z: 486.3 [M+H]$^+$ Step E: tert-butyl 6-(3-(4-((1R,2S)-1-cyclopropyl-3-methoxy-2-methyl-3-oxopropyl)-2-hydroxyphenyl)-1-hydroxypropyl)-2-azaspiro[3.3]heptane-2-carboxylate To a solution of tert-butyl 6-(3-(4-((1R,2S)-1-cyclopropyl-3-methoxy-2-methyl-3-oxopropyl)-2-hydroxy-phenyl)propanoyl)-2-azaspiro[3.3]heptane-2-carboxylate (320 mg, 0.659 mmol) in EtOH (5.0 ml) was added $NaBH_4$ (49.9 mg, 1.32 mmol) in portions at 0° C. The reaction mixture was stirred at 0° C. for 1 h, and then quenched with water (10 mL) at 0° C. The aqueous phase was separated, and extracted with EtOAc (10 mL×3). The combined organic layers were washed with water (20 mL) and brine (20 mL), dried over anhydrous $MgSO_4$ and filtered. The filtrate was concentrated under reduced pressure. The resulting residue was purified by preparative TLC (PE:EtOAc=3:2, v/v) to give the title compound. MS (ESI) m/z: 488.3 [M+H]$^+$ $^1$H NMR (400 MHz, CDCl$_3$): δ=7.01 (d, J=7.6 Hz, 1H), 6.66 (d, J=8.0 Hz, 1H), 6.64 (s, 1H), 3.92 (s, 2H), 3.79-3.73 (m, 5H), 3.45-3.40 (m, 1H), 2.85-2.61 (m, 2H), 2.20-2.11 (m, 3H), 1.89-1.82 (m, 1H), 1.66-1.60 (m, 2H), 1.42 (s, 9H), 1.04-1.01 (m, 1H), 0.95 (d, J=6.4 Hz, 1H), 0.57-0.51 (m, 1H), 0.34-0.20 (m, 2H), 0.02-0.04 (m, 1H).

Step F: tert-butyl 6-((RS)-7-((1R,2S)-1-cyclopropyl-3-methoxy-2-methyl-3-oxopropyl) chroman-2-yl)-2-azaspiro[3.3]heptane-2-carboxylate To a solution of tert-butyl 6-(3-(4-((1R,2S)-1-cyclopropyl-3-methoxy-2-methyl-3-oxopropyl)-2-hydroxyphenyl)-1-hydroxy-propyl)-2-azaspiro[3.3]heptane-2-carboxylate (290 mg, 0.595 mmol) in DCM (6.0 mL) was added triphenylphosphine (234 mg, 0.892 mmol) under nitrogen. The reaction was cooled to 0° C., then DIAD (0.231 ml, 1.19 mmol) was added dropwise over 2 min, and the mixture was stirred at room temperature (15° C.) for 2 h. Then the reaction mixture was quenched with water (5.0 mL) and was extracted with DCM (5.0 mL×2). Then the combined organic layers were washed with brine (10 mL), dried over anhydrous MgSO$_4$ and filtered. The filtrate was concentrated in vacuo to obtain the title compound, which was used directly for the next step. MS (ESI) m/z: 470.3 [M+H]$^+$

Step G: (2S,3R)-methyl 3-((RS)-2-(2-azaspiro[3.3]heptan-6-yl)chroman-7-yl)-3-cyclopropyl-2-methyl-propanoate To a solution of tert-butyl 6-((RS)-7-((1R,2S)-1-cyclopropyl-3-methoxy-2-methyl-3-oxopropyl)chroman-2-yl)-2-azaspiro[3.3]heptane-2-carboxylate (80.0 mg, 0.170 mmol) in DCM (2.0 mL) was added TFA (0.262 mL, 3.41 mmol) at 20° C. under nitrogen. The reaction was stirred at 20° C. for 1 h, and then was concentrated under reduced pressure to give the title compound, which was used directly for the next step without further purification. MS (ESI) m/z: 370.3 [M+H]$^+$

Step H: (2S,3R)-methyl 3-cyclopropyl-2-methyl-3-((RS)-2-(2-(3-(trifluoromethyl)pyridin-2-yl)-2-azaspiro[3.3]heptan-6-yl)chroman-7-yl)propanoate To a solution of (2S,3R)-methyl-3-((RS)-2-(2-azaspiro[3.3]heptan-6-yl)chroman-7-yl)-3-cyclopropyl-2-methyl-propanoate (55.0 mg, 0.149 mmol) and 2-bromo-3-(trifluoromethyl)pyridine (50.5 mg, 0.223 mmol) in DMF (2.0 mL) was added TEA (45.2 mg, 0.447 mmol) under nitrogen. The reaction mixture was stirred at 100° C. for 3 h. Then the reaction was cooled to room temperature, and water (10 mL) was added. The resulting mixture was extracted with EtOAc (5 mL×2). The combined organic layers were washed with brine (10 mL), dried over anhydrous Na$_2$SO$_4$ and filtered. The filtrate was concentrated in vacuo to afford the title compound, which was used directly for the next step without further purification.

Step I: (2S,3R)-methyl 3-cyclopropyl-2-methyl-3-((R or S)-2-(2-(3-(trifluoromethyl)pyridin-2-yl)-2-azaspiro[3.3]heptan-6-yl)chroman-7-yl)propanoate The mixture of compounds from Step H (2S,3R)-methyl 3-cyclopropyl-2-methyl-3-((RS)-2-(2-(3-(trifluoromethyl)pyridin-2-yl)-2-azaspiro[3.3]-heptan-6-yl)chroman-7-yl)propanoate (49.0 mg, 0.0950 mmol) was separated by chiral SFC to give the first peak (2S,3R)-methyl 3-cyclopropyl-2-methyl-3-((R or S)-2-(2-(3-(trifluoromethyl)pyridin-2-yl)-2-azaspiro[3.3]heptan-6-yl)chroman-7-yl) propanoate, and the second peak (2S,3R)-methyl 3-cyclopropyl-2-methyl-3-((S or R)-2-(2-(3-(trifluoromethyl)-pyridin-2-yl)-2-azaspiro [3.3]heptan-6-yl)chroman-7-yl)-propanoate. SFC Conditions: Instrument: Berger MultiGram™ SFC, Mettler Toledo Co, Ltd; Column: AD (250 MM*30 MM*5 m); Mobile phase: 45% MeOH NH$_3$H2O 50 ML/MIN Column Temp: 38° C.; Nozzle Pressure: 100 Bar; Nozzle Temp: 60 OC; Evaporator Temp: 20 OC; Trimmer Temp: 25° C. and Wavelength: 220 nm.

Step J: (2S,3R)-3-cyclopropyl-2-methyl-3-((R or S)-2-(2-(3-(trifluoromethyl)pyridin-2-yl)-2-azaspiro[3.3]heptan-6-yl)chroman-7-yl)propanoic acid To a mixture of (2S,3R)-methyl 3-cyclopropyl-2-methyl-3-((R or S)-2-(2-(3-(trifluoromethyl)pyridin-2-yl)-2-azaspiro-[3.3]heptan-6-yl)chroman-7-yl)propanoate (15.0 mg, 0.0290 mmol) (the first peak obtained above) in THF (1.0 mL), MeOH (1.0 mL) and H$_2$O (1.0 mL) was added LiOH (14.0 mg, 0.583 mmol). The reaction mixture was stirred at 50° C. for 12 h, then an aqueous solution of HCl (1.0 M) was added to adjust the mixture pH to pH=5. The mixture was extracted with EtOAc (5 mL×3). The combined organic layers were concentrated under reduced pressure. The resulting residue was purified by preparative HPLC (preparative HPLC on a GILSON 281 instrument fitted with Phenomenex Gemini C18 250*21.2 mm*5 μm; mobile phase A: water (Neutral), mobile phase B: acetonitrile; gradient: 25-55% B, 0-10 min; 100% B, 10.5-12.5 min; 5% B, 13-15 min) to give the title compound. To a solution of the title compound in MeCN (1.0 mL) and water (1.0 mL) was added aqueous solution of NaOH (1.0 eq, 0.5 M). The reaction mixture was stirred for 1 h at room temperature (25° C.), and then lyophilized to give the sodium salt of the title compound. MS (ESI) m/z: 501.2 [M+H]$^+$ 1H NMR (400 MHz, CDCl3): δ=8.21 (d, J=4.4 Hz, 1H), 7.75 (d, J=8.0 Hz, 1H), 7.00 (d, J=8.0 Hz, 1H), 6.84-6.83 (m, 2H), 6.60 (t, J=5.2 Hz, 1H), 4.42 (d, J=6.0 Hz, 1H), 4.32 (d, J=5.6 Hz, 1H), 4.22-4.13 (m, 3H), 2.98-2.95 (m, 1H), 2.85-2.69 (m, 2H), 2.46-2.39 (m, 5H), 2.22-2.20 (m, 1H), 1.77-1.73 (m, 2H), 1.31-1.30 (m, 1H), 1.01 (d, J=6.8 Hz, 1H), 0.68-0.61 (m, 2H), 0.41-0.39 (m, 1H), 0.19-0.16 (m, 1H).

Example 2

(2S,3R)-3-cyclopropyl-2-methyl-3-((R or S)-2-(2-(3-(trifluoromethyl)pyridin-2-yl)-2-azaspiro[3.3]heptan-6-yl)chroman-7-yl)propanoic Acid The second peak obtained in Example 1 Step I was prepared in the same way as described for the first peak to afford the title compound, the diastereomer of Example 1. MS (ESI) m/z: 501.2 [M+H]$^+$ $^1$H NMR (400 MHz, CDCl3): δ=8.33 (d, J=4.0 Hz, 1H), 7.74 (d, J=7.6 Hz, 1H), 6.98 (d, J=7.6 Hz, 1H), 6.82 (s, 1H), 6.65-6.60 (m, 3H), 4.33 (d, J=9.6 Hz, 1H), 4.23-4.20 (m, 3H), 4.03 (d, J=10.8 Hz, 1H), 2.87-2.71 (m, 3H), 2.43-2.25 (m, 5H), 1.95-1.67 (m, 3H), 1.26-1.22 (m, 1H), 1.19 (d, J=8.0 Hz, 1H), 0.70-0.66 (m, 1H), 0.41-0.38 (m, 2H), 0.07-0.03 (m, 1H).

SCHEME 2

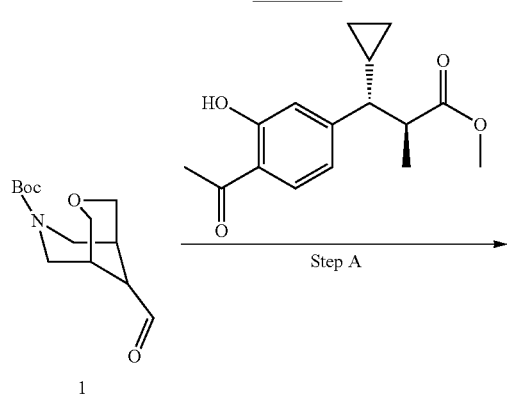
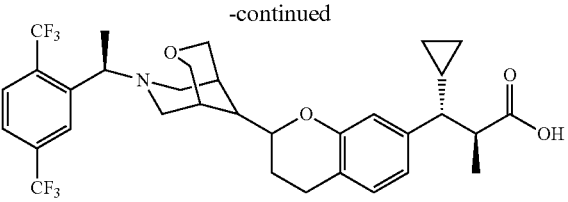
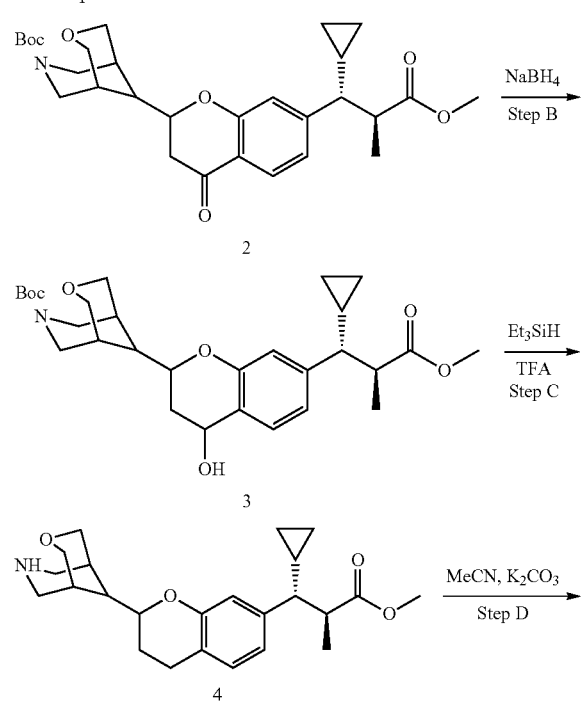
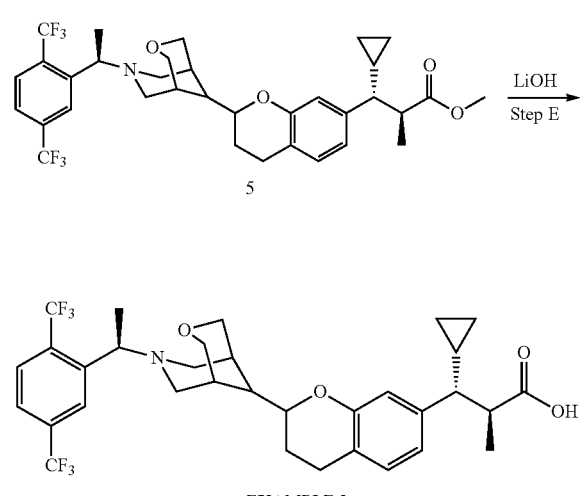

Example 3 and Example 4

(2S,3R)-3-(2-((1R,5S)-7-((R)-1-(2,5-bis(trifluorom-ethyl)phenyl)ethyl)-3-oxa-7-azabicyclo[3.3.1]nonan-9-yl)chroman-7-yl)-3-cyclopropyl-2-methylpropanoic Acid Step A: (2S,3R)-methyl 3-(2-((1R 5S)-3-oxa-7-azabicyclo[3.3.1]nonan-9-yl)-chroman-7-yl)-3-cyclopropyl-2-methylpropanoate To a solution of (1R,5S)-tert-butyl 9-formyl-3-oxa-azabicyclo-[3.3.1]-nonane-7-carboxylate (400 mg, 1.57 mmol) and (2S,3R)-methyl 3-(4-acetyl-3-hydroxyphenyl)-3-cyclopropyl-2-methylpropanoate (455 mg, 1.65 mmol) in MeOH (8.0 mL) was added pyrrolidine (155 μl, 1.88 mmol). The reaction mixture was stirred at 60° C. overnight, followed by evaporation under reduced pressure to give a residue, which was purified by Prep-TLC (SiO₂, PE:EtOAc=5:1, v/v) to afford the title compound. MS (ESI) m/z: 514.3 [M+H]⁺

Step B: (1R,5S)-tert-butyl 9-(7-((1R,2S)-1-cyclopropyl-3-methoxy-2-methyl-3-oxopropyl)-4-hydroxychroman-2-yl)-3-oxa-7-azabicyclo[3.3.1]nonane-7-carboxylate To a solution of (1R,5S)-tert-butyl 9-(7-((1R,2S)-1-cyclopropyl-3-methoxy-2-methyl-3-oxopropyl)-4-oxochroman-2-yl)-3-oxa-7-azabicyclo[3.3.1]nonane-7-carboxylate (920 mg, 1.79 mmol) in MeOH (10 mL) was added sodium tetrahydroborate (136 mg, 3.58 mmol). The reaction mixture was stirred for 30 min at room temperature, then water (15 mL) was added, and the mixture was extracted with EtOAc (15 mL×3). The combined organic layers were washed with brine (10 mL), dried over anhydrous Na₂SO₄ and filtered. The filtrate was evaporated under reduce pressure to give a residue, which was purified by Pre-TLC (SiO₂, PE:EtOAc=1/1, v/v) to afford the title compound. MS (ESI) m/z: 516.3 [M+H]⁺

Step C: (2S,3R)-methyl 3-(2-((1R,5S)-3-oxa-7-azabicyclo[3.3.1]nonan-9-yl)chroman-7-yl)-3-cyclopropyl-2-methylpropanoate To a solution of (1R,5S)-tert-butyl 9-(7-((1R,2S)-1-cyclopropyl-3-methoxy-2-methyl-3-oxopropyl)-4-hydroxy-chroman-2-yl)-3-oxa-7-azabicyclo[3.3.1]nonane-7-carboxylate (600 mg, 1.16 mmol) in DCM (10 mL) were added TFA (3.0 mL, 38.9 mmol) and triethylsilane (2.5 m L, 15.7 mmol). The reaction mixture was stirred 2 h, then water (5.0 mL) and Na$_2$CO$_3$ were added to adjust the pH of the mixture to pH 9-10. Then the mixture was extracted with EtOAc (10 mL×3). The combined organic layers were washed with brine (10 mL), dried over anhydrous Na$_2$SO$_4$ and filtered. The filtrate was evaporated under reduce pressure, to give the title compound, which was used directly for the next step. MS (ESI) m/z: 400.0 [M+H]$^+$ Step D: (2S,3R)-methyl 3-(2-((1R,5S)-7-((R)-1-(2,5-bis(trifluoromethyl)phenyl)ethyl)-3-oxa-7-azabicyclo[3.3.1]nonan-9-yl)chroman-7-yl)-3-cyclopropyl-2-methylpropanoate A solution of 1-(2,5-bis(trifluoromethyl)phenyl)ethyl methanesulfonate (67.7 mg, 0.201 mmol), K$_2$CO$_3$ (232 mg, 1.68 mmol) and (2S,3R)-methyl 3-(2-((1R,5S)-3-oxa-7-azabicyclo[3.3.1]nonan-9-yl)chroman-7-yl)-3-cyclopropyl-2-methylpropanoate (67 mg, 0.168 mmol) in MeCN (4.0 mL) was stirred at 90° C. for 2 h. Then water (5.0 mL) was added, and the mixture was extracted with EtOAc (10 mL×3). The combined organic layers were washed with brine (2 mL×2) dried over anhydrous Na$_2$SO$_4$ and filtered. The filtrate was evaporated under reduce pressure to give a residue, which was purified by Prep-TLC (SiO$_2$, PE:EtOAc=10:1, v/v) to afford the title compound. MS (ESI) m/z: 640.2 [M+H]$^+$ Step E: (2S,3R)-3-(2-((1R,5S)-7-((R)-1-(2,5-bis(trifluoromethyl)phenyl)ethyl)-3-oxa-7-azabicyclo[3.3.1]nonan-9-yl)chroman-7-yl)-3-cyclopropyl-2-methylpropanoic Acid To a solution of (2S,3R)-methyl 3-(2-((1R,5S)-7-((R)-1-(2,5-bis(trifluoromethyl)phenyl)ethyl)-3-oxa-7-azabicyclo[3.3.1]nonan-9-yl)chroman-7-yl)-3-cyclopropyl-2-methyl propanoate (37.0 mg, 0.0580 mmol) in THF(1.5 mL), water (1.5 mL) and MeOH (1.5 mL) was added LiOH (13.8 mg, 0.063 mmol). The reaction mixture was stirred at 50° C. for 16 h, then water (5.0 mL) was added. The pH of the mixture was adjusted with citric acid to pH 6-7. Then the mixture was extracted with EtOAc (7 mL×3). The combined organic layers were washed with brine (10 mL) dried over anhydrous Na$_2$SO$_4$ and filtered. The filtrate was concentrated in vacuo to give a residue, which was purified Prep-HPLC to afford two isomers: Example 3: (2S,3R)-3-(2-((1R,5S)-7-((R)-1-(2,5-bis(trifluoromethyl)phenyl)ethyl)-3-oxa-7-azabicyclo[3.3.1]nonan-9-yl)chroman-7-yl)-3-cyclopropyl-2-methylpropanoic acid; and Example 4: (2S,3R)-3-(2-((1R,5S)-7-((R)-1-(2,5-bis(trifluoromethyl)phenyl)ethyl)-3-oxa-7-azabicyclo[3.3.1]nonan-9-yl)chroman-7-yl)-3-cyclopropyl-2-methylpropanoic acid. Prep HPLC conditions: MS trigger instrument fitted with a Phenomenex Synergi C18 250*21.2 mm*5 um; mobile phase A: water (10 mM NH$_4$HCO$_3$); mobile phase B: acetonitrile; gradient: 37-67% B, 0-12.0 min; 100% B, 2 min); Flow Rate: 25 m L/min.

Example 3

MS (ESI) m/z: 626.2 [M+H]$^+$ $^1$H NMR (400 MHz, CD3OD) δ=8.52 (br. d, J=1.0 Hz, 1H), 7.83 (d, J=8.2 Hz, 1H), 7.70 (d, J=7.9 Hz, 1H), 6.96 (d, J=7.9 Hz, 1H), 6.63 (d, J=7.5 Hz, 1H), 6.50 (s, 1H), 4.59-4.58 (m, 1H), 4.39-4.33 (m, 1H), 4.18-4.12 (m, 1H), 3.86-3.80 (m, 1H), 3.76-3.71 (m, 1H), 3.67-3.61 (m, 1H), 3.57-3.52 (m, 1H), 3.47-3.44 (m, 1H), 3.49-3.44 (m, 1H), 3.14-3.08 (m, 1H), 3.06-2.99 (m, 1H), 2.87-2.81 (m, 1H), 2.67-2.62 (m, 1H), 2.58-2.51 (m, 1H), 2.48-2.41 (m, 1H), 2.22-2.17 (m, 1H), 2.10-2.05 (m, 1H), 1.95-1.91 (m, 1H), 1.87-1.80 (m, 1H), 1.70-1.54 (m, 2H), 1.34-1.28 (m, 2H), 1.06-0.98 (m, 1H), 0.93-0.81 (m, J=6.6 Hz, 3H), 0.93-0.81 (m, 3H), 0.57-0.49 (m, 1H), 0.33-0.21 (m, 2H), 0.1-0.04 (m, 1H).

Example 4

MS (ESI) m/z: 626.2 [M+H]$^+$ $^1$H NMR (400 MHz, CD3OD) δ=8.54 (s, 1H), 7.83 (d, J=8.2 Hz, 1H), 7.70 (d, J=8.2 Hz, 1H), 6.95 (d, J=7.7 Hz, 1H), 6.61 (d, J=7.5 Hz, 1H), 6.49 (s, 1H), 4.60-4.58 (m, 2H), 4.53-4.46 (m, 1H), 4.07 (d, J=11.5 Hz, 1H), 3.99 (d, J=11.2 Hz, 1H), 3.86 (d, J=11.5 Hz, 1H), 3.64-3.59 (m, 1H), 3.56-3.49 (m, 1H), 3.05-2.97 (m, 1H), 2.89-2.80 (m, 1H), 2.89-2.80 (m, 1H), 2.73-2.68 (m, 1H), 2.45 (d, J=10.4 Hz, 1H), 2.17-2.11 (m, 1H), 2.06 (S, 1H), 1.94 (S, 1H), 1.85-1.77 (m, 1H), 1.76-1.69 (m, 1H), 1.65-1.57 (m, 1H), 1.41 (d, J=6.4 Hz, 1H), 1.33 (d, J=6.4 Hz, 2H), 1.28-1.25 (m, 1H), 1.03-0.96 (m, 1H), 0.83 (d, J=6.6 Hz, 3H), 0.55-0.47 (m, 1H), 0.32-0.19 (m, 2H), 0.1-0.01 (m, 1H)

TABLE 1

The compounds of Examples 5-8 were prepared according to the procedures described above using the appropriate intermediates and commercially available starting materials.

| Example | Structure | M.W. | Compound Name | LC/MS (ESI) observed [M + H]$^+$ |
|---|---|---|---|---|
| 5 | 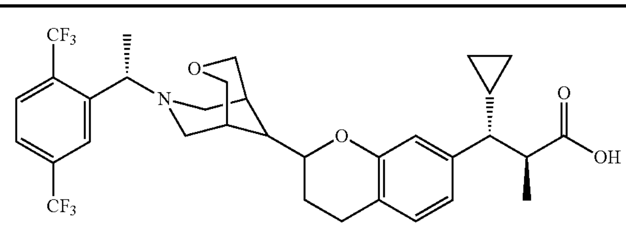 | 625.64 | (2S,3R)-3-(2-((1R,5S)-7-((S)-1-(2,5-bis(trifluoromethyl)phenyl)ethyl)-3-oxa-7-azabicyclo[3.3.1]-nonan-9-yl)chroman-7-yl)-3-cyclopropyl-2-methylpropanoic acid | 626.2 |

TABLE 1-continued

The compounds of Examples 5-8 were prepared according to the procedures described above using the appropriate intermediates and commercially available starting materials.

| Example | Structure | M.W. | Compound Name | LC/MS (ESI) observed [M + H]+ |
|---|---|---|---|---|
| 6 | 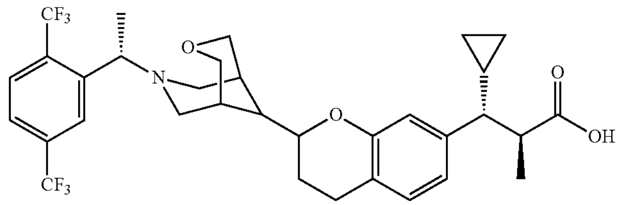 [SMILES: C[C@H](C(=O)O)[C@H](c1ccc2c(c1)OC(C1C3COCC1CN([C@@H](C)c1cc(C(F)(F)F)ccc1C(F)(F)F)C3)CC2)C1CC1] | 625.64 | (2S,3R)-3-(2-((1R,5S)-7-((S)-1-(2,5-bis(trifluoro-methyl)phenyl)ethyl)-3-oxa-7-azabicyclo[3.3.1]-nonan-9-yl)chroman-7-yl)-3-cyclopropyl-2-methyl-propanoic acid | 626.2 |
| 7 | 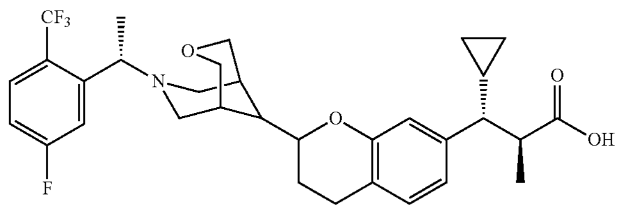 [SMILES: C[C@H](C(=O)O)[C@H](c1ccc2c(c1)OC(C1C3COCC1CN([C@@H](C)c1cc(F)ccc1C(F)(F)F)C3)CC2)C1CC1] | 575.63 | (2S,3R)-3-cyclopropyl-3-(2-((1R,5S)-7-(1-(5-fluoro-2-(trifluoromethyl)-phenyl)ethyl)-3-oxa-7-azabicyclo[3.3.1]nonan-9-yl)chroman-7-yl)-2-methylpropanoic acid | 576.3 |
| 8 | 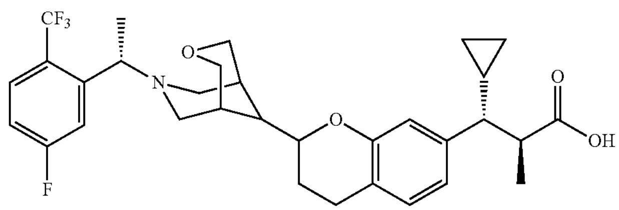 [SMILES: C[C@H](C(=O)O)[C@H](c1ccc2c(c1)OC(C1C3COCC1CN([C@@H](C)c1cc(F)ccc1C(F)(F)F)C3)CC2)C1CC1] | 575.63 | (2S,3R)-3-cyclopropyl-3-(2-((1R,5S)-7-(1-(5-fluoro-2-(trifluoromethyl)--phenyl)-ethyl)-3-oxa-7-azabicyclo[3.3.1]nonan-9-yl)chroman-7-yl)-2-methylpropanoic acid | 576.3 |

Example 5

MS (ESI) m/z: 626.2 [M+H]+ 1H NMR (400 MHz, CD3OD) δ=8.49 (s, 1H), 7.81 (d, J=8.2 Hz, 1H), 7.68 (d, J=8.2 Hz, 1H), 6.95 (d, J=7.7 Hz, 1H), 6.61 (d, J=7.5 Hz, 1H), 6.49 (s, 1H), 4.38-4.29 (m, 1H), 4.13 (d, J=10.8 Hz, 1H), 3.81 (d, J=10.6 Hz, 2H), 3.74-3.61 (m, 2H), 3.00 (d, J=7.3 Hz, 1H), 2.85-2.70 (m, 2H), 2.68-2.59 (m, 2H), 2.58-2.50 (m, 1H), 2.47-2.39 (m, 1H), 2.21-2.12 (m, 1H), 2.10-2.03 (m, 1H), 1.95-1.85 (m, 2H), 1.85-1.76 (m, 1H), 1.65-1.54 (m, 1H), 1.35-1.22 (m, 3H), 1.00 (d, J=3.1 Hz, 1H), 0.83 (d, J=6.6 Hz, 3H), 0.55-0.46 (m, 1H), 0.31-0.18 (m, 2H), 0.12-0.09 (m, 1H) Example 6: MS (ESI) m/z: 626.2 [M+H]+ 1H NMR (400 MHz, CD3OD) δ=8.54 (s, 1H), 7.83 (d, J=8.2 Hz, 1H), 7.70 (d, J=8.2 Hz, 1H), 6.95 (d, J=7.7 Hz, 1H), 6.61 (d, J=7.5 Hz, 1H), 6.49 (s, 1H), 4.60-4.58 (m, 2H), 4.53-4.46 (m, 1H), 4.07 (d, J=11.5 Hz, 1H), 3.99 (d, J=11.2 Hz, 1H), 3.86 (d, J=11.5 Hz, 1H), 3.64-3.59 (m, 1H), 3.56-3.49 (m, 1H), 3.05-2.97 (m, 1H), 2.89-2.80 (m, 1H), 2.89-2.80 (m, 1H), 2.73-2.68 (m, 1H), 2.45 (d, J=10.4 Hz, 1H), 2.17-2.11 (m, 1H), 2.06 (S, 1H), 1.94 (S, 1H), 1.85-1.77 (m, 1H), 1.76-1.69 (m, 1H), 1.65-1.57 (m, 1H), 1.41 (d, J=6.4 Hz, 1H), 1.33 (d, J=6.4 Hz, 2H), 1.28-1.25 (m, 1H), 1.03-0.96 (m, 1H), 0.83 (d, J=6.6 Hz, 3H), 0.55-0.47 (m, 1H), 0.32-0.19 (m, 2H), 0.1-0.01 (m, 1H)

Example 7

MS (ESI) m/z: 576.3 [M+H]+ 1H NMR (400 MHz, CD3OD) δ=7.87 (d, J=10.1 Hz, 1H), 7.70-7.61 (m, 1H), 7.15-7.06 (m, 1H), 6.94 (d, J=7.7 Hz, 1H), 6.61 (d, J=7.7 Hz, 1H), 6.57-6.48 (m, 1H), 4.32 (t, J=9.6 Hz, 1H), 4.21-4.09 (m, 1H), 3.90-3.57 (m, 4H), 3.38-3.25 (m, 2H), 2.90-2.81 (m, 1H), 2.80-2.61 (m, 3H), 2.61-2.52 (m, 1H), 2.42-2.29 (m, 1H), 2.14-2.03 (m, 1H), 1.94-1.87 (m, 1H), 1.86-1.76 (m, 1H), 1.73-1.48 (m, 2H), 1.39-1.25 (m, 3H), 1.08-0.95 (m, 1H), 1.01 (s., 1H), 0.90-0.79 (m, 3H), 0.58-0.47 (m, 1H), 0.33-0.17 (m, 2H), 0.1-0.01 (m, 1H)

Example 8

MS (ESI) m/z: 576.3 [M+H]+ 1H NMR (400 MHz, CD3OD) δ=7.92 (d, J=10.4 Hz, 1H), 7.72-7.64 (m, 1H), 7.16-7.08 (m, 1H), 6.96 (d, J=7.7 Hz, 1H), 6.66-6.59 (m, 1H), 6.58-6.49 (m, 1H), 4.60 (s, 1H), 4.52 (t, J=9.9 Hz, 1H), 4.19 (d, J=11.9 Hz, 1H), 4.09 (d, J=11.5 Hz, 1H), 4.01 (d, J=11.5 Hz, 1H), 3.95-3.82 (m, 2H), 3.67-3.52 (m, 3H), 2.88-2.76 (m, 2H), 2.52-2.41 (m, 1H), 2.26-2.08 (m, 2H), 1.98-1.89 (m, 1H), 1.89-1.80 (m, 1H), 1.79-1.72 (m, 1H), 1.72-1.63 (m, 1H), 1.39-1.26 (m, 3H), 1.09-0.98 (m, 1H), 0.96-0.81 (m, 3H), 0.61-0.48 (m, 1H), 0.37-0.19 (m, 2H), −0.01--0.12 (m, 1H), −0.04--0.12 (m, 1H).

SCHEME 3

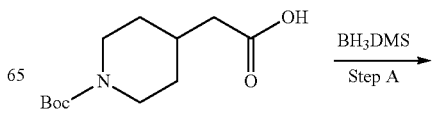

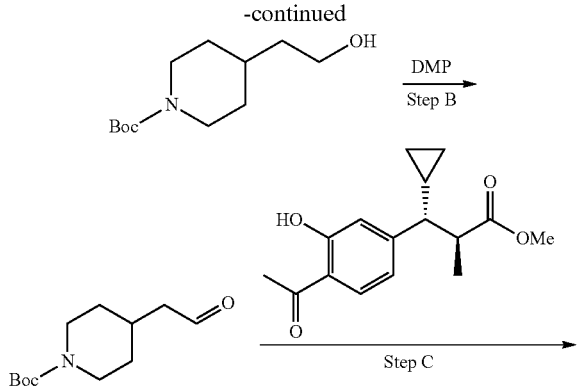

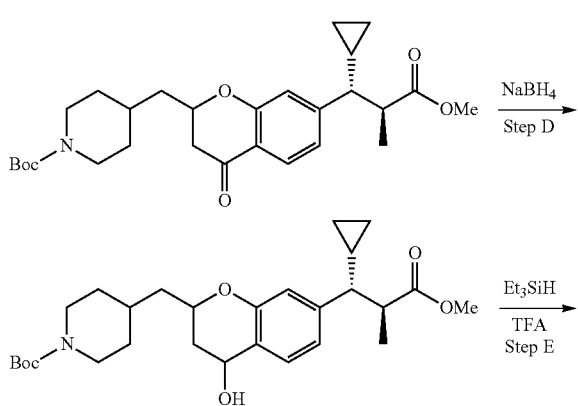

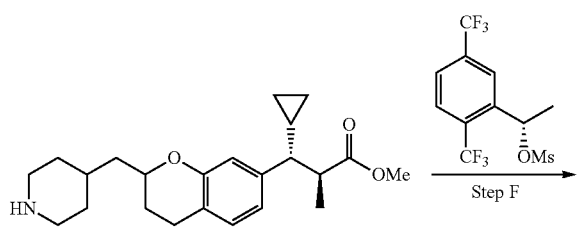

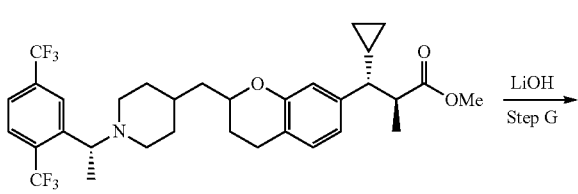

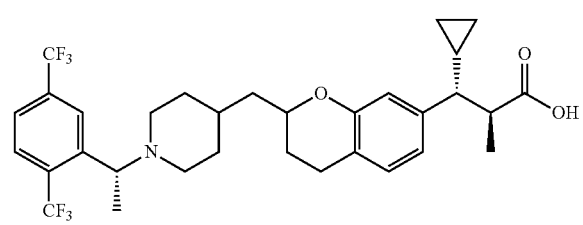 [SMILES: C[C@H](C(=O)O)[C@H](c1ccc2c(c1)OC(CC1CCN([C@H](C)c3cc(C(F)(F)F)ccc3C(F)(F)F)CC1)CC2)C1CC1]

Example 9

(2S,3R)-3-((RS)-2-((1-((R)-1-(2,5-bis(trifluoromethyl)phenyl)ethyl)piperidin-4-yl)-methyl)chroman-7-yl)-3-cyclopropyl-2-methylpropanoic Acid

Step A: tert-butyl 4-(2-hydroxyethyl)piperidine-1-carboxylate

To a solution of 2-(1-(tert-butoxycarbonyl)piperidin-4-yl) acetic acid (5.00 g, 20.6 mmol) in THF (50 mL) was added dropwise BH$_3$DMS (4.11 mL, 41.1 mmol) at 25° C. under N$_2$. The reaction mixture was stirred at 0° C. for 1 h, followed by 25° C. for 10 h. Then MeOH (20 mL) was added to the mixture dropwise at 0° C., and the solvent was removed under reduced pressure to give the crude product, which was purified by column chromatography (SiO$_2$, PE:EA=5:1) to give the title compound. MS (ESI) m/z: 215.1 [M-56+MeCN+H]$^+$

Step B: tert-butyl 4-(2-oxoethyl)piperidine-1-carboxylate

To a solution of tert-butyl 4-(2-hydroxyethyl)piperidine-1-carboxylate (500 mg, 2.18 mmol) in DCM (10 mL) was added DMP (1.39 g, 3.27 mmol). The reaction mixture was stirred at 25° C. for 1 h, then the reaction was quenched with NaOH (20 mL, 1M). The resulting mixture was stirred at 25° C. until the solid dissolved, then extracted with DCM (20 mL×3). The combined organic layers were washed with brine (20 mL), dried over MgSO$_4$, and filtered. The filtrate was concentrated in vacuo to give title compound, which was used for next step without further purification. MS (ESI) m/z: 213.1 [M-56+MeCN+H]$^+$ $^1$H NMR (400 MHz, CDCl$_3$): δ=9.78 (s, 1H), 4.16-4.00 (m, 1H), 2.83-2.68 (m, 1H), 2.39 (d, J=6.7 Hz, 2H), 2.13-1.99 (m, 1H), 1.70 (d, J=12.5 Hz, 1H), 1.46 (s, 9H), 1.25-1.12 (m, 1H)

Step C: tert-butyl 4-(((RS)-7-(((1R,2S)-1-cyclopropyl-3-methoxy-2-methyl-3-oxopropyl)-4-oxochroman-2-yl)methyl)piperidine-1-carboxylate Tert-butyl 4-(2-oxoethyl)piperidine-1-carboxylate (362 mg, 1.59 mmol) and (2S,3R)-methyl 3-(4-acetyl-3-hydroxyphenyl)-3-cyclopropyl-2-methylpropanoate (400 mg, 1.45 mmol) were combined in dry MeOH (2.0 mL). Pyrrolidine (124 mg, 1.74 mmol) was added, and the reaction was heated at 60° C. for 2 h. Then the MeOH was removed, and the resulting residue was diluted with H$_2$O (15 mL). The resulting mixture was extracted with EtOAc (20 mL×3). The combined organic layers were washed with brine (15 mL), dried (MgSO4), and filtered. The filtrate was concentrated under reduced pressure to give the crude product, which was purified by Prep-TLC (SiO$_2$, PE:EA=3:1,v/v) to give the title compound. MS (ESI) m/z: 508.3 [M+Na]$^+$

Step D: tert-butyl 4-(((2RS)-7-((1R,2S)-1-cyclopropyl-3-methoxy-2-methyl-3-oxopropyl)-4-hydroxychroman-2-yl)methyl)piperidine-1-carboxylate To a solution of tert-butyl 4-(((RS)-7-((1R,2S)-1-cyclopropyl-3-methoxy-2-methyl-3-oxopropyl)-4-oxochroman-2-yl)methyl)piperidine-1-carboxylate (700 mg, 1.44 mmol) in MeOH (10 mL) was added NaBH$_4$ (109 mg, 2.88 mmol) at 0° C. The reaction mixture was stirred at 0° C. for 30 min, then quenched with saturated aqueous NH$_4$Cl (15 mL). The resulting mixture was extracted with EtOAc (30 mL×3). The combined organic layers were washed with brine (saturated, 20 mL), dried (Na$_2$SO$_4$), and filtered. The filtrate was evaporated under reduced pressure to give the crude product, which was purified by prep-TLC (SiO$_2$, PE:EA=2:1, v/v) to give the title compound. MS (ESI) m/z: 510.3 [M+Na]$^+$ 1H NMR (400 MHz, CDCl$_3$): δ=7.39 (d, J=7.8 Hz, 1H), 6.77-6.70 (m, 1H), 6.61 (s, 1H), 5.00-4.88 (m, 1H), 4.27-4.18 (m, 1H), 4.16-4.03 (m, 2H), 3.73 (s, 3H), 2.84-2.68 (m, 3H), 2.33-2.23 (m, 1H), 1.91-1.67 (m, 7H), 1.47 (s, 9H), 1.26-1.11 (m, 2H), 1.07-1.00 (m, 1H), 0.95 (d, J=6.7 Hz, 3H), 0.60-0.50 (m, 1H), 0.38-0.29 (m, 1H), 0.28-0.19 (m, 1H), 0.04-0.04 (m, 1H)

Step E: (2S,3R)-methyl 3-cyclopropyl-2-methyl-3-((RS)-2-(piperidin-4-ylmethyl)chroman-7-yl)propanoate To a solution of tert-butyl 4-(((2RS)-7-((1R,2S)-1-cyclopropyl-3-methoxy-2-methyl-3-oxopropyl)-4-hydroxychroman-2-yl)methyl)piperidine-1-carboxylate (550 mg, 1.13 mmol) in DCM (8.0 mL) was added triethylsilane (2.0 mL, 12.5 mmol) and TFA (2.0 mL, 26.0 mmol). The reaction mixture was stirred at 25° C. under N$_2$ protection for 1 h, then the solvent was removed under reduced pressure. The resulting residue was neutralized with saturated NaHCO$_3$ aqueous (30 mL). The mixture was extracted with DCM (30 mL×3). The combined organic layers were washed with brine (20 mL), dried (Na$_2$SO$_4$), and filtered. The filtrate was evaporated under reduced pressure to give the title compound, which was used for next step without further purification. MS (ESI) m/z: 372.2 [M+H]

Step F: (2S,3R)-methyl 3-((RS)-2-((1-((R)-1-(2,5-bis(trifluoromethyl)phenyl)ethyl) piperidin-4-yl)methyl)chroman-7-yl)-3-cyclopropyl-2-methylpropanoate To a solution of (2S,3R)-methyl 3-cyclopropyl-2-methyl-3-((RS)-2-(piperidin-4-ylmethyl) chroman-7-yl)propanoate (150 mg, 0.404 mmol) and DIPEA (0.353 mL, 2.02 mmol) in MeCN (5.0 mL) was added (S)-1-(2,5-bis(trifluoromethyl)phenyl)ethyl methanesulfonate (163 mg, 0.485 mmol). The reaction mixture was stirred at 80° C. under N$_2$ protection for 35 h. Then the solvent was removed under reduced pressure to give the crude product, which was purified by prep-HPLC (TFA) to give the title compound. MS (ESI) m/z: 612.3 [M+H]$^+$ 1H NMR (400 MHz, CD3OD): δ=8.33 (br. s., 1H), 8.16-8.10 (m, 1H), 8.08-8.02 (m, 1H), 6.98 (d, J=7.5 Hz, 1H), 6.67-6.61 (m, 1H), 6.57-6.51 (m, 1H), 4.79-4.69 (m, 1H), 4.18-4.01 (m, 2H), 3.72 (d, J=1.8 Hz, 3H), 3.31-3.21 (m, 1H), 3.19-3.10 (m, 1H), 3.02-2.91 (m, 1H), 2.90-2.71 (m, 3H), 2.32-2.19 (m, 1H), 2.14-1.96 (m, 3H), 1.86-1.67 (m, 7H), 1.64-1.38 (m, 2H), 1.10-0.97 (m, 1H), 0.90 (d, J=6.8 Hz, 3H), 0.60-0.49 (m, 1H), 0.34-0.25 (m, 1H), 0.23-0.14 (m, 1H), 0.01-0.10 (m, 1H).

Step G: (2S,3R)-3-((RS)-2-((1-((R)-1-(2,5-bis(trifluoromethyl)phenyl)ethyl)piperidin-4-yl)methyl) chroman-7-yl)-3-cyclopropyl-2-methylpropanoic Acid To a solution of (2S,3R)-methyl 3-((RS)-2-((1-((R)-1-(2,5-bis(trifluoromethyl)phenyl)ethyl)piperidin-4-yl)methyl) chroman-7-yl)-3-cyclopropyl-2-methylpropanoate (120 mg, 0.196 mmol) in MeOH (2.0 mL), THF (2.0 mL) and Water (2.0 mL) was added LiOH (94.0 mg, 3.92 mmol). The reaction mixture was stirred at 50° C. for 30 h, then cooled to 25° C. The mixture was acidified with citric acid to adjust the pH to pH=5-6 and extracted with EtOAc (10 mL×3). The combined organic layers were dried(Na$_2$SO$_4$) and filtered. The filtrate was concentrated in vacuo to give the crude product. The crude product was purified by prep-TLC (SiO$_2$, PE:EA=2:1, v/v) to give the title compound as a mixture of stereoisomers.

To a solution of the title compound (~10 mg) in MeCN (1.0 mL) and water (1.0 mL) was added an aqueous solution of NaOH (1.0 eq, 0.5 M), and the mixture was stirred for 1 h at room temperature. Then the reaction mixture was lyophilized to give the sodium salt of the title compound. MS (ESI) m/z: 598.3[M+H]$^+$ 1H NMR (400 MHz, CD$_3$OD): δ=8.25 (s, 1H), 7.87 (d, J=7.8 Hz, 1H), 7.74 (d, J=7.8 Hz, 1H), 6.93 (d, J=7.4 Hz, 1H), 6.61 (d, J=7.4 Hz, 1H), 6.54 (s, 1H), 4.13-3.99 (m, 1H), 3.81-3.71 (m, 1H), 3.45-3.36 (m, 1H), 2.89-2.75 (m, 1H), 2.75-2.63 (m, 1H), 2.57-2.48 (m, 1H), 2.20-2.08 (m, 1H), 2.01-1.93 (m, 1H), 1.89-1.81 (m, 1H), 1.76-1.60 (m, 1H), 1.54-1.39 (m, 1H), 1.38-1.27 (m, 4H), 1.22-1.11 (m, 1H), 1.10-0.98 (m, 1H), 0.89 (d, J=6.7 Hz, 3H), 0.62-0.50 (m, 1H), 0.37-0.22 (m, 1H), 0.00-0.11 (m, 1H)

Example 10 and Example 11

(2S,3R)-3-((R or S)-2-((1-((R)-1-(2,5-bis(trifluoromethyl)phenyl)ethyl) piperidin-4-yl)-methyl)chroman-7-yl)-3-cyclopropyl-2-methylpropanoic Acid (Example 10) and (2S,3R)-3-((S or R)-2-((1-((R)-1-(2,5-bis(trifluoromethyl)phenyl)ethyl)piperidin-4-yl)methyl)chroman-7-yl)-3-cyclopropyl-2-methylpropanoic Acid (Example 11)

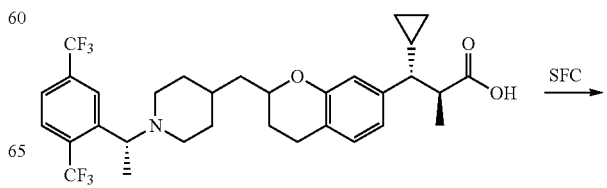

-continued

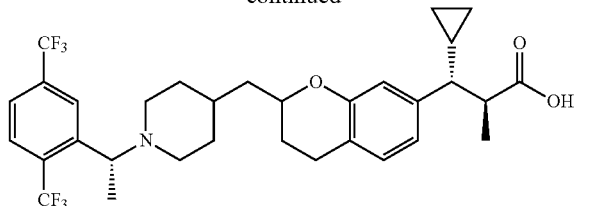

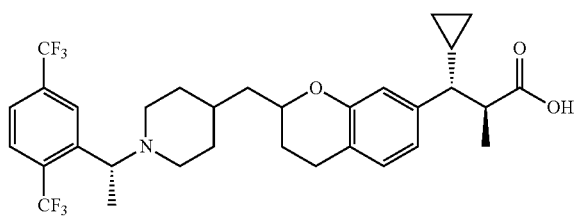 [SMILES: C[C@H](C(=O)O)[C@H](c1ccc2c(c1)OC(CC1CCN([C@@H](C)c3cc(C(F)(F)F)ccc3C(F)(F)F)CC1)CC2)C1CC1]

(2S,3R)-3-((RS)-2-((1-((R)-1-(2,5-bis(trifluoromethyl)phenyl)ethyl)piperidin-4-yl)methyl) chroman-7-yl)-3-cyclopropyl-2-methylpropanoic acid (90.0 mg, 0.151 mmol, the mixture of of stereoisomers of Example 9) was separated by chiral SFC to give the individual diastereoisomers of Example 10 and Example 11. Example 10: the first peak (2S,3R)-3-((R or S)-2-((1-((R)-1-(2,5-bis(trifluoromethyl)phenyl)ethyl) piperidin-4-yl)methyl)chroman-7-yl)-3-cyclopropyl-2-methylpropanoic acid (Rt=2.193 min). Example 11: the second peak (2S,3R)-3-((S or R)-2-((1-((R)-1-(2,5-bis(trifluoro-methyl)phenyl)ethyl) piperidin-4-yl)methyl)chroman-7-yl)-3-cyclopropyl-2-methyl-propanoic acid (Rt=2.525 min). To a solution of each diastereoisomer (5 mg) in MeCN (1.0 mL) and water (1.0 mL) was added the aqueous solution of NaOH (1.0 eq, 0.5 M), then the mixture was stirred for 1 hour at room temperature (25° C.). Then the reaction mixture was lyophilized by the lyophilizer to give the sodium salt of the title compounds. SFC Method: Column: Chiralpak AD-3 150× 4.6 mm I.D., 3 um; mobile phase: A: CO₂; B:methanol (0.05% DEA): gradient: from 5% to 40% of B in 5 min and hold 40% for 2.5 min, then 5% of B for 2.5 min; Flow rate: 2.5 mL/min; Column temp.: 35° C.

Example 10

MS (ESI) m/z: 598.2 [M+H]⁺ ¹H NMR (400 MHz, CD₃OD): δ=8.24 (s, 1H), 7.88 (d, J=8.2 Hz, 1H), 7.74 (d, J=8.2 Hz, 1H), 6.94 (d, J=7.4 Hz, 1H), 6.61 (d, J=7.8 Hz, 1H), 6.54 (s, 1H), 4.10-4.01 (m, 1H), 3.81-3.73 (m, 1H), 3.44-3.36 (m, 1H), 2.87-2.76 (m, 1H), 2.76-2.67 (m, 2H), 2.58-2.49 (m, 1H), 2.20-2.09 (m, 1H), 2.04-1.93 (m, 2H), 1.92-1.81 (m, 2H), 1.76-1.62 (m, 4H), 1.51-1.41 (m, 2H), 1.35 (d, J=6.3 Hz, 3H), 1.22-1.11 (m, 1H), 1.11-0.99 (m, 1H), 0.89 (d, J=6.7 Hz, 3H), 0.62-0.51 (m, 1H), 0.36-0.24 (m, 2H), 0.01-0.08 (m, 1H).

Example 11

MS (ESI) m/z: 598.2 [M+H]⁺ ¹H NMR (400 MHz, CD₃OD): δ=8.25 (s, 1H), 7.88 (d, J=8.2 Hz, 1H), 7.74 (d, J=8.2 Hz, 1H), 6.94 (d, J=7.4 Hz, 1H), 6.62 (d, J=7.4 Hz, 1H), 6.54 (s, 1H), 4.12-4.03 (m, 1H), 3.84-3.74 (m, 1H), 3.46-3.36 (m, 1H), 2.88-2.77 (m, 1H), 2.75-2.66 (m, 2H), 2.59-2.48 (m, 1H), 2.20-2.09 (m, 1H), 2.05-1.92 (m, 3H), 1.89-1.80 (m, 1H), 1.78-1.59 (m, 4H), 1.55-1.38 (m, 2H), 1.35 (d, J=6.3 Hz, 3H), 1.26-1.12 (m, 1H), 1.11-1.01 (m, 1H), 0.89 (d, J=7.0 Hz, 3H), 0.61-0.51 (m, 1H), 0.35-0.24 (m, 2H), 0.00-0.09 (m, 1H).

TABLE 2

The compound of Example 12 was prepared in a similar manner to the procedure of Example 9 using the appropriate intermediates and commercially available starting materials.

| Example | Structure | M.W. | Compound Name | LC/MS (ESI) observed [M + 1]⁺ |
|---|---|---|---|---|
| 12 | <img> | 597.63 | (2S,3R)-3-((RS)-2-((1-((S)-1-(2,5-bis(trifluoromethyl)phenyl)ethyl)piperidin-4-yl)methyl)-chroman-7-yl)-3-cyclopropyl-2-methyl-propanoic acid | 598.2 |

Example 12

¹H NMR (400 MHz, CD₃OD): δ=8.25 (s, 1H), 7.88 (d, J=8.2 Hz, 1H), 7.74 (d, J=8.2 Hz, 1H), 6.94 (d, J=7.4 Hz, 1H), 6.61 (d, J=7.8 Hz, 1H), 6.54 (s, 1H), 4.13-4.00 (m, 1H), 3.82-3.71 (m, 1H), 3.45-3.35 (m, 1H), 2.88-2.76 (m, 1H), 2.76-2.66 (m, 1H), 2.58-2.49 (m, 1H), 2.19-2.08 (m, 1H), 2.03-1.93 (m, 1H), 1.89-1.81 (m, 1H), 1.76-1.61 (m, 1H), 1.53-1.52 (m, 1H), 1.53-1.40 (m, 1H), 1.39-1.28 (m, 4H), 1.24-1.12 (m, 1H), 1.11-1.01 (m, 1H), 0.89 (d, J=6.7 Hz, 3H), 0.61-0.51 (m, 1H), 0.36-0.23 (m, 1H), 0.01-0.10 (m, 1H).

SCHEME 4

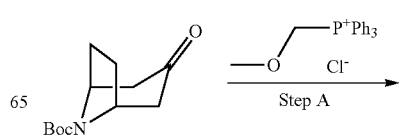

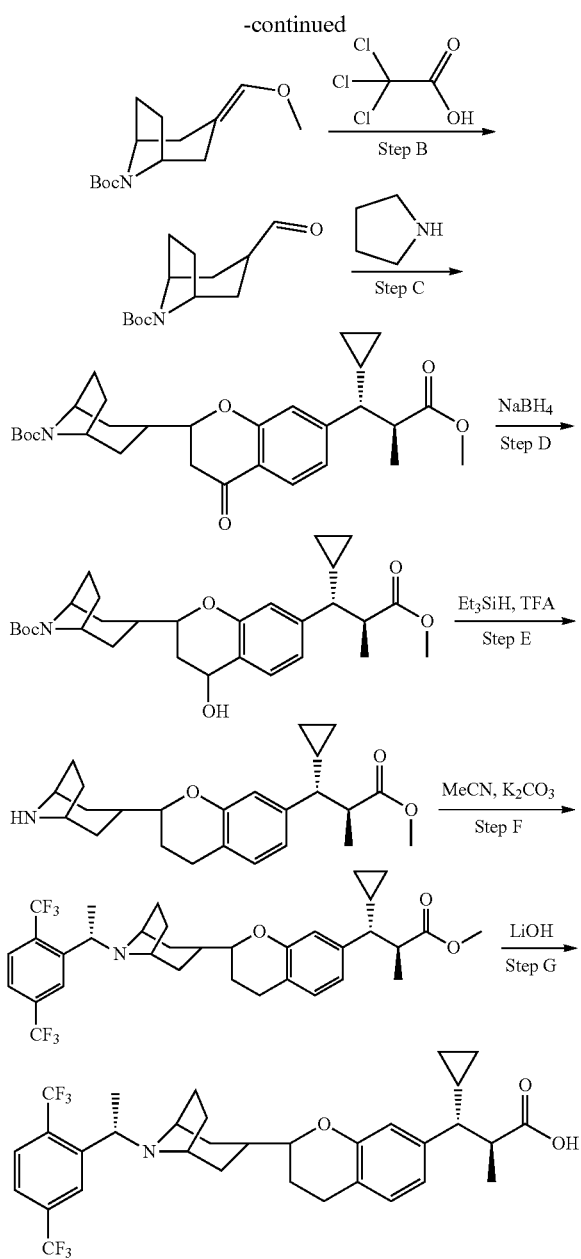

Example 13

(2S,3R)-3-(2-((1R5S)-8-((S)-1-(2,5-bis(trifluoromethyl)phenyl)ethyl)-8-azabicyclo[3.2.1]octan-3-yl)chroman-7-yl)-3-cyclopropyl-2-methylpropanoic Acid

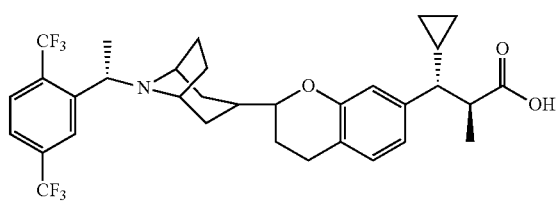 [SMILES: C[C@H](C(=O)O)[C@H](c1ccc2c(c1)OC(C1CC3CCC(C1)N3[C@@H](C)c1cc(C(F)(F)F)ccc1C(F)(F)F)CC2)C1CC1]

Step A: (1R,5S,Z)-tert-butyl 3-(methoxymethylene)-8-azabicyclo[3.2.1]octane-8-carboxylate To a solution of (methoxymethyl)triphenylphosphonium chloride (6.09 g, 17.8 mmol) in THF (20 mL) was added sodium bis(trimethylsilyl)amide (17.8 mL, 17.8 mmol) at 0° C. The mixture was stirred at 0° C. for 0.5 hour. Then (1R)-tert-butyl 3-oxo-8-azabicyclo[3.2.1]octane-8-carboxylate (2.00 g, 8.88 mmol) was added at 0° C., and the reaction mixture was stirred for 2 h at 0° C. under nitrogen protection. Then the reaction mixture was treated with water (50 mL) and ethyl acetate (30 mL). The organic layer was separated. The aqueous layer was extracted with ethyl acetate (30 mL×3). The combined organic layers were dried over anhydrous sodium sulfate, filtered and concentrated under reduced pressure. The crude product was purified by column chromatography (silica gel, PE to PE:EtOAc=30:1, v/v) to afford the title compound. $^1$H NMR (400 MHz, CDCl$_3$): δ=5.89 (s, 1H), 4.28-4.08 (m, 2H), 3.54 (s, 3H), 2.47 (d, J=14.1 Hz, 1H), 2.33 (d, J=15.9 Hz, 1H), 2.19-1.98 (m, 1H), 1.85 (br. s., 2H), 1.76 (d, J=13.7 Hz, 1H), 1.66 (s, 1H), 1.62-1.49 (m, 3H), 1.46 (s, 9H). MS (ESI) m/z: 154.1 [M-100+H]$^+$.

Step B: (1R,5S)-tert-butyl 3-formyl-8-azabicyclo[3.2.1]octane-8-carboxylate

To a solution of (1R,5S,Z)-tert-butyl 3-(methoxymethylene)-8-azabicyclo[3.2.1]octane-8-carboxylate (2.50 g, 9.87 mmol) in CH$_2$Cl$_2$ (30 mL) and water (10 mL) was added trichloroacetic acid (6.45 g, 39.5 mmol). The mixture was stirred at 20-25° C. for 2 h, then the mixture was diluted with water (20 mL) and extracted with DCM (30 mL×3). The combined organic layers were washed with brine (10 mL), dried over Na$_2$SO$_4$, and filtered. The filtrate was concentrated under reduced pressure to afford the title compound, which was used for next step without further purification. MS (ESI) m/z: 240.1 [M+H]$^+$ Step C: (1R,5S)-tert-butyl 3-(7-((1R,2S)-1-cyclopropyl-3-methoxy-2-methyl-3-oxopropyl)-4-oxochroman-2-yl)-8-azabicyclo[3.2.1]octane-8-carboxylate To a solution of (1R,5S)-tert-butyl 3-formyl-8-azabicyclo[3.2.1]octane-8-carboxylate (500 mg, 2.09 mmol), (2S,3R)-methyl 3-(4-acetyl-3-hydroxyphenyl)-3-cyclopropyl-2-methylpropanoate (577 mg, 2.09 mmol) in MeOH (20 mL) was added pyrrolidine (178 mg, 2.51 mmol) at 20-25° C. The reaction mixture was stirred at 60° C. for 2 h, then the mixture was treated with water (10 mL) and ethyl acetate (5 mL). The organic layer was separated. The aqueous layer was extracted with ethyl acetate (5 mL×3). The combined organic layers were dried over anhydrous sodium sulfate, filtered and concentrated under reduced pressure. The resulting crude product was purified by preparative-TLC (silica gel, PE to PE:EtOAc=2:1, v/v) to afford the title compound. MS (ESI) m/z: 498.3 [M+H]$^+$ Step D: (1R,5S)-tert-butyl 3-(7-((1R,2S)-1-cyclopropyl-3-methoxy-2-methyl-3-oxo-propyl)-4-hydroxychroman-2-yl)-8-azabicyclo[3.2.1]octane-8-carboxylate To a solution of (1R,5S)-tert-butyl 3-(7-((1R,2S)-1-cyclopropyl-3-methoxy-2-methyl-3-oxopropyl)-4-oxochroman-2-yl)-8-azabicyclo[3.2.1]octane-8-carboxylate (450 mg, 0.904 mmol) in MeOH (10 mL) was added NaBH$_4$ (103 mg, 2.71 mmol) at 20-25° C. The reaction mixture was stirred at 20-25° C. for 0.5 h. Then the mixture was treated with water (10 mL) and ethyl acetate (10 mL). The organic layer was separated. The aqueous layer was extracted with ethyl acetate (10 mL×3). The combined organic layers were dried over anhydrous sodium sulfate, filtered and concentrated under reduced pressure to afford the title compound. $^1$H NMR (400 MHz, CDCl$_3$): δ=7.37 (d, J=7.9 Hz, 1H), 6.73 (d, J=7.9 Hz, 1H), 6.56 (s, 1H), 5.31 (s, 1H), 4.92 (d, J=6.6 Hz, 1H), 3.84 (br. s., 1H), 3.73 (s, 3H), 2.83-2.73 (m, 1H), 2.26 (dd, J$_1$=6.1, J$_2$=12.0 Hz, 1H), 2.18 (d, J=5.7 Hz, 1H), 2.00 (br. s., 2H), 1.88-1.80 (m, 2H), 1.80-1.63 (m, 7H), 1.49 (s, 9H), 1.02 (br. s., 1H), 0.94 (d, J=6.8 Hz, 3H), 0.55 (br. s., 1H), 0.37-0.19 (m, 2H), 0.00 (br. s., 1H).

Step E: (2S,3R)-methyl 3-(2-((1R,5S)-8-azabicyclo [3.2.1]octan-3-yl)chroman-7-yl)-3-cyclopropyl-2-methylpropanoate To a solution of (1R,5S)-tert-butyl 3-(7-((1R,2S)-1-cyclopropyl-3-methoxy-2-methyl-3-oxopropyl)-4-hydroxychroman-2-yl)-8-azabicyclo-[3.2.1]octane-8-carboxylate (340 mg, 0.680 mmol) in DCM (5.0 mL) was added triethylsilane (1.0 mL, 6.26 mmol) and TFA (1.0 mL, 12.9 mmol) in portions at 20-25° C. under a nitrogen atmosphere. The reaction mixture was stirred at 20-25° C. for 1.5 h, then quenched with saturated NaHCO$_3$ solution (10 mL) at 20-25° C. and extracted with DCM (10 mL×3). The combined organic layers were washed with brine (30 mL), dried over anhydrous MgSO$_4$ and filtered. The filtrate was concentrated in vacuo to give the title compound, which was used for next step without further purification. MS (ESI) m/z: 384.1 [M+H]$^+$ Step F: (2S,3R)-methyl 3-(2-((1R,5S)-8-((S)-1-(2,5-bis(trifluoromethyl)phenyl)ethyl)-8-azabicyclo [3.2.1]octan-3-yl)chroman-7-yl)-3-cyclopropyl-2-methylpropanoate To a solution of (2S,3R)-methyl 3-(2-((1R,5S)-8-azabicyclo[3.2.1]octan-3-yl) chroman-7-yl)-3-cyclopropyl-2-methylpropanoate (70.0 mg, 0.183 mmol) and (R)-1-(2,5-bis(trifluoro methyl)phenyl)ethyl methanesulfonate (92.0 mg, 0.274 mmol) in CH$_3$CN (2.0 mL) was added K$_2$CO$_3$ (76.0 mg, 0.548 mmol) at 20-25° C. The reaction mixture was stirred at 80° C. for 5 h, and then filtered. The filtrate was purified by Prep-HPLC(Column YMC-Actus Pro C18 150*30 5u) to afford the title compound. MS (ESI) m/z: 624.4[M+H]$^+$ Step G: (2S,3R)-3-(2-((1R,5S)-8-((S)-1-(2,5-bis (trifluoromethyl)phenyl)ethyl)-8-aza-bicyclo[3.2.1] octan-3-yl)chroman-7-yl)-3-cyclopropyl-2-methylpropanoic Acid To a solution of (2S,3R)-methyl 3-(2-((1R,5S)-8-((S)-1-(2,5-bis(trifluoromethyl)phenyl)-ethyl)-8-azabicyclo[3.2.1] octan-3-yl)chroman-7-yl)-3-cyclopropyl-2-methylpropanoate (10.0 mg, 0.016 mmol) in THF (1.0 mL), MeOH (1.0 mL) and water (1.0 mL) was added LiOH (3.84 mg, 0.160 mmol) at 20-25° C. The reaction mixture was stirred at 50° C. for 15 h, then the pH of the mixture was adjusted to pH 6 with citric acid. The mixture was filtered and the filtrate was purified by Prep-HPLC(Column Waters XSELECT C18 150*30 mm*5u) to afford the title compound. $^1$H NMR (400 MHz, MeOD): δ=8.09 (br. s., 1H), 7.81 (d, J=8.2 Hz, 1H), 7.72 (d, J=7.8 Hz, 1H), 6.66 (d, J=7.8 Hz, 1H), 6.36-6.24 (m, 2H), 4.34 (br. s., 1H), 4.25 (d, J=5.1 Hz, 1H), 3.54 (br. s., 1H), 3.38 (br. s., 1H), 2.56-2.34 (m, 3H), 2.03-1.64 (m, 8H), 1.59-1.39 (m, 7H), 0.74 (br. s., 1H), 0.59 (d, J=5.5 Hz, 3H), 0.26 (br. s., 1H), −0.01 (d, J=5.1 Hz, 2H), 0.36 (br. s., 1H). MS (ESI) m/z: 610.2[M+H]$^+$

TABLE 3

The compounds of Examples 14-15 were prepared in a similar manner to the procedure of Example 12 using the appropriate intermediates and commerically available starting materials.

| Example | Structure | M.W. | Compound Name | LC/MS (ESI) observed [M + H]$^+$ |
|---|---|---|---|---|
| 14 | 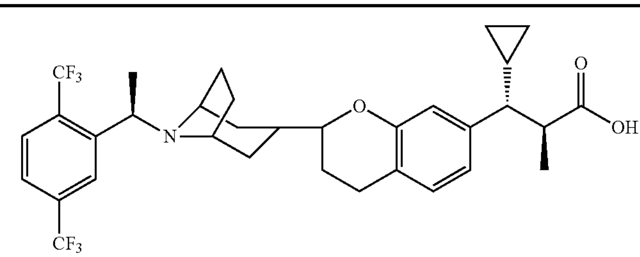 | 609.6 | (2S,3R)-3-(2-((1R,5S)-8-((R)-1-(2,5-bis(trifluoromethyl)phenyl)ethyl)-8-azabicyclo[3.2.1]octan-3-yl)chroman-7-yl)-3-cyclopropyl-2-methyl-propanoic acid | 610.2 |
| 15 | 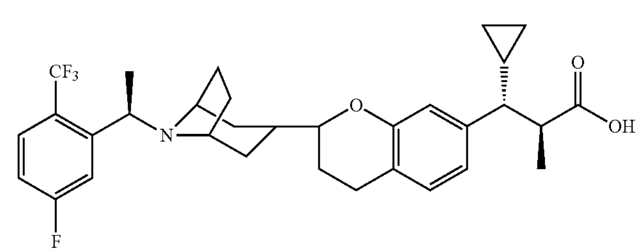 [SMILES: C[C@H](C(=O)O)[C@H](c1ccc2c(c1)OC(C1CC3CCC(C1)N3[C@H](C)c1cc(F)ccc1C(F)(F)F)CC2)C1CC1] | 559.6 | (2S,3R)-3-cyclopropyl-3-(2-((1R,5S)-8-((R)-1-(5-fluoro-2-(trifluoromethyl)-phenyl)ethyl)-8-aza-bicyclo[3.2.1]octan-3-yl)chroman-7-yl)-2-methylpropanoic acid | 560.2 |

Example 14
¹H NMR (400 MHz, MeOD): δ=8.38 (br. s., 1H), 8.11 (d, J=8.2 Hz, 1H), 8.05-7.99 (m, 1H), 6.97 (d, J=7.8 Hz, 1H), 6.68-6.54 (m, 2H), 4.64 (br. s., 1H), 4.56 (br. s., 1H), 3.84 (br. s., 1H), 3.68 (br. s., 1H), 2.90-2.64 (m, 3H), 2.32-1.94 (m, 8H), 1.93-1.68 (m, 7H), 1.04 (br. s., 1H), 0.89 (d, J=5.9 Hz, 3H), 0.57 (br. s., 1H), 0.29 (d, J=5.1 Hz, 2H), −0.06 (br. s., 1H).
Example 15
¹H NMR (400 MHz, MeOD): δ=7.68-7.60 (m, 1H), 7.48 (br. s., 1H), 7.14 (t, J=7.8 Hz, 1H), 6.66 (d, J=7.4 Hz, 1H), 6.35-6.26 (m, 2H), 4.31 (br. s., 1H), 4.18 (d, J=5.5 Hz, 1H), 3.55 (d, J=9.4 Hz, 1H), 3.43 (br. s., 1H), 2.58-2.36 (m, 4H), 2.18-1.79 (m, 3H), 1.78-1.64 (m, 3H), 1.55 (br. s., 2H), 1.45 (d, J=6.3 Hz, 6H), 0.74 (br. s., 1H), 0.58 (br. s., 3H), 0.27 (br. s., 2H), −0.01 (d, J=6.7 Hz, 2H), −0.36 (d, J=4.3 Hz, 1H).
Example 16
(2S,3R)-3-(2-((1S,4S)-2-((S)-1-(2,5-bis(trifluoromethyl)phenyl)ethyl)-2-aza-bicyclo-[2.2.1]heptan-5-yl)chroman-7-yl)-3-cyclopropyl-2-methylpropanoic Acid
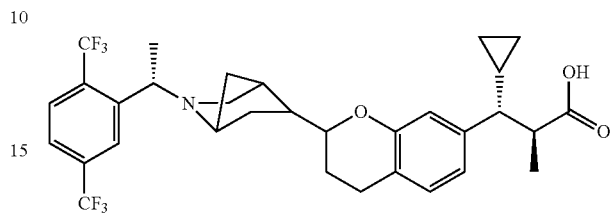
SCHEME 5
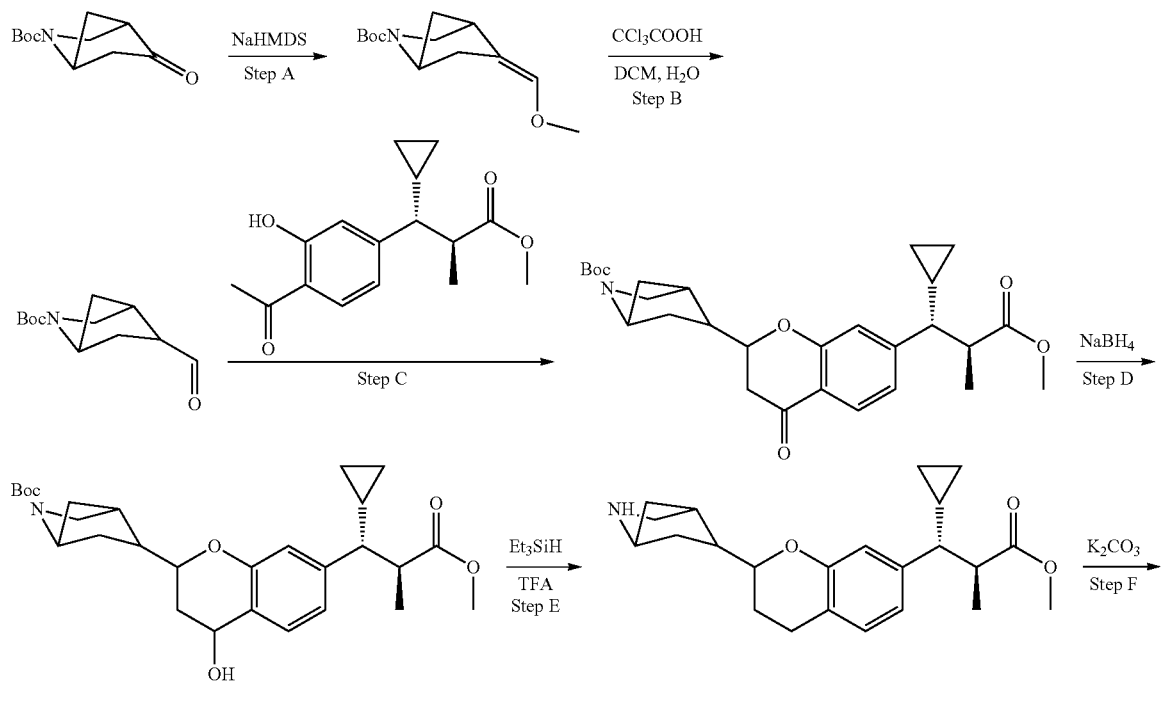
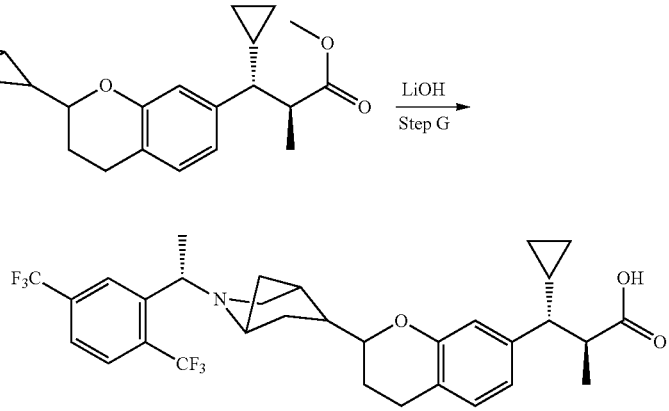

Step A: (1S,4S,E)-tert-butyl 5-(methoxymethylene)-2-azabicyclo[2.2.1]heptane-2-carboxylate To a solution of (methoxymethyl)triphenylphosphonium chloride (4.06 g, 11.8 mmol) in THF (50 mL) was added dropwise NaHMDS (11.8 ml, 11.8 mmol) at 0° C. under nitrogen. The reaction mixture was stirred at 0° C. for 1.5 h. Then a solution of (1S,4R)-tert-butyl 5-oxo-2-azabicyclo[2.2.1]heptane-2-carboxylate (1.0 g, 4.73 mmol) in THF (20 mL) was added dropwise at 0° C. The reaction mixture was stirred at 0° C. for 1 h and at 25° C. for 1.5 h. Then the reaction mixture was diluted with water (30 mL) and extracted with EtOAc (50 ml×3). The combined organic layers were washed with brine (50 mL×2), dried over $Na_2SO_4$, filtered and concentrated under reduced pressure. The resulting residue was purified by silica gel chromatography eluted with PE:EtOAc ($SiO_2$, 50:1-10:1, v/v) to give the title compound. MS (ESI) m/z: 247.0 [M-56+MeCN+$Na^+$]

Step B: tert-butyl 2-formyl-2-azabicyclo[2.2.1]heptane-5-carboxylate

To a solution of (E)-tert-butyl 5-(methoxymethylene)-2-azabicyclo[2.2.1]heptane-2-carboxylate (100 mg, 0.418 mmol) in DCM (2.0 mL) and water (1.0 mL) was added 2,2,2-trichloroacetic acid (341 mg, 2.08 mmol). The mixture was stirred at 25° C. for 2h, then saturated aqueous $NaHCO_3$ solution was added to adjust the pH of the mixture to pH to ~7. The aqueous layer was separated and extracted with DCM (20 mL×3). The combined organic layers were dried over sodium sulfate and filtered. The filtrate was concentrated in vacuo to give the title compound, which was used for the next step directly without further purification. MS (ESI) m/z: 211.0 [M-56+MeCN+H]$^+$

Step C: (4S)-tert-butyl-5-(7-((1R,2S)-1-cyclopropyl-3-methoxy-2-methyl-3-oxopropyl)-4-oxochroman-2-yl)-2-azabicyclo[2.2.1]heptane-2-carboxylate To a solution of (2S,3R)-methyl 3-(4-acetyl-3-hydroxyphenyl)-3-cyclopropyl-2-methylpropanoate (103 mg, 0.373 mmol) in MeOH (2 mL) were added tert-butyl 2-formyl-2-azabicyclo[2.2.1]heptane-5-carboxylate (84 mg, 0.373 mmol) and pyrrolidine (26.5 mg, 0.373 mmol). The reaction mixture was stirred at 60° C. for 8 h, then concentrated to give a residue, which was purified by prep-TLC($SiO_2$, PE:EtOAc=3:1, v/v) to give the title compound. MS (ESI) m/z: 428.2 [M-56+H]$^+$

Step D: (4S or 4R)-tert-butyl 5-(7-((1R,2S)-1-cyclopropyl-3-methoxy-2-methyl-3-oxo-propyl)-4-hydroxychroman-2-yl)-2-azabicyclo[2.2.1]heptane-2-carboxylate To a solution of (4S)-tert-butyl 5-(7-((1R,2S)-1-cyclopropyl-3-methoxy-2-methyl-3-oxopropyl)-4-oxochroman-2-yl)-2-azabicyclo[2.2.1]heptane-2-carboxylate (100 mg, 0.207 mmol) in EtOH (10 mL) was added $NaBH_4$ (39.1 mg, 1.034 mmol) at 0° C. The mixture was stirred at 25° C. for 1 h, then quenched with water (10 mL) and extracted with EtOAc (20 mL×3). The organic layers were dried over $Na_2SO_4$ and filtered. The filtrate was concentrated and purified by prep-TLC ($SiO_2$, PE:EtOAc=3:1, v/v) to give the title compound. MS (ESI) m/z: 486.3 [M+H]$^+$

Step E: (2S,3R)-methyl 3-(2-((4S)-2-azabicyclo[2.2.1]heptan-5-yl)chroman-7-yl)-3-cyclopropyl-2-methylpropanoate To a solution of (4S)-tert-butyl 5-(7-((1R,2S)-1-cyclopropyl-3-methoxy-2-methyl-3-oxopropyl)-4-hydroxychroman-2-yl)-2-azabicyclo[2.2.1]-heptane-2-carboxylate (80 mg, 0.165 mmol) in DCM (8.0 ml) was added triethylsilane (0.5 mL, 0.165 mmol). TFA (0.5 mL, 6.49 mmol) was added dropwise at 0° C., and the reaction mixture was stirred for 1.5 h at 25° C. Then the reaction mixture was concentrated under reduced pressure. Water (15 mL) was added, followed by the addition of $NaHCO_3$ to adjust the pH of the mixture to pH ~8. The aqueous layer was separated and extracted with EtOAc (10 mL×3). The combined organic layers were washed with water (20 mL) and brine (20 mL), dried over anhydrous $MgSO_4$ and filtered. The filtrate was concentrated under reduced pressure to give the title compound, which was used directly for the next step without further purification. MS (ESI) m/z: 370.3 [M+H]±

Step F: (2S,3R)-methyl 3-(2-(2-(1-(2,5-bis(trifluoromethyl)phenyl)ethyl)-2-azabicyclo[2.2.1]heptan-5-yl)chroman-7-yl)-3-cyclopropyl-2-methylpropanoate To a solution of (2S,3R)-methyl-3-(2-(2-azabicyclo[2.2.1]heptan-5-yl)chroman-7-yl)-3-cyclopropyl-2-methylpropanoate (150 mg, 0.406 mmol) in acetonitrile (5.0 mL) were added (R)-1-(2,5-bis(tri-fluoromethyl)phenyl)ethyl methanesulfonate (273 mg, 0.812 mmol) and $K_2CO_3$ (561 mg, 4.06 mmol). The reaction mixture was stirred at 90° C. for 30 min, then quenched with water (10 mL) and extracted with EtOAc (15 mL×3). The combined organic layers were dried over $Na_2SO_4$ and filtered. The filtrate was concentrated to give a residue, which was purified by prep-TLC (silica gel, PE:EtOAc=5:1, v/v) to give the title compound. MS (ESI) m/z: 610.3 [M+H]$^+$

Step G: (2S,3R)-3-(2-((1 S,4S)-2-((S)-1-(2,5-bis(trifluoromethyl)phenyl)ethyl)-2-azabicyclo[2.2.1]heptan-5-yl)chroman-7-yl)-3-cyclopropyl-2-methyl-propanoic Acid To a solution of (2S,3R)-methyl 3-(2-((1S,4S)-2-((S)-1-(2,5-bis(trifluoromethyl)phenyl)ethyl)-2-azabicyclo-[2.2.1]heptan-5-yl)chroman-7-yl)-3-cyclopropyl-2-methylpropanoate (100 mg, 0.164 mmol) in MeOH (1 mL). THF (1.0 mL) and water (1.0 mL) were added lithium hydroxide (39.3 mg, 1.64 mmol). The reaction mixture was stirred at 50° C. for 7 h, then concentrated to give a residue, which was dissolved in water (10 mL) and EtOAc (20 mL). The pH of the mixture was adjusted to pH ~6 with solid citric acid. Then the mixture was extracted with EtOAc (15 mL×3). The combined organic layers were dried over $Na_2SO_4$ and filtered. The filtrate was concentrated to give residue, which was purified by prep-HPLC to give the title compound. LC-MS(ESI) m/z: 596.2 [M+H]$^+$ 1H NMR (400 MHz, METHANOL-$d_4$) δ=8.26 (s, 1H), 7.89-7.87 (m, 1H), 7.76 (s, 1H), 6.93 (d, J=8.0 Hz, 1H), 6.61 (d, J=7.6 Hz, 1H), 6.54-6.52 (m, 1H), 4.15-4.11 (m, 1H), 3.60-3.55 (m, 1H), 2.82-2.68 (m, 5H), 2.01 (s, 1H), 1.86-1.66 (m, 2H), 1.59-1.28 (m, 5H), 1.22-0.88 (m, 5H), 1.03 (s, 1H), 0.87 (d, J=6.0 Hz, 3H), 0.52 (d, J=4.8 Hz, 1H), 0.31-0.22 (m, 2H), 0.07-0.06 (m, 1H).

TABLE 4

The compounds of Examples 17-21 were prepared in a similar manner to the procedures above using the appropriate intermediates and commercially available starting materials.

| Example | Structure | M.W. | Compound Name | LC/MS (ESI) observed [M + H]+ |
|---|---|---|---|---|
| 17 | 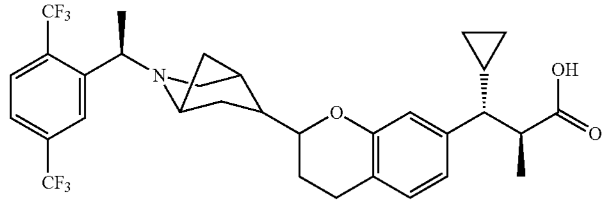 [SMILES: C[C@H](C(=O)O)[C@H](c1ccc2c(c1)OC(C1CC3CC1CN3[C@H](C)c1cc(C(F)(F)F)ccc1C(F)(F)F)CC2)C1CC1] | 595.6 | (2S,3R)-3-(2-((1S,4S)-2-((R)-1-(2,5-bis(trifluoromethyl)-phenyl)ethyl)-2-azabicyclo-[2.2.1]heptan-5-yl)chroman-7-yl)-3-cyclopropyl-2-methyl-propanic acid | 596.3 |
| 18 | 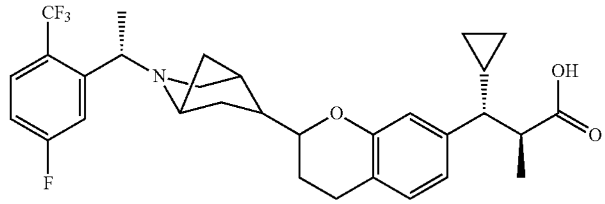 [SMILES: C[C@H](C(=O)O)[C@H](c1ccc2c(c1)OC(C1CC3CC1CN3[C@@H](C)c1cc(F)ccc1C(F)(F)F)CC2)C1CC1] | 545.6 | (2S,3R)-3-cyclopropyl-3-(2-((1S,4S)-2-((S)-1-(5-fluoro-2-(trifluoromethyl)phenyl)ethyl)-2-azabicyclo[2.2.1]heptan-5-yl)chroman-7-yl)-2-methyl-propanoic acid | 546.2 |
| 19 | 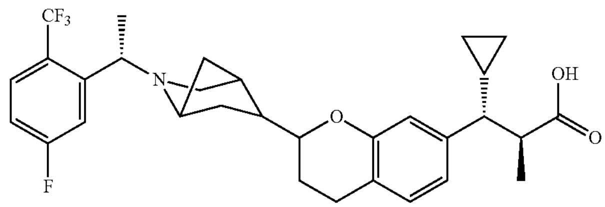 [SMILES: C[C@H](C(=O)O)[C@H](c1ccc2c(c1)OC(C1CC3CC1CN3[C@@H](C)c1cc(F)ccc1C(F)(F)F)CC2)C1CC1] | 545.6 | (2S,3R)-3-cyclopropyl-3-(2-((1S,4S)-2-((S)-1-(5-fluoro-2-(trifluoromethyl)phenyl)ethyl)-2-azabicyclo[2.2.1]heptan-5-yl)chroman-7-yl)-2-methyl-propanic acid | 546.2 |
| 20 | 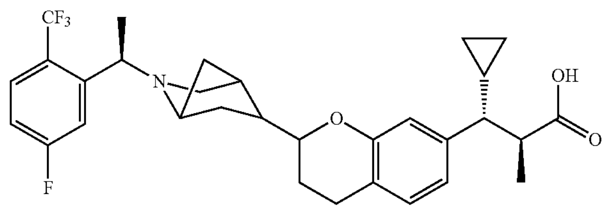 [SMILES: C[C@H](C(=O)O)[C@H](c1ccc2c(c1)OC(C1CC3CC1CN3[C@H](C)c1cc(F)ccc1C(F)(F)F)CC2)C1CC1] | 545.6 | (2S,3R)-3-cyclopropyl-3-(2-((1S,4S)-2-((R)-1-(5-fluoro-2-(trifluoromethyl)phenyl)ethyl)-2-azabicyclo[2.2.1]heptan-5-yl)chroman-7-yl)-2-methylpropanic acid | 546.2 |
| 21 | 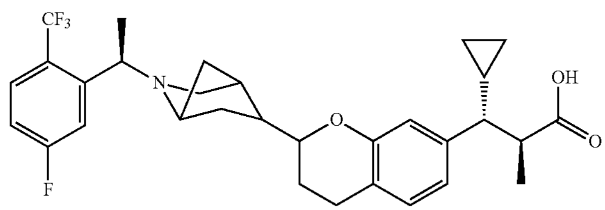 [SMILES: C[C@H](C(=O)O)[C@H](c1ccc2c(c1)OC(C1CC3CC1CN3[C@H](C)c1cc(F)ccc1C(F)(F)F)CC2)C1CC1] | 545.6 | (2S,3R)-3-cyclopropyl-3-(2-((1S,4S)-2-((R)-1-(5-fluoro-2-(trifluoromethyl)phenyl)ethyl)-2-azabicyclo[2.2.1]heptan-5-yl)chroman-7-yl)-2-methyl-propanoic acid | 546.2 |

Example 17

$^1$H NMR (400 MHz, METHANOL-d$_4$) δ=8.26 (s, 1H), 7.92-7.89 (m, 1H), 7.79 (d, J=6.4 Hz, 1H), 6.95 (d, J=8.0 Hz, 1H), 6.63 (d, J=7.6 Hz, 1H), 6.55-6.49 (m, 1H), 4.17-4.12 (m, 1H), 3.68 (d, J=9.2 Hz, 1H), 2.87-2.66 (m, 5H), 2.44 (s., 1H), 2.02 (d, J=8.6 Hz, 2H), 1.85-1.58 (m, 5H), 1.43-1.13 (m, 5H), 1.03 (s, 1H), 0.87 (d, J=6.3 Hz, 3H), 0.54 (d, J=5.1 Hz, 1H), 0.33-0.30 (m, 2H), 0.05-0.04 (m, 1H).

Example 18

$^1$H NMR (400 MHz, METHANOL-d$_4$) δ=7.77-7.68 (m, 2H), 7.21 (s, 1H), 6.94 (d, J=7.6 Hz, 1H), 6.63 (d, J=7.6 Hz, 1H), 6.56 (d, J=8.4 Hz, 1H), 4.17 (s, 1H), 3.83 (d, J=8.4 Hz, 1H), 3.60 (t, J=9.6 Hz, 1H), 3.38 (br. s., 1H), 2.99-2.66 (m, 5H), 2.50 (s, 1H), 2.04 (d, J=7.9 Hz, 2H), 1.85 (br. s., 2H), 1.71 (br. s., 2H), 1.48 (d, J=9.5 Hz, 2H), 1.40-1.22 (m, 2H), 1.05 (s, 1H), 0.91-0.84 (m, 3H), 0.55 (br. s., 1H), 0.33 (d, J=4.2 Hz, 1H), 0.27-0.25 (m, 1H), 0.07-0.06 (m, 1H).

Example 19

$^1$H NMR (400 MHz, METHANOL-d$_4$) δ=7.76-7.66 (m, 2H), 7.19 (s, 1H), 6.96 (d, J=7.7 Hz, 1H), 6.63 (d, J=7.3 Hz, 1H), 6.58-6.53 (m, 1H), 4.61 (s, 1H), 4.15 (s, 1H), 4.03-3.93 (m, 1H), 2.85-2.83 (m, 4H), 2.70 (s, 2H), 2.14 (s, 1H), 1.87

(br. s., 2H), 1.82-1.44 (m, 4H), 1.34 (br. s., 4H), 1.06 (br. s., 1H), 0.87 (d, J=6.8 Hz, 3H), 0.55 (br. s., 1H), 0.32 (d, J=4.4 Hz, 2H), 0.05-0.02 (m, 1H).

Example 20

¹H NMR (400 MHz, METHANOL-d₄) δ=7.96 (d, J=6.0 Hz, 1H), 7.69 (s, 1H), 7.45 (d, J=7.6 Hz, 1H), 7.98-7.96 (m, 1H), 6.65-6.49 (m, 2H), 4.67 (s, 1H), 3.61 (s, 2H), 3.31-3.13 (m, 2H), 2.85-2.70 (m, 4H), 2.08-1.68 (m, 11H), 1.05 (s, 1H), 0.90 (d, J=5.6 Hz, 3H), 0.60 (d, J=6.3 Hz, 3H), 0.33-0.31 (br. s., 1H), 0.03 (d, J=5.5 Hz, 2H), 0.06-0.05 (m, 1H).

Example 21

¹H NMR (400 MHz, METHANOL-d₄) δ=7.82 (d, J=5.7 Hz, 1H), 7.74 (br. s., 1H), 7.28 (br. s., 1H), 6.97 (s, 1H), 6.65 (d, J=7.5 Hz, 1H), 6.56 (s, 1H), 4.61 (br. s., 1H), 4.35 (br. s., 1H), 4.02 (d, J=11.7 Hz, 1H), 3.38 (br. s., 2H), 2.91 (br. s., 2H), 2.69 (br. s., 3H), 2.25-2.18 (m, 1H), 1.99 (br. s., 2H), 1.85 (br. s., 3H), 1.67 (br. s., 2H), 1.45 (br. s., 3H), 1.09-1.02 (m, 1H), 0.88 (s, 3H), 0.58-0.55 (m, 1H), 0.33-0.31 (m, 2H), 0.04-0.03 (m., 1H).

Scheme 6

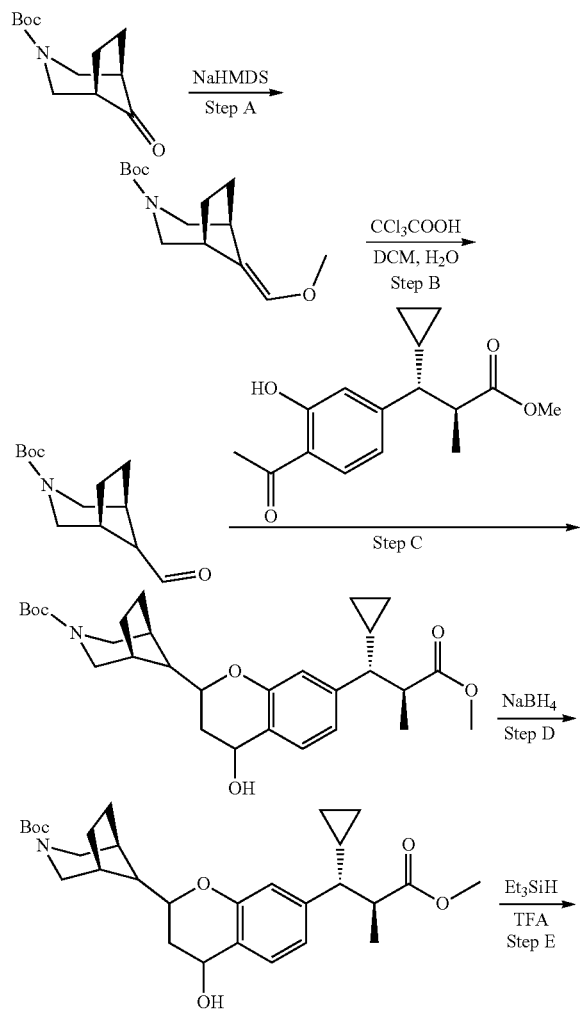

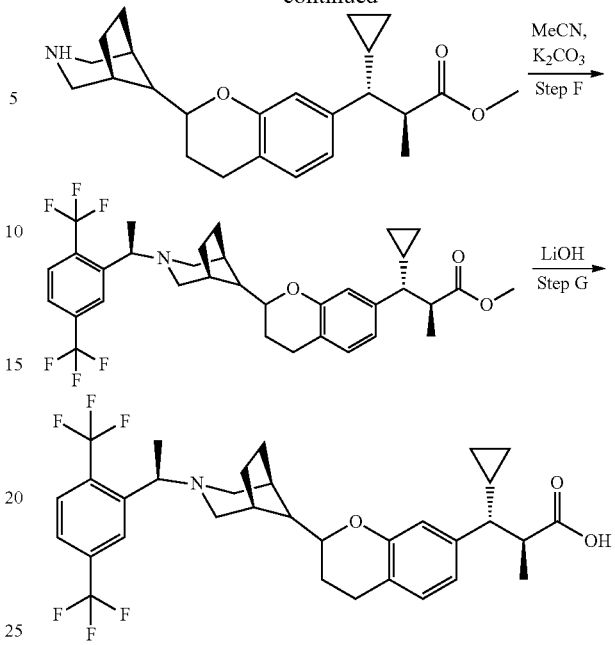

Example 22 and Example 23

(2S,3R)-3-(2-((1R,5S)-3-((R)-1-(2,5-bis(trifluoromethyl)phenyl)ethyl)-3-azabicyclo[3.2.1]octan-8-yl)chroman-7-yl)-3-cyclopropyl-2-methylpropanoic Acid

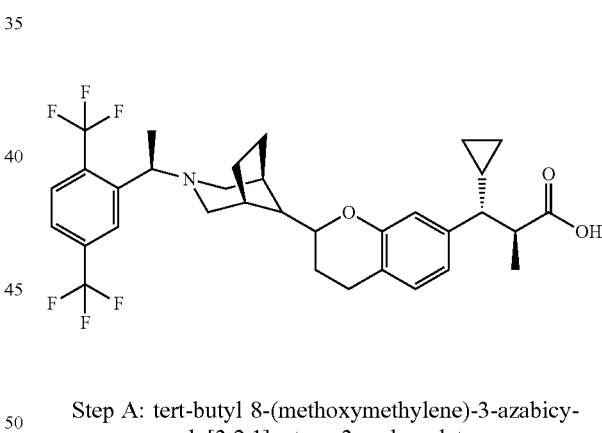

Step A: tert-butyl 8-(methoxymethylene)-3-azabicyclo[3.2.1]octane-3-carboxylate

To a solution of (methoxymethyl)triphenylphosphonium chloride (4.56 g, 13.3 mmol) in THF (50 mL) was added dropwise NaHMDS (13.3 mL, 13.3 mmol) at 0° C. under nitrogen. The mixture was stirred at 0° C. for 1.5 h. Then a solution of tert-butyl 8-oxo-3-azabicyclo-[3.2.1]-octane-3-carboxylate (2.00 g, 8.88 mmol) in THF (20 mL) was added dropwise at 0° C. to the mixture. The reaction mixture was stirred at 0° C. for 1 h and then at 25° C. for 1.5 h. Then the mixture was diluted with water (100 mL) and extracted with EtOAc (100 ml×2). The combined organic layers were washed with brine (150 ml×2), dried over Na₂SO₄ and filtered. The filtrate was concentrated under reduced pressure. The resulting residue was purified by silica gel chromatography eluted with PE/EtOAc (SiO₂, PE:EtOAc=50:1-10:1, v/v) to give the title compound. MS (ESI) m/z: 239.1

[M-56+MeCN+H]+ 1H NMR (400 MHz, CHLOROFORM-d) δ=5.86 (s, 1H), 4.04-3.99 (m, 1H), 3.90-3.82 (m, 1H), 3.57 (s, 1H), 3.00-2.78 (m, 3H), 2.43-2.37 (m, 1H), 1.65-1.58 (m, 3H), 1.46 (s, 10H).

Step B: tert-butyl 8-formyl-3-azabicyclo[3.2.1]octane-3-carboxylate

To a solution of tert-butyl 8-(methoxymethylene)-3-azabicyclo[3.2.1]octane-3-carboxylate (1.70 g, 6.71 mmol) in DCM (20 mL) and water (10 mL) was added trichloroacetic acid (6.58 g, 40.3 mmol). The mixture was stirred for 6 h at 20° C. Then the mixture was diluted with water (50 mL) and was extracted with DCM (40 mL×3). The combined organic layers were washed with brine (100 mL×2), dried over Na$_2$SO$_4$ and filtered. The filtrate was concentrated under reduced pressure. The resulting residue was purified by silica gel chromatography eluted with PE/EtOAc (SiO$_2$, PE:EtOAc=50: 1-10:1, v/v) to give the title compound. MS (ESI) m/z: 225.1 [M-56+MeCN+H]+1H NMR (400 MHz, CHLOROFORM-d) δ=9.63 (s, 1H), 4.03-4.00 (m, 1H), 3.90-3.86 (m, 1H), 2.94-2.84 (m, 2H), 2.77 (br.s, 4H), 2.63 (s, 1H), 2.57 (s, 1H), 2.43 (s, 1H), 1.60-1.53 (m, 1H), 1.47-1.46 (s, 9H).

Step C: (1R,5S,8r)-tert-butyl 8-((RS)-7-((1R,2S)-1-cyclopropyl-3-methoxy-2-methyl-3-oxopropyl)-4-oxochroman-2-yl)-3-azabicyclo[3.2.1]octane-3-carboxylate Tert-butyl 8-formyl-3-azabicyclo[3.2.1]octane-3-carboxylate (857 mg, 3.58 mmol) and (2S,3R)-methyl 3-(4-acetyl-3-hydroxyphenyl)-3-cyclopropyl-2-methylpropanoate (900 mg, 3.26 mmol) were combined in dry MeOH (15 mL), and pyrrolidine (0.323 mL, 3.91 mmol) was added. The reaction was heated to 60° C. for 3h, then the MeOH was removed under reduced pressure. The resulting residue was diluted with H$_2$O (30 mL), extracted with EtOAc (25 mL×3). The combined organic layers were washed brine (30 mL), dried over anhydrous MgSO$_4$ and filtered. The filtrate was concentrated under reduced pressure. The resulting residue was purified by silica gel chromagraphy eluted with PE/EtOAc (SiO$_2$, PE:EtOAc=50: 1-10:1, v/v) to give the title compound. MS (ESI) m/z: 442.2 [M-56+MeCN+H]+1H NMR (400 MHz, CHLOROFORM-d) δ=7.82 (d, J=7.9 Hz, 1H), 6.93-6.71 (m, 2H), 4.10-3.81 (m, 3H), 3.74 (s, 3H), 2.99-2.57 (m, 6H), 2.17-2.07 (m, 1H), 2.03-1.89 (m, 2H), 1.87-1.69 (m, 1H), 1.69-1.61 (m, 2H), 1.59-1.55 (m, 1H), 1.46 (s, 9H), 1.05 (br. s., 1H), 0.96 (d, J=6.8 Hz, 3H), 0.65-0.54 (m, 1H), 0.42-0.22 (m, 2H), 0.09-0.06 (m, 1H).

Step D: (1R,5S,8s)-tert-butyl 8-((2RS)-7-((1R,2S)-1-cyclopropl-3-methoxy-2-methyl-3-oxopropyl)-4-hydroxychroman-2-yl)-3-azabicyclo[3.2.1]octane-3-carboxylate To a solution of ((1R,5S,8r)-tert-butyl 8-((RS)-7-((1R, 2S)-1-cyclopropyl-3-methoxy-2-methyl-3-oxo-propyl)-4-oxochroman-2-yl)-3-azabicyclo[3.2.1]octane-3-carboxylate (900 mg, 1.81 mmol) in EtOH (15 ml) was added NaBH$_4$ (137 mg, 3.62 mmol) in portions at 25° C. under N$_2$ atmosphere. The reaction mixture was stirred for 1.5 h at 25° C. Then the reaction was quenched with saturated NH$_4$Cl solution (30 mL) at 25° C. and extracted with EtOAc (20 mL×3). The combined organic layers were washed with brine (30 mL), dried over anhydrous MgSO$_4$ and filtered. The filtrate was concentrated in vacuo to give the title compound, which was used directly for the next step without further purification. MS (ESI) m/z: 500.2 [M+H]+

Step E: (2S,3R)-methyl 3-((RS)-2-((1R,5S,8s)-3-azabicyclo[3.2.1]octan-8-yl)chroman-7-yl)-3-cyclopropyl-2-methylpropanoate To a solution of (1R,5S,8s)-tert-butyl 8-((2RS)-7-((1R, 2S)-1-cyclopropyl-3-methoxy-2-methyl-3-oxopropyl)-4-hydroxychroman-2-yl)-3-azabi-cyclo[3.2.1]octane-3-carboxylate (890 mg, 1.78 mmol) in DCM (8.0 mL) was added triethylsilane (2.0 mL, 1.78 mmol). Then TFA (2.0 mL, 26.0 mmol) was added dropwise at 0° C. under N$_2$ atmosphere. The reaction mixture was stirred for 1.5 h at 25° C., then concentrated under reduced pressure. Water (15 mL) was added to the mixture, followed by the addition of NaHCO$_3$ solid to adjust the mixture pH to pH=7-8. The aqueous phase was separated, and extracted with EtOAc (10 mL×3). The combined organic layers were washed with water (20 mL) and brine (20 mL), dried over anhydrous MgSO$_4$ and filtered. The filtrate was concentrated under reduced pressure to give the title compound, which was used directly for the next step without further purification. MS (ESI) m/z: 384.3 [M+H]+

Step F: (2S,3R)-methyl 3-((2RS)-2-((1R,5S)-3-((R)-1-(2,5-bis(trifluoromethyl)phenyl)-ethyl)-3-azabicyclo[3.2.1]octan-8-yl)chroman-7-yl)-3-cyclopropyl-2-methylpropanoate To a solution of (2S,3R)-methyl 3-((RS)-2-((1R,5S,8s)-3-azabicyclo[3.2.1]octan-8-yl)chroman-7-yl)-3-cyclopropyl-2-methylpropanoate (150 mg, 0.391 mmol) in MeCN (5.0 mL) was added sodium iodide (176 mg, 1.17 mmol), K$_2$CO$_3$ (270 mg, 1.96 mmol) and (S)-1-(2,5-bis-(trifluoromethyl)phenyl)ethyl methanesulfonate (158 mg, 0.469 mmol) under N$_2$ atmosphere. The reaction mixture was stirred for 3.5 h at 90° C. Then water (15 mL) was added to the mixture and the mixture was extracted with EtOAc (10 mL×3). The combined organic layers were washed with brine (20 mL), dried over anhydrous MgSO$_4$ and filtered. The filtrate was concentrated in vacuo to give a residue, which was purified by pre-TLC (SiO$_2$, PE/EtOAc=10:1, v/v)) to give the title compound. MS (ESI) m/z: 624.4 [M+H]+

Step G: (2S,3R)-3-((RS)-2-((1R,5S,8r)-3-((R)-1-(2, 5-bis(trifluoromethyl)phenyl)ethyl)-3-azabicyclo [3.2.1]octan-8-yl)chroman-7-yl)-3-cyclopropyl-2-methylpropanoic Acid To a solution of compound (2S,3R)-methyl 3-((2RS)-2-((1R,5S)-3-((R)-1-(2,5-bis-(trifluoro methyl)phenyl)ethyl)-3-azabicyclo[3.2.1]octan-8-yl)chroman-7-yl)-3-cyclopropyl-2-methyl propanoate (155 mg, 0.249 mmol) in a co-solvent of THF/MeOH/H$_2$O (2.0 mL/2.0 mL/2.0 mL) was added lithium hydroxide monohydrate (104 mg, 2.49 mmol) under nitrogen. The reaction mixture was stirred at 50° C. for 20 h, then the reaction mixture was concentrated in vacuo to remove the solvent. Water (5.0 mL) was added to the resulting residue, and citric acid was added to adjust the pH of the solution to pH-5. Then the solution was extracted with EtOAc (5 mL×3). The combined organic layers were washed with brine (5.0 mL), dried over anhydrous MgSO$_4$ and filtered. The filtrate was concentrated under reduced pressure. The resulting residue was purified by Prep HPLC (neutral) to give: Example 22—the first peak (2S,3R)-methyl 3-((2RS)-2-((1R,5S)-3-((R)-1-(2,5-bis-(trifluoromethyl)-phenyl)ethyl)-3-azabicyclo[3.2.1]-octan-8-yl) chroman-7-yl)-3-cyclopropyl-2-methylpropanoate; and Example 23—the second peak (2S,3R)-methyl 3-((2RS)-2-((1R,5S)-3-((R)-1-(2,5-bis(trifluoromethyl)phenyl)ethyl)-3-azabicyclo[3.2.1]octan-8-yl)chroman-7-yl)-3-cyclopropyl-2-methylpropanoate. Prep HPLC conditions:Preparative HPLC on a MS trigger instrument fitted with a Phenomenex Synergi C18 250*21.2 mm*4 um; mobile phase A: water (10M NH$_4$HCO$_3$); mobile phase B: acetonitrile; gradient: 50-80% B, 0-12.0 min; 100% B, 12.0-14.0 min; FlowRate: 25 mL/min.

To a solution of the Example 22 in MeCN (1.0 mL) and water (1.0 mL) was added an aqueous solution of NaOH (1.0 eq, 0.5 M), and the mixture was stirred for 1 h at room temperature (25° C.). Then the reaction mixture was lyophilized to give the sodium salt of the title compound. Na salt of Example 22: MS (ESI) m/z: 610.2 [M+H]$^+$ 1H NMR (400 MHz, methanol-d$_4$): δ=8.33-8.25 (m, 1H), 7.84 (d, J=8.2 Hz, 1H), 7.71 (d, J=8.0 Hz, 1H), 6.95 (d, J=7.8 Hz, 1H), 6.66-6.51 (m, 2H), 4.64-4.47 (m, 1H), 3.84-3.72 (m, 1H), 3.72-3.60 (m, 1H), 3.38-3.33 (m, 1H), 3.30-3.22 (m, 2H), 2.84-2.64 (m, 3H), 2.38-2.28 (m, 1H), 2.28-2.19 (m, 1H), 2.15-2.03 (m, 1H), 2.02-1.80 (m, 4H), 1.73-1.49 (m, 3H), 1.30 (d, J=6.3 Hz, 3H), 1.16-1.00 (m, 1H), 0.91 (d, J=6.7 Hz, 3H), 0.62-0.50 (m, 1H), 0.38-0.24 (m, 2H), 0.04-0.08 (m, 1H).

To a solution of the Example 23 in MeCN (1.0 mL) and water (1.0 mL) was added an aqueous solution of NaOH (1.0 eq, 0.5 M), and the mixture was stirred for 1 h at room temperature (25° C.). Then the reaction mixture was lyophilized to give the sodium salt of the title compound. Na salt of Example 23: MS (ESI) m/z: 610.2 [M+H]$^+$ 1H NMR (400 MHz, methanol-d$_4$): δ=8.31 (br. s., 1H), 7.84 (d, J=8.2 Hz, 1H), 7.71 (d, J=8.2 Hz, 1H), 6.95 (d, J=7.8 Hz, 1H), 6.65-6.55 (m, 1H), 6.52 (s, 1H), 4.59 (br. s., 1H), 3.82-3.73 (m, 1H), 3.72-3.62 (m, 1H), 3.37-3.34 (m, 1H), 3.28-3.21 (m, 1H), 2.86-2.64 (m, 3H), 2.44 (br. s., 1H), 2.40-2.20 (m, 2H), 2.20-2.10 (m, 1H), 2.00-1.78 (m, 2H), 1.77-1.51 (m, 4H), 1.29 (d, J=5.9 Hz, 4H), 1.11-0.97 (m, 1H), 0.88 (d, J=7.0 Hz, 3H), 0.60-0.48 (m, 1H), 0.39-0.16 (m, 2H), 0.00-0.11 (m, 1H).

TABLE 5

The compounds of Examples 24-31 were prepared in a similar manner to the procedure of Example 22 using the appropriate intermediates and commercially available starting materials.

| Example | Structure | M.W. | Compound Name | LC/MS (ESI) observed [M + 1]+ |
| --- | --- | --- | --- | --- |
| 24 | 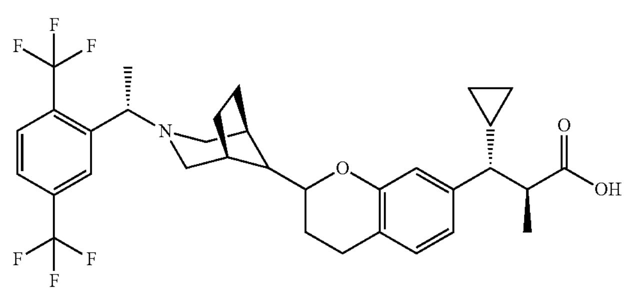 [SMILES: C[C@H](C(=O)O)[C@H](c1ccc2c(c1)OC(C1[C@@H]3CC[C@@H]1CN([C@@H](C)c1cc(C(F)(F)F)ccc1C(F)(F)F)C3)CC2)C1CC1] | 609.64 | (2S,3R)-methyl 3-((2RS)-2-((1R,5S)-3-((S)-1-(2,5-bis(trifluoromethyl)phenyl)ethyl)-3-azabicyclo[3.2.1]-octan-8-yl)chroman-7-yl)-3-cyclopropyl-2-methyl-propanoic acid | 610.2 |
| 25 | 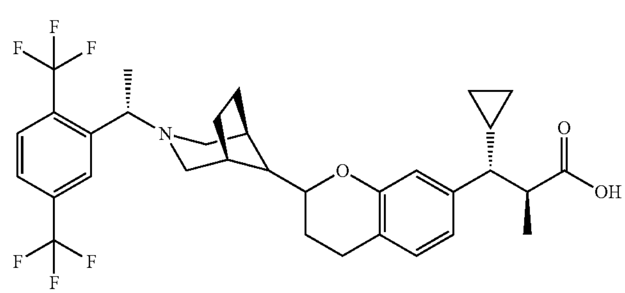 [SMILES: C[C@H](C(=O)O)[C@H](c1ccc2c(c1)OC(C1[C@@H]3CC[C@@H]1CN([C@@H](C)c1cc(C(F)(F)F)ccc1C(F)(F)F)C3)CC2)C1CC1] | 609.64 | (2S,3R)-methyl 3-((2RS)-2-((1R,5S)-3-((S)-1-(2,5-bis(trifluoromethyl)phenyl)ethyl)-3-azabicyclo[3.2.1]-octan-8-yl)chroman-7-yl)-3-cyclopropyl-2-methyl-propanoic acid | 610.2 |
| 26 | 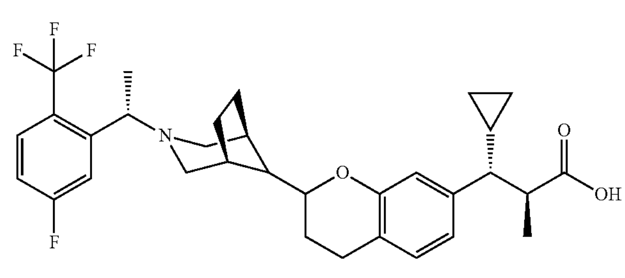 [SMILES: C[C@H](C(=O)O)[C@H](c1ccc2c(c1)OC(C1[C@@H]3CC[C@@H]1CN([C@@H](C)c1cc(F)ccc1C(F)(F)F)C3)CC2)C1CC1] | 559.63 | (2S,3R)-3-cyclopropyl-3-((2RS)-2-((1R,5S)-3-((S)-1-(5-fluoro-2-(trifluoromethyl)phenyl)ethyl)-3-azabicyclo[3.2.1]-octan-8-yl)chroman-7-yl)-2-methylpropanoic acid | 560.2 |

TABLE 5-continued

The compounds of Examples 24-31 were prepared in a similar manner to the procedure of Example 22 using the appropriate intermediates and commercially available starting materials.

| Example | Structure | M.W. | Compound Name | LC/MS (ESI) observed [M + 1]+ |
|---|---|---|---|---|
| 27 | 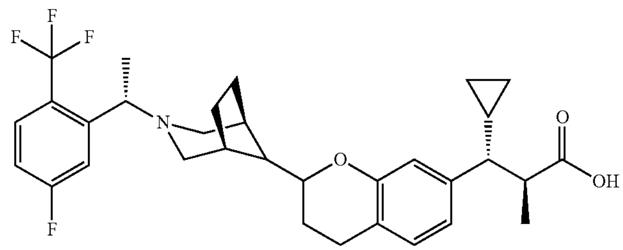 [SMILES: C[C@H](C(=O)O)[C@H](c1ccc2c(c1)OC(C1[C@@H]3CC[C@@H]1CN([C@@H](C)c1cc(F)ccc1C(F)(F)F)C3)CC2)C1CC1] | 559.63 | (2S,3R)-3-cyclopropyl-3-((2R or 2S)-2-((1R,5S)-3-((S)-1-(5-fluoro-2-(trifluoromethyl)phenyl)ethyl)-3-azabicyclo[3.2.1]-octan-8-yl)chroman-7-yl)-2-methylpropanoic acid | 560.2 |
| 28 | 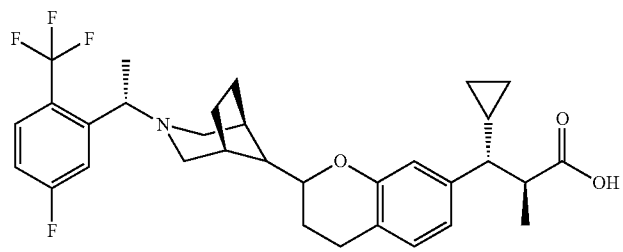 [SMILES: C[C@H](C(=O)O)[C@H](c1ccc2c(c1)OC(C1[C@@H]3CC[C@@H]1CN([C@@H](C)c1cc(F)ccc1C(F)(F)F)C3)CC2)C1CC1] | 559.63 | (2S,3R)-3-cyclopropyl-3-((2R or 2S)-2-((1R,5S)-3-((S)-1-(5-fluoro-2-(trifluoromethyl)phenyl)ethyl)-3-azabicyclo[3.2.1]-octan-8-yl)chroman-7-yl)-2-methylpropanoic acid | 560.2 |
| 29 | 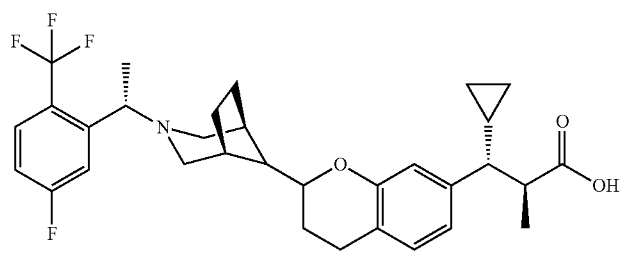 [SMILES: C[C@H](C(=O)O)[C@H](c1ccc2c(c1)OC(C1[C@@H]3CC[C@@H]1CN([C@@H](C)c1cc(F)ccc1C(F)(F)F)C3)CC2)C1CC1] | 559.63 | (2S,3R)-3-cyclopropyl-3-((2RS)-2-((1R,5S)-3-((S)-1-(5-fluoro-2-(trifluoromethyl)phenyl)ethyl)-3-azabicyclo[3.2.1]-octan-8-yl)chroman-7-yl)-2-methylpropanoic acid | 560.2 |
| 30 | 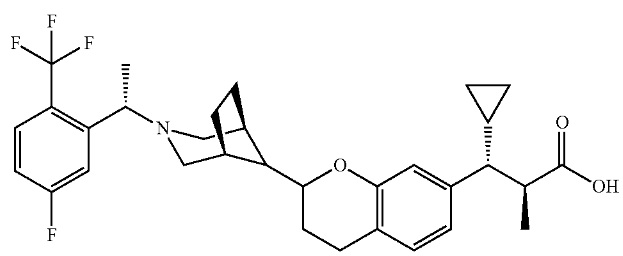 [SMILES: C[C@H](C(=O)O)[C@H](c1ccc2c(c1)OC(C1[C@@H]3CC[C@@H]1CN([C@@H](C)c1cc(F)ccc1C(F)(F)F)C3)CC2)C1CC1] | 559.63 | (2S,3R)-3-cyclopropyl-3-((2R or 2S)-2-((1R,5S)-3-((S)-1-(5-fluoro-2-(trifluoromethyl)phenyl)ethyl)-3-azabicyclo[3.2.1]-octan-8-yl)chroman-7-yl)-2-methylpropanoic acid | 560.2 |
| 31 | 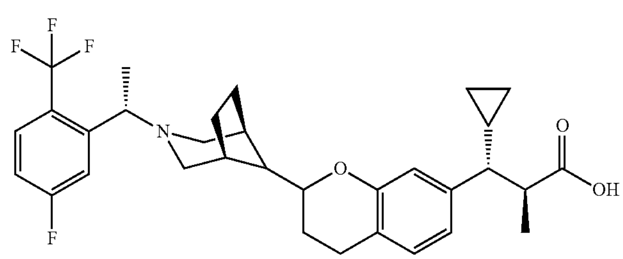 [SMILES: C[C@H](C(=O)O)[C@H](c1ccc2c(c1)OC(C1[C@@H]3CC[C@@H]1CN([C@@H](C)c1cc(F)ccc1C(F)(F)F)C3)CC2)C1CC1] | 559.63 | (2S,3R)-3-cyclopropyl-3-((2R or 2S)-2-((1R,5S)-3-((S)-1-(5-fluoro-2-(trifluoromethyl)phenyl)ethyl)-3-azabicyclo[3.2.1]-octan-8-yl)chroman-7-yl)-2-methylpropanoic acid | 560.2 |

Example 24

MS (ESI) m/z: 610.2 [M+H]+ 1H NMR (400 MHz, METHANOL-d$_4$): δ=8.30 (br. s., 1H), 7.84 (d, J=8.2 Hz, 1H), 7.71 (d, J=8.2 Hz, 1H), 6.95 (d, J=7.4 Hz, 1H), 6.68-6.50 (m, 2H), 4.58 (br. s., 1H), 3.90-3.72 (m, 1H), 3.72-3.60 (m, 1H), 3.35 (br. s., 2H), 3.28-3.25 (m, 1H), 2.80-2.70 (m, 3H), 2.37-2.28 (m, 1H), 2.28-2.20 (m, 1H), 2.15-2.04 (m, 3H), 2.04-1.93 (m, 2H), 1.92-1.79 (m, 2H), 1.72-1.64 (m, 1H), 1.64-1.51 (m, 2H), 1.30 (d, J=6.3 Hz,

3H), 1.14-1.00 (m, 1H), 0.91 (d, J=6.7 Hz, 3H), 0.64-0.48 (m, 1H), 0.38-0.24 (m, 2H), 0.06-0.09 (m, 1H).

Example 25

MS (ESI) m/z: 610.2 [M+H]+ 1H NMR (400 MHz, METHANOL-d4): δ=8.31 (s, 1H), 7.84 (d, J=7.8 Hz, 1H), 7.71 (d, J=8.2 Hz, 1H), 6.95 (d, J=7.4 Hz, 1H), 6.61 (d, J=7.4 Hz, 1H), 6.52 (s, 1H), 4.58 (br. s., 1H), 3.82-3.72 (m, 1H), 3.72-3.63 (m, 1H), 3.35 (br. s., 1H), 3.28-3.21 (m, 1H), 2.86-2.74 (m, 2H), 2.73-2.63 (m, 1H), 2.44 (br. s., 1H), 2.37-2.35 (m, 1H), 2.30-2.25 (m, 2H), 2.20-2.11 (m, 1H), 1.99-1.88 (m, 2H), 1.83 (t, J=9.8 Hz, 1H), 1.78-1.71 (m, 1H), 1.70-1.65 (m, 1H), 1.63-1.55 (m, 1H), 1.29 (d, J=5.9 Hz, 3H), 1.11-0.97 (m, 1H), 0.88 (d, J=6.7 Hz, 3H), 0.60-0.49 (m, 1H), 0.32-0.21 (m, 2H), 0.01--0.10 (m, 1H).

Example 26

MS (ESI) m/z: 560.2 [M+H]+ 1H NMR (400 MHz, METHANOL-d4): δ=7.67 (d, J=9.5 Hz, 2H), 7.12 (br. s., 1H), 6.94 (d, J=7.7 Hz, 1H), 6.63-6.52 (m, 2H), 3.75-3.62 (m, 2H), 3.28-3.15 (m, 1H), 2.87-2.63 (m, 4H), 2.53-2.37 (m, 1H), 2.36-2.03 (m, 3H), 2.02-1.79 (m, 4H), 1.75-1.55 (m, 4H), 1.26 (d, J=6.0 Hz, 3H), 1.15-1.00 (m, 1H), 0.92-0.87 (m, 3H), 0.63-0.50 (m, 1H), 0.35-0.25 (m, 2H), 0.03-0.12 (m, 1H).

Example 27

MS (ESI) m/z: 560.2 [M+H]+ 1H NMR (400 MHz, METHANOL-d4): δ=7.72-7.61 (m, 2H), 7.12 (t, J=6.8 Hz, 1H), 6.95 (d, J=7.8 Hz, 1H), 6.67-6.50 (m, 2H), 3.81-3.57 (m, 2H), 3.26-3.21 (m, 1H), 3.01-2.64 (m, 4H), 2.55-2.01 (m, 4H), 2.01-1.77 (m, 4H), 1.77-1.54 (m, 4H), 1.31-1.21 (m, 3H), 1.15-1.01 (m, 1H), 0.96-0.86 (m, 3H), 0.63-0.51 (m, 1H), 0.37-0.24 (m, 2H), 0.03-0.10 (m, 1H).

Example 28

MS (ESI) m/z: 560.2 [M+H]+ 1H NMR (400 MHz, METHANOL-d4): δ=7.67 (d, J=8.6 Hz, 2H), 7.18-7.10 (m, 1H), 6.95 (d, J=7.8 Hz, 1H), 6.61 (d, J=7.4 Hz, 1H), 6.52 (s, 1H), 3.75-3.60 (m, 2H), 3.23-3.20 (m, 1H), 2.85-2.65 (m, 3H), 2.51-2.39 (m, 2H), 2.32-2.10 (m, 3H), 1.99-1.79 (m, 3H), 1.76-1.58 (m, 5H), 1.26 (d, J=6.3 Hz, 3H), 1.08-0.99 (m, 1H), 0.89 (d, J=6.7 Hz, 3H), 0.63-0.48 (m, 1H), 0.35-0.21 (m, 2H), 0.00-0.01 (m, 1H).

Example 29

MS (ESI) m/z: 560.2 [M+H]+ 1H NMR (400 MHz, METHANOL-d4): δ=7.67 (d, J=8.8 Hz, 2H), 7.12 (t, J=8.8 Hz, 1H), 6.95 (d, J=7.7 Hz, 1H), 6.61 (d, J=7.5 Hz, 1H), 6.52 (s, 1H), 3.73-3.63 (m, 2H), 3.27-3.16 (m, 1H), 2.81-2.65 (m, 3H), 2.51-2.39 (m, 2H), 2.32-2.09 (m, 3H), 1.97-1.81 (m, 3H), 1.78-1.55 (m, 5H), 1.26 (d, J=6.2 Hz, 3H), 1.11-0.97 (m, 1H), 0.88 (d, J=6.8 Hz, 3H), 0.62-0.49 (m, 1H), 0.37-0.22 (m, 2H), 0.01-0.10 (m, 1H).

Example 30

MS (ESI) m/z: 560.2 [M+H]+ 1H NMR (400 MHz, METHANOL-d4): δ=7.67 (d, J=9.0 Hz, 2H), 7.18-7.05 (m, 1H), 6.94 (d, J=7.4 Hz, 1H), 6.61 (d, J=7.0 Hz, 1H), 6.52 (s, 1H), 3.75-3.60 (m, 2H), 3.26-3.15 (m, 1H), 2.88-2.63 (m, 3H), 2.52-2.36 (m, 2H), 2.33-2.07 (m, 3H), 2.01-1.80 (m, 3H), 1.79-1.54 (m, 5H), 1.26 (d, J=6.3 Hz, 3H), 1.13-0.99 (m, 1H), 0.88 (d, J=6.7 Hz, 3H), 0.62-0.49 (m, 1H), 0.37-0.22 (m, 1H), 0.01-0.11 (m, 1H).

Example 31

MS (ESI) m/z: 560.2 [M+H]+ 1H NMR (400 MHz, METHANOL-d4) δ=7.67 (d, J=8.6 Hz, 2H), 7.12 (t, J=7.0 Hz, 1H), 6.94 (d, J=7.8 Hz, 1H), 6.61 (d, J=7.4 Hz, 1H), 6.52 (s, 1H), 3.74-3.61 (m, 2H), 3.25-3.18 (m, 1H), 2.87-2.63 (m, 3H), 2.51-2.40 (m, 2H), 2.31-2.10 (m, 3H), 1.99-1.79 (m, 3H), 1.78-1.55 (m, 5H), 1.26 (d, J=6.3 Hz, 3H), 1.11-0.97 (m, 1H), 0.88 (d, J=7.0 Hz, 3H), 0.61-0.50 (m, 1H), 0.35-0.21 (m, 2H), 0.00-0.10 (m, 1H).

SCHEME 7

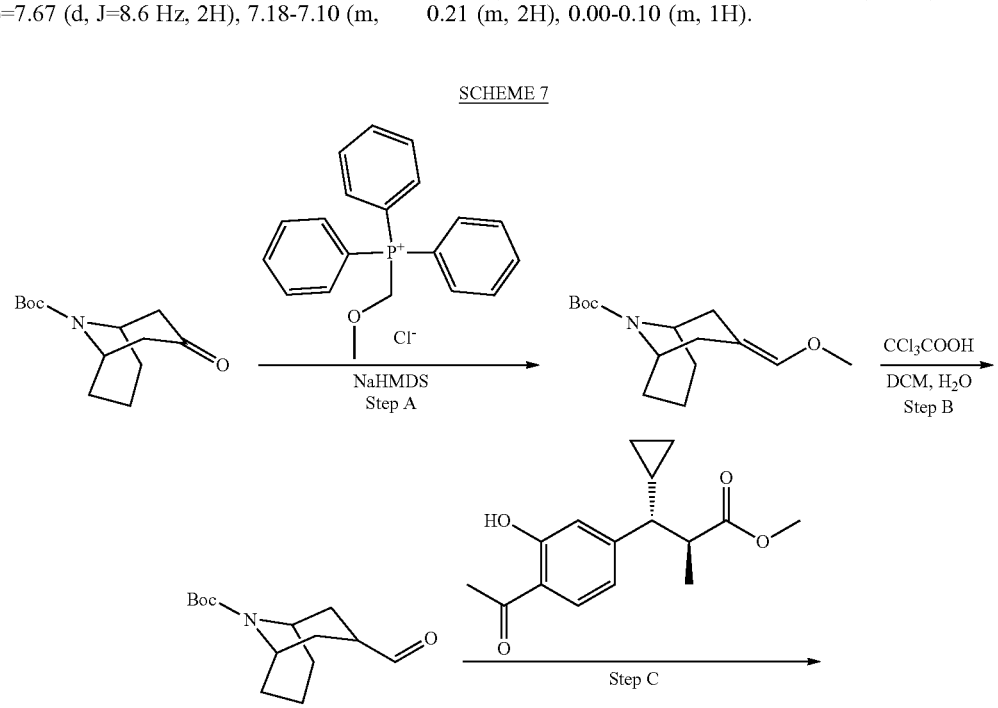

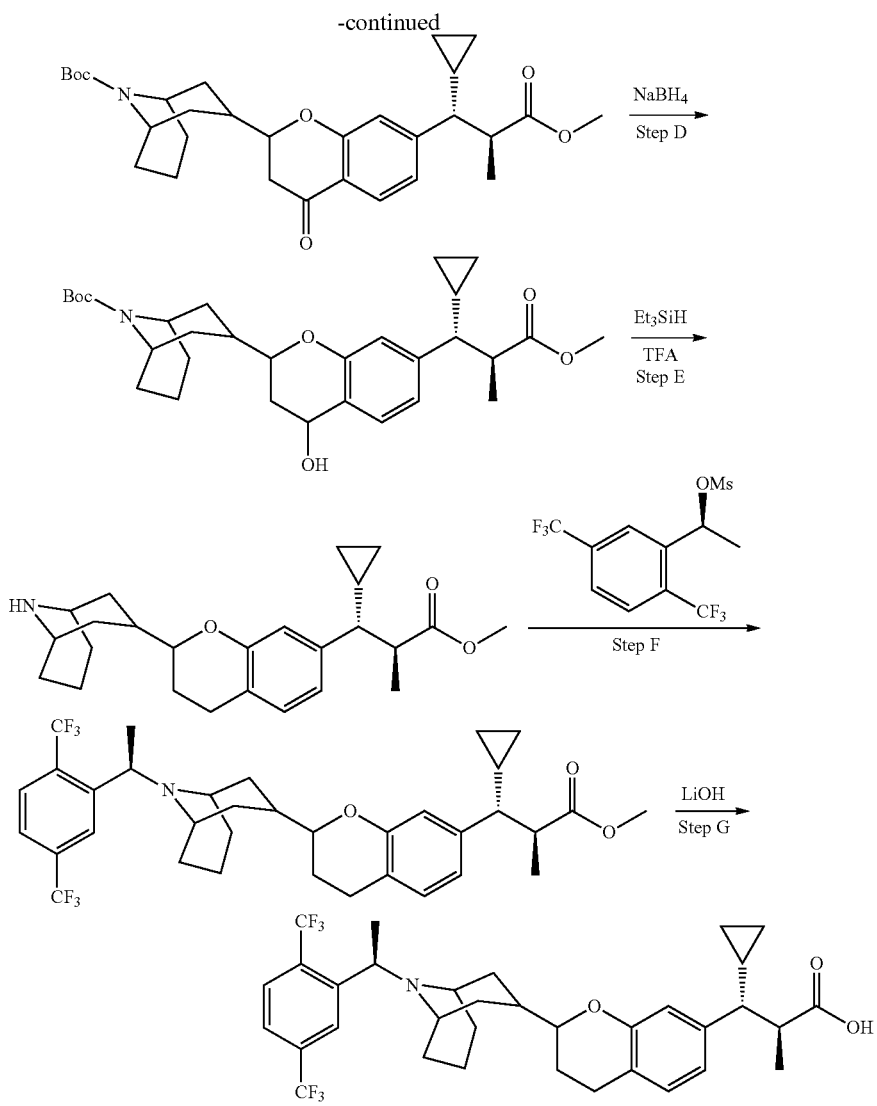

Example 32

(2S,3R)-3-((RS)-2-((1R,3RS,5S)-9-((R)-1-(2,5-bis(trifluoromethyl)phenyl)ethyl)-9-azabicyclo[3.3.1]nonan-3-yl)chroman-7-yl)-3-cyclopropyl-2-methylpropanoic Acid

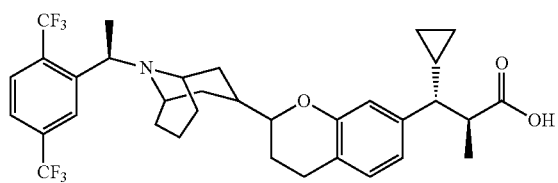 [SMILES: C[C@H](C(=O)O)[C@H](c1ccc2c(c1)OC(C1CC3CCCC(C1)N3[C@H](C)c1cc(C(F)(F)F)ccc1C(F)(F)F)CC2)C1CC1]

Step A: tert-butyl 3-(methoxymethylene)-9-azabicyclo[3.3.1]nonane-9-carboxylate To a solution of (methoxymethyl)triphenylphosphonium chloride (4.30 g, 12.54 mmol) in THF (20 mL) was added sodium bis(trimethylsilyl)amide (12.54 mL, 12.54 mmol) dropwise at 0° C. under nitrogen. The mixture was stirred at 0° C. for 30 min and at 25° C. for 1 h. Then a solution of tert-butyl 3-oxo-9-azabicyclo[3.3.1]nonane-9-carboxylate (1.50 g, 6.27 mmol) in THF (10 mL) was added dropwise at 0° C. The reaction mixture was stirred at 25° C. for another 2 h, then quenched with water (10 mL) at 0° C. and extracted with EtOAc (10 mL×2). The combined organic layers were washed with brine (10 mL), dried over $Na_2SO_4$, filtered and concentrated under reduced pressure. The resulting residue was purified by column chromatography ($SiO_2$, PE:EA=100:1 to 50:1, v/v) to give the title compound. MS (ESI) m/z: 253.1 [M-56+MeCN+H]$^+$

Step B: tert-butyl 3-formyl-9-azabicyclo[3.3.1]nonane-9-carboxylate

To a solution of tert-butyl 3-(methoxymethylene)-9-azabicyclo[3.3.1]nonane-9-carboxylate (1.20 g, 4.49 mmol) in DCM (15 mL) and water (7.5 mL) were added 2,2,2-trichloroacetic acid (4.40 g, 26.9 mmol). The mixture was stirred for 6 h at 25° C. Then the organic layer was separated. The aqueous layer was extracted with DCM (15 mL×3). The combined organic layers were washed with brine (15 mL), dried ($MgSO_4$), and filtered. The filtrate was concentrated under reduced pressure to give the crude product, which was purified by column chromatography (SiO$_2$, PE:EA=15:1 to 10:1) to give the title compound. MS (ESI) m/z: 239.1 [M-56+MeCN+H]$^+$

Step C: (1R,3r,5S)-tert-butyl 3-((RS)-7-((1R,2S)-1-cyclopropyl-3-methoxy-2-methyl-3-oxopropyl)-4-oxochroman-2-yl)-9-azabicyclo[3.3.1]nonane-9-carboxylate (2S,3R)-methyl 3-(4-acetyl-3-hydroxyphenyl)-3-cyclopropyl-2-methylpropanoate (400 mg, 1.448 mmol) and tert-butyl 3-formyl-9-azabicyclo[3.3.1]nonane-9-carboxylate (389 mg, 1.534 mmol) were combined in dry MeOH (10 mL) and pyrrolidine (0.144 mL, 1.737 mmol) was added. The reaction was heated at 60° C. for 12 h. Then the MeOH was removed under reduced pressure. The resulting residue was diluted with H$_2$O (15 mL), and the resulting mixture was extracted with EtOAc (15 mL×3). The combined organic layers were washed with brine (10 mL), dried (MgSO$_4$), and filtered. The filtrate was concentrated under reduced pressure to give the crude product, which was purified by prep-TLC (SiO$_2$, PE:EA=3:1,v/v) to give the title compound. MS (ESI) m/z: 534.3[M+Na]$^+$ $^1$H NMR (400 MHz, CDCl$_3$): δ=7.81 (d, J=8.2 Hz, 1H), 6.85-6.79 (m, 1H), 6.77 (s, 1H), 4.45-4.37 (m, 1H), 4.34-4.26 (m, 1H), 4.07-3.98 (m, 1H), 3.73 (s, 3H), 2.87-2.77 (m, 1H), 2.69-2.65 (m, 1H), 2.08-2.02 (m, 1H), 1.96-1.87 (m, 3H), 1.72-1.61 (m, 8H), 1.48 (s, 9H), 1.09-1.00 (m, 1H), 0.95 (d, J=6.7 Hz, 3H), 0.64-0.55 (m, 1H), 0.41-0.31 (m, 1H), 0.30-0.21 (m, 1H), 0.03-0.05 (m, 1H).

Step D: (1R,3s,5S)-tert-butyl 3-((2RS)-7-((1R,2S)-1-cyclopropyl-3-methoxy-2-methyl-3-oxopropyl)-4-hydroxychroman-2-yl)-9-azabicyclo[3.3.1]nonane-9-carboxylate To a solution of (1R,3r,5S)-tert-butyl 3-((RS)-7-((1R,2S)-1-cyclopropyl-3-methoxy-2-methyl-3-oxopropyl)-4-oxochroman-2-yl)-9-azabicyclo[3.3.1]nonane-9-carboxylate (100 mg, 0.195 mmol) in MeOH (2.0 mL) was added sodium tetrahydroborate (14.79 mg, 0.391 mmol) at 0° C. The reaction mixture was stirred at 0° C. for 1 h under N$_2$ protection, then quenched with saturated aqueous NH$_4$Cl (5 mL). The mixture was extracted with EA (10 mL×3). The combined organic layers were washed with brine (10 mL), dried (MgSO$_4$) and filtered. The filtrate was concentrated in vacuo to give the title compound, which was used for next step without further purification. MS (ESI) m/z: 536.3[M+Na]$^+$

Step E: (2S,3R)-methyl 3-((RS)-2-((1R,3r,5S)-9-azabicyclo[3.3.1]nonan-3-yl) chroman-7-yl)-3-cyclopropyl-2-methylpropanoate To a solution of (1R,3s,5S)-tert-butyl 3-((2RS)-7-((1R,2S)-1-cyclopropyl-3-methoxy-2-methyl-3-oxopropyl)-4-hydroxy-chroman-2-yl)-9-azabicyclo[3.3.1]nonane-9-carboxylate (110 mg, 0.184 mmol) in DCM (3.0 mL) was added triethylsilane (1.0 mL, 6.26 mmol) and TFA (1.0 mL, 12.98 mmol). The reaction mixture was stirred at 25° C. under N$_2$ protection for 1 h, then the solvent was removed under reduced pressure. The resulting residue was neutralized with saturated NaHCO$_3$ aqueous (10 mL) and the mixture was extracted with EA(15 mL×3). The combined organic layers were washed with brine (10 mL), dried (MgSO$_4$) and filtered. The filtrate was concentrated in vacuo to give the title compound, which was used for next step without further purification. MS (ESI) m/z: 398.2[M+H]$^+$

Step F: (2S3R)-methyl 3-((RS)-2-((1R,3R,5S)-9-((R)-1-(2,5-bis(trifluoromethyl)phenyl)ethyl)-9-azabicyclo[3.3.1]nonan-3-yl)chroman-7-yl)-3-cyclopropyl-2-methylpropanoate To a mixture of (2S,3R)-methyl 3-((RS)-2-((1R,3r,5S)-9-azabicyclo[3.3.1]nonan-3-yl)-chroman-7-yl)-3-cyclopropyl-2-methylpropanoate (85.0 mg, 0.171 mmol) and (S)-1-(2,5-bis(trifluoromethyl)phenyl)ethyl methanesulfonate (69.0 mg, 0.205 mmol) in MeCN (3.0 mL) were added DIPEA (0.5 mL, 2.86 mmol) and sodium iodide (77.0 mg, 0.513 mmol). The resulting mixture was stirred at 100° C. for 8 h and then allowed to reach room temperature. Then the mixture was poured into water (5 mL), and extracted with EtOAc (10 mL×3). The combined organic layers were washed with brine (saturated, 10 mL), dried (Na$_2$SO$_4$), and filtered. The filtrate was evaporated under reduced pressure to give crude product, which was purified by prep-HPLC (TFA) to give the title compound. MS (ESI) m/z: 638.3 [M+H]$^+$ Prep HPLC conditions:Preparative HPLC on a MS trigger instrument fitted with a YMC-Actus Pro C18 150× 30×5 um; mobile phase A: 0.1% TFA in water; mobile phase B: acetonitrile; gradient: 37-67% B, 0-11.0 min; 100% B, 11.1-13.0 min; 10% B, 13.1-16 min; FlowRate: 40 mL/min.

Step G: (2S,3R)-3-((RS)-2-((1R,3RS,5S)-9-((R)-1-(2,5-bis(trifluoromethyl)phenyl)ethyl)-9-azabicyclo[3.3.1]nonan-3-yl)chroman-7-yl)-3-cyclopropyl-2-methylpropanoic Acid To a solution of (2S,3R)-methyl 3-((RS)-2-((1R,3R,5S)-9-((R)-1-(2,5-bis(trifluoromethyl)phenyl)ethyl)-9-azabicyclo[3.3.1]nonan-3-yl)chroman-7-yl)-3-cyclopropyl-2-methyl propanoate (10 mg, 0.016 mmol) in MeOH (0.8 mL), THF (0.8 mL) and water (0.8 mL) was added LiOH (7.51 mg, 0.314 mmol). The reaction mixture was stirred at 50° C. for 15 h. Then the reaction mixture was cooled to 25° C., and acidified with citric acid to adjust the pH to pH=5-6. The mixture was extracted with EtOAc (10 mL×3), dried (Na$_2$SO$_4$) and filtered. The filtrate was concentrated in vacuo to give crude product, which was purified by prep-HPLC (Neutral) to give the title compound. To a solution of the title compound (6 mg) in MeCN (1.0 mL) and water (1.0 mL) was added an aqueous solution of NaOH (1.0 eq, 0.5 M), and the mixture was stirred for 1 h at room temperature. Then the reaction mixture was lyophilized to give the sodium salt of the title compound. Prep-HPLC conditions: Preparative HPLC on a MS trigger instrument fitted with a Phenomenex Gemini C18 250×21.2 mm×5 um; mobile phase A: water(10 mM NH$_4$HCO$_3$); mobile phase B: acetonitrile; gradient: 52-82% B, 0-12.0 min; 100% B, 12.1-14.0 min; 10% B, 14.1-17.0 min; flowRate: 25 mL/min. MS (ESI) m/z: 624.3 [M+H]$^+$ $^1$H NMR (400 MHz, CD$_3$OD): δ=8.44 (s, 1H), 7.90-7.81 (m, 1H), 7.75-7.67 (m, 1H), 6.95 (d, J=7.4 Hz, 1H), 6.68-6.55 (m, 1H), 4.71-4.65 (m, 1H), 4.59 (br. s., 4H), 3.70-3.58 (m, 1H), 3.20-3.09 (m, 1H), 2.92-2.84 (m, 1H), 2.74 (br. s., 1H), 2.57-2.43 (m, 1H), 2.20-2.08 (m, 1H), 2.01 (br. s., 1H), 1.91-1.84 (m, 1H), 1.68 (d, J=7.0 Hz, 1H), 1.59-1.47 (m, 1H), 1.29 (br. s., 3H), 1.16-1.02 (m, 1H), 0.92 (d, J=6.7 Hz, 3H), 0.63-0.51 (m, 1H), 0.39-0.25 (m, 1H), 0.04-0.07 (m, 1H).

TABLE 6

The compounds of Examples 33-35 were prepared in a similar manner to the procedure of Example 32 using the appropriate intermediates and commercially available starting materials.

| Example | Structure | M.W. | Compound Name | LC/MS (ESI) observed [M + 1]+ |
|---|---|---|---|---|
| 33 | 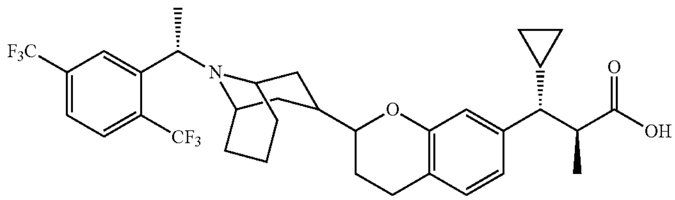 [SMILES: C[C@H](C(=O)O)[C@H](c1ccc2c(c1)OC(C1CC3CCCC(C1)N3[C@@H](C)c1cc(C(F)(F)F)ccc1C(F)(F)F)CC2)C1CC1] | 623.67 | (2S,3R)-3-((RS)-2-((1R,3RS,5S)-9-((S)-1-(2,5-bis(trifluoromethyl)-phenyl)ethyl)-9-aza-bicyclo[3.3.1]-nonan-3-yl)chroman-7-yl)-3-cyclopropyl-2-methyl-propanoic acid | 624.3 |
| 34 | 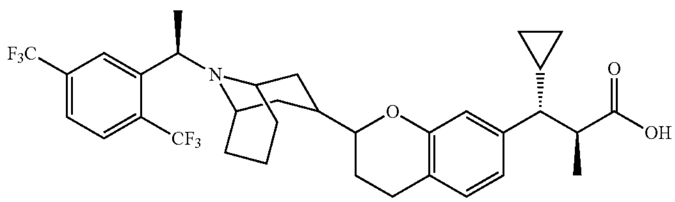 [SMILES: C[C@H](C(=O)O)[C@H](c1ccc2c(c1)OC(C1CC3CCCC(C1)N3[C@H](C)c1cc(C(F)(F)F)ccc1C(F)(F)F)CC2)C1CC1] | 573.66 | (2S,3R)-3-cyclopropyl-3-((RS)-2-((1R,3RS,5S)-9-((R)-1-(5-fluoro-2-(tri-fluoromethyl)phenyl)eth-yl)-9-azabicyclo[3.3.1]-nonan-3-yl)chroman-7-yl)-2-methylpropanoic acid | 574.3 |
| 35 | 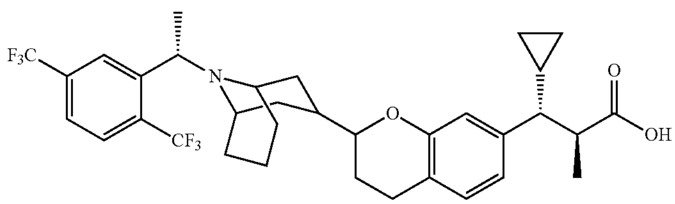 [SMILES: C[C@H](C(=O)O)[C@H](c1ccc2c(c1)OC(C1CC3CCCC(C1)N3[C@@H](C)c1cc(C(F)(F)F)ccc1C(F)(F)F)CC2)C1CC1] | 573.66 | (2S,3R)-3-cyclopropyl-3-((RS)-2-((1R,3RS,5S)-9-((S)-1-(5-fluoro-2-(tri-fluoromethyl)phenyl)eth-yl)-9-azabicyclo[3.3.1]-nonan-3-yl)chroman-7-yl)-2-methylpropanoic acid | 574.3 |

Example 33

$^1$H NMR (400 MHz, CD$_3$OD): δ=8.44 (s, 1H), 7.89-7.80 (m, J=12.9 Hz, 1H), 7.70 (d, J=8.2 Hz, 1H), 6.95 (d, J=7.8 Hz, 1H), 6.67-6.53 (m, 2H), 4.73-4.61 (m, 1H), 3.71-3.59 (m, 1H), 3.19-3.10 (m, 1H), 2.91-2.66 (m, 4H), 2.58-2.43 (m, 1H), 2.19-1.95 (m, 4H), 1.92-1.61 (m, 7H), 1.60-1.46 (m, 2H), 1.29 (t, J=6.1 Hz, 3H), 1.13-1.02 (m, 1H), 0.92 (d, J=6.7 Hz, 3H), 0.63-0.53 (m, 1H), 0.39-0.26 (m, 2H), 0.06-0.07 (m, 1H).

Example 34

$^1$H NMR (400 MHz, CD$_3$OD): δ=7.86-7.77 (m, J=10.2 Hz, 1H), 7.74-7.63 (m, 1H), 7.16-7.06 (m, 1H), 6.95 (d, J=7.8 Hz, 1H), 6.61 (d, J=4.7 Hz, 2H), 4.65-4.57 (m, 1H), 3.69-3.59 (m, 1H), 3.21-3.11 (m, 1H), 2.99-2.90 (m, 1H), 2.88-2.66 (m, 3H), 2.56-2.44 (m, 1H), 2.21-2.08 (m, 1H), 2.08-1.96 (m, 3H), 1.94-1.72 (m, 5H), 1.71-1.48 (m, 4H), 1.30-1.25 (m, 3H), 1.13-1.02 (m, 1H), 0.92 (d, J=6.7 Hz, 3H), 0.62-0.53 (m, 1H), 0.37-0.27 (m, 2H), 0.04-0.06 (m, 1H).

Example 35

$^1$H NMR (400 MHz, CD$_3$OD): δ=7.86-7.76 (m, J=9.0 Hz, 1H), 7.74-7.65 (m, 1H), 7.16-7.07 (m, 1H), 6.95 (d, J=7.4 Hz, 1H), 6.67-6.56 (m, 2H), 4.68-4.53 (m, 1H), 3.70-3.57 (m, 1H), 3.21-3.10 (m, 1H), 2.99-2.89 (m, 1H), 2.87-2.66 (m, 3H), 2.57-2.42 (m, 1H), 2.20-1.95 (m, 4H), 1.94-1.71 (m, 5H), 1.71-1.49 (m, 4H), 1.31-1.24 (m, 3H), 1.14-1.02 (m, 1H), 0.92 (d, J=6.7 Hz, 3H), 0.62-0.53 (m, 1H), 0.37-0.26 (m, 2H), 0.05-0.08 (m, 1H).

SCHEME 8

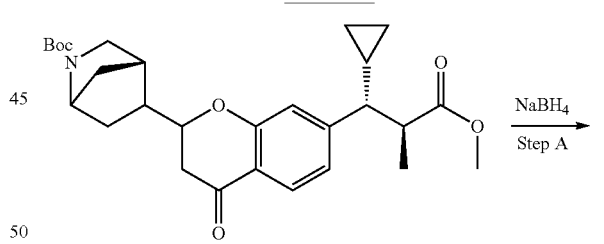

NaBH$_4$ Step A

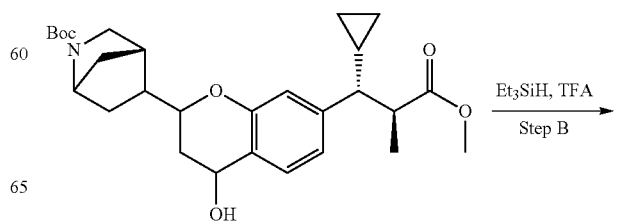

Et$_3$SiH, TFA Step B

-continued

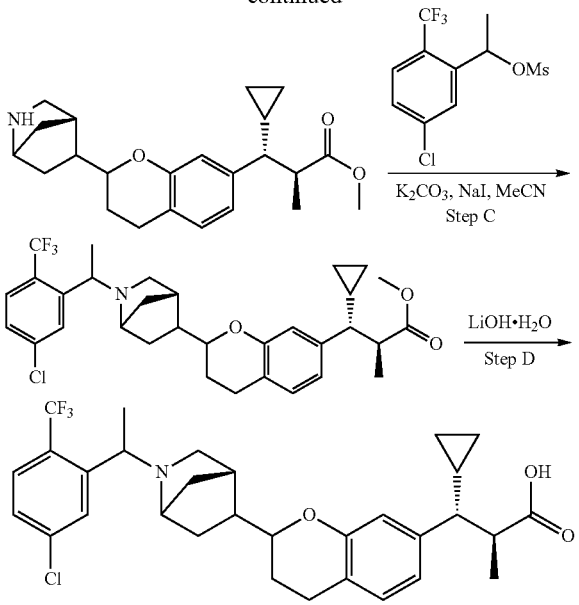

Example 36

(2S,3R)-3-((S or R)-2-((R or S, R or S)-2-(1-(5-chloro-2-(trifluoromethyl)-phenyl)-ethyl)-2-azabicyclo[2.2.1]heptan-5-yl)chroman-7-yl)-3-cyclopropyl-2-methylpropanoic Acid

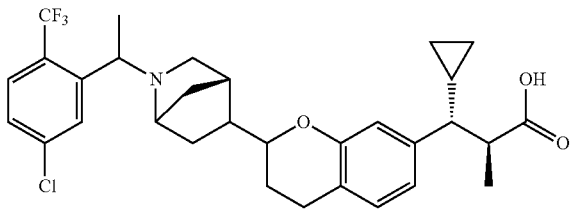 [SMILES: CC(c1cc(Cl)ccc1C(F)(F)F)N1C[C@H]2CC1CC2C1CCc2ccc([C@H](C3CC3)[C@H](C)C(=O)O)cc2O1]

Step A: (R or S, R or S)-tert-butyl 5-(7-((1R,2S)-(S or R)-1-cyclopropyl-3-methoxy-2-methyl-3-oxopropyl)-4-hydroxychroman-2-yl)-2-azabicyclo[2.2.1]heptane-2-carboxylate To a solution of (R or S, R or S)-tert-butyl 5-(7-((1R, 2S)-(S or R)-1-cyclopropyl-3-methoxy-2-methyl-3-oxopropyl)-4-oxochroman-2-yl)-2-azabicyclo[2.2.1]heptane-2-carboxylate (550 mg, 0.943 mmol; prepared according the procedures described above from (1S,4R)-tert-butyl 5-oxo-2-azabicyclo[2.2.1]heptane-2-carboxylate) in EtOH (12 mL) was added NaBH$_4$ (71.6 mg, 1.887 mmol) in portions at 0° C. The reaction mixture was stirred at 0° C. for 2 h, then quenched with water (12 mL) at 22° C. The aqueous phase was separated and extracted with EtOAc (10 mL×3). The combined organic layers were washed with brine (15 mL), dried over anhydrous MgSO$_4$ and filtered. The filtrate was concentrated under reduced pressure. The resulting residue was purified by prep-TLC (SiO$_2$, PE:EtOAc=2:1, v/v) to give the title compound, which was used directly for the next step. LC-MS (ESI): m/z 508.3 [M+Na]$^+$ Step B: (2S,3R)-methyl 3-(R or S)-(2-((R or S, R or S)-2-azabicyclo[2.2.1]heptan-5-yl) chroman-7-yl)-3-cyclopropyl-2-methylpropanoate To a solution of (R or S, R or S)-tert-butyl 5-(7-((1R, 2S)-(S or R)-1-cyclopropyl-3-methoxy-2-methyl-3-oxopropyl)-4-hydroxychroman-2-yl)-2-azabicyclo[2.2.1]heptane-2-carboxylate (500 mg, 0.855 mmol) in DCM (5.0 mL) and TFA (2.5 mL, 33.5 mmol) was added dropwise triethylsilane (2.5 mL, 15.7 mmol). The mixture was stirred for 2 h under N$_2$ atmosphere at 23° C., then concentrated in vacuo. Water (5.0 mL) was added to the mixture, followed by the addition of NaHCO$_3$ solid to adjust the pH of the mixture to pH=8. The aqueous phase was extracted with EtOAc (5 mL×3). The combined organic layers were washed with water (10 mL) and brine (10 mL), dried over anhydrous MgSO$_4$ and filtered. The filtrate was concentrated under reduced pressure to give the title compound, which was used directly for the next step. LC-MS (ESI):m/z 370.2 [M+H]$^+$ $^1$H NMR (400 MHz, DMSO-d$_6$): δ=6.97 (d, J=7.8 Hz, 1H), 6.65 (d, J=7.8 Hz, 1H), 6.57 (s, 1H), 3.87 (t, J=1.0 Hz, 1H), 3.63 (s, 3H), 2.96 (s, 1H), 2.82-2.60 (m, 3H), 2.37-2.29 (m, 1H), 2.11-2.02 (m, 1H), 1.96-1.85 (m, 3H), 1.77 (t, J=9.9 Hz, 2H), 1.53 (d, J=11.0 Hz, 1H), 1.06-0.97 (m, 1H), 0.81 (d, J=6.8 Hz, 3H), 0.52-0.48 (m, 1H), 0.26-0.17 (m, 1H), 0.14-0.05 (m, 1H), 0.06-0.15 (m, 1H).

Step C: (2S,3R)-methyl 3-((S or R)-(2-((R or S, R or S)-2-(1-(5-chloro-2-(trifluoromethyl)phenyl) ethyl)-2-azabicyclo[2.2.1]heptan-5-yl)chroman-7-yl)-3-cyclopropyl-2-methylpropanoate To a solution of (2S,3R)-methyl 3-(R or S)-(2-((R or S, R or S)-2-azabicyclo[2.2.1]heptan-5-yl)chroman-7-yl)-3-cyclopropyl-2-methylpropanoate (50.0 mg, 0.135 mmol) and 1-(5-chloro-2-(trifluoromethyl)phenyl)ethyl methanesulfonate (61.3 mg, 0.203 mmol) in MeCN (1.0 mL) were added K$_2$CO$_3$ (93.2 mg, 0.675 mmol) and NaI (81.2 mg, 0.540 mmol). The mixture was stirred for 15 hours under N$_2$ atmosphere at 80° C., then water (2.0 mL) was added, and the mixture was extracted with EtOAc (2 mL×3). The combined organic layers were washed with water (3.0 mL) and brine (3.0 mL), dried over anhydrous MgSO$_4$ and filtered. The filtrate was concentrated under reduced pressure to give the title compound. LCMS (ESI):m/z 576.3 [M+H]$^+$ Step D: (2S,3R)-3-((S or R)-2-((R or S, R or S)-2-(1-(5-chloro-2-(trifluoromethyl)phenyl)ethyl)-2-azabicyclo[2.2.1]heptan-5-yl)chroman-7-yl)-3-cyclopropyl-2-methylpropanoic Acid To a suspension of (2S,3R)-methyl 3-((S or R)-(2-((R or S, R or S)-2-(1-(5-chloro-2-(trifluoromethyl)phenyl)ethyl)-2-azabicyclo[2.2.1]heptan-5-yl)chroman-7-yl)-3-cyclopropyl-2-methylpropanoate (70.0 mg, 0.122 mmol) in MeOH (1.0 mL), THF (1.0 mL) and water (1.0 mL) was added lithium hydroxide monohydrate (102 mg, 2.430 mmol). The resulting suspension was heated to 55° C. for 15 h, then concentrated in vacuo to remove the solvent. Water (1.0 mL) was added to the resulting residue, and citric acid was added to adjust the pH of the mixture to pH 5. The resulting mixture was extracted with EtOAc (2 mL×3). The combined organic layers were washed with water (3.0 mL) and brine (3.0 mL), dried over anhydrous MgSO$_4$ and filtered. The filtrate was concentrated under reduced pressure. The resulting residue was purified by HPLC (neutral) to give the title compound. To a solution of the title compound in MeCN (0.5 mL) and water (0.5 mL) was added an aqueous solution of NaOH (1.0 eq, 0.5 M), and the mixture was stirred for 1 hour at room temperature. Then the reaction mixture was lyophilized to give the sodium salt of the title compound. Prep HPLC conditions: Preparative HPLC on a MS trigger instrument fitted with a waters Prep OBD C18 150*20 mm*5 um; mobile phase A: water; mobile phase B: acetonitrile; gradient:45-65% B, 0-10 min; 100% B, 10-12 min; flowRate: 25 mL/min. LCMS (ESI):m/z 562.2 [M+H]$^+$ $^1$H NMR (400 MHz, METHANOL-d$_4$): δ=7.99-7.92 (m, 1H), 7.71 (d, J=8.2 Hz, 1H), 7.53-7.47 (m, 1H), 6.94 (d, J=7.5 Hz, 1H), 6.63 (d, J=7.7 Hz, 1H), 6.55 (s, 1H), 4.22-4.09 (m, 1H), 3.84 (t, J=1.0 Hz, 1H), 2.95-2.46 (m, 6H), 2.19-1.95 (m, 3H), 1.94-1.78 (m, 3H), 1.77-1.63 (m, 3H), 1.48 (d, J=6.0 Hz, 1H), 1.37 (d, J=6.0 Hz, 2H), 1.11-1.00 (m, 1H), 0.87 (d, J=6.6 Hz, 3H), 0.61-0.52 (m, 1H), 0.38-0.22 (m, 2H), 0.02-0.10 (m, 1H).

1.09-0.99 (m, 1H), 0.86 (d, J=4.6 Hz, 3H), 0.60-0.50 (m, 1H), 0.40-0.20 (m, 2H), 0.03-0.12 (m, 1H).

Example 38

$^1$H NMR (400 MHz, CDCl$_3$): δ=8.30-8.11 (m, 1H), 7.72 (dd, J=5.1, J$_1$=8.6 Hz, 1H), 7.24-7.13 (m, 1H), 6.96 (d, J=7.4 Hz, 1H), 6.66-6.56 (m, 1H), 6.46 (s, 1H), 4.43 (d, J=7.0 Hz, 1H), 4.37-4.22 (m, 1H), 4.14 (t, J=9.4 Hz, 1H), 3.61 (d, J=7.0 Hz, 1H), 3.02 (br. s., 1H), 2.94-2.85 (m, 1H), 2.76-2.71 (m, 1H), 2.51 (d, J=10.6 Hz, 5H), 2.26 (br. s., 2H), 2.07 (d, J=11.0 Hz, 2H), 1.89 (d, J=6.7 Hz, 3H), 1.75-1.70 (m, 1H), 1.12-0.93 (m, 4H), 0.59 (d, J=5.9 Hz, 1H), 0.32 (d, J=4.7 Hz, 2H), 0.10-0.06 (m, 1H).

Example 39

$^1$H NMR (400 MHz, METHANOL-d$_4$): δ=7.81-7.75 (m, 1H), 7.71 (d, J=8.2 Hz, 1H), 7.24 (t, J=7.2 Hz, 1H), 6.94 (d,

TABLE 7

The compounds of Examples 37-39 was prepared in a similar manner to the procedure of Example 36 using the appropriate intermediates and commercially available starting materials.

| Example | Structure | M.W. | Compound Name | LC/MS (ESI) observed [M + H]$^+$ |
|---------|-----------|------|---------------|----------------------------------|
| 37 | 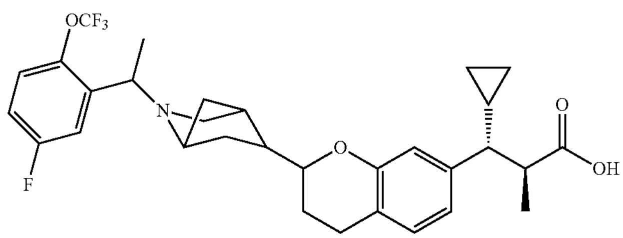 [SMILES: CC(c1cc(F)ccc1OC(F)(F)F)N1CC2CC1CC2C1CCc2ccc([C@H](C3CC3)[C@H](C)C(=O)O)cc2O1] | 561.6 | (2S,3R)-3-cyclopropyl-3-((R or S)-2-((R or S,R or S)-2-((RS)-1-(5-fluoro-2-(trifluoromethoxy)-phenyl)ethyl)-2-azabicyclo[2.2.1]heptan-5-yl)-chroman-7-yl)-2-methyl-propanoic acid | 562.4 |
| 38 | 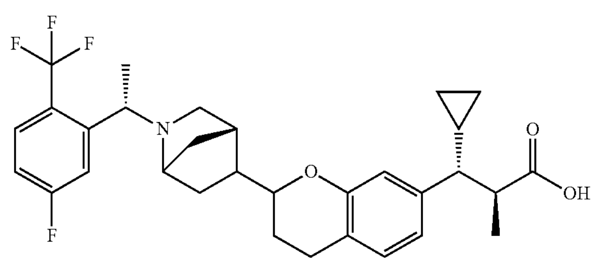 [SMILES: C[C@H](C(=O)O)[C@H](c1ccc2c(c1)OC(C1CC3C[C@@H]1CN3[C@@H](C)c1cc(F)ccc1C(F)(F)F)CC2)C1CC1] | 545.61 | (2S,3R)-3-cyclopropyl-3-(2-((4S)-2-((S)-1-(5-fluoro-2-(trifluoromethyl)phenyl)ethyl)-2-azabicyclo[2.2.1]heptan-5-yl)chroman-7-yl)-2-methyl-propanoic acid | 546.2 |
| 39 | 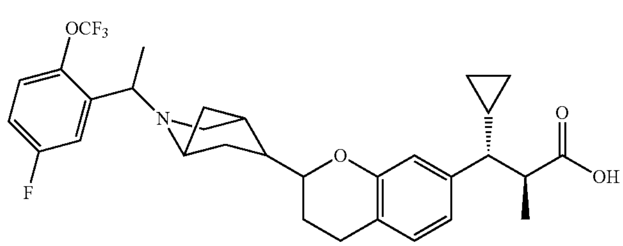 [SMILES: CC(c1cc(F)ccc1OC(F)(F)F)N1CC2CC1CC2C1CCc2ccc([C@H](C3CC3)[C@H](C)C(=O)O)cc2O1] | 545.6 | (2S,3R)-3-cyclopropyl-3-((R or S)-2-((R or S,R or S)-2-((RS)-1-(5-fluoro-2-(trifluoromethyl)-phenyl)ethyl)-2-azabicyclo-[2.2.1]heptan-5-yl)chroman-7-yl)-2-methylpropanoic acid | 546.2 |

Example 37

$^1$H NMR (400 MHz, METHANOL-d$_4$): δ=7.52-7.34 (m, 2H), 7.24-7.15 (m, 1H), 6.93 (d, J=7.5 Hz, 1H), 6.62 (d, J=1.0 Hz, 1H), 6.54 (s, 1H), 4.33-4.17 (m, 1H), 3.90-3.79 (m, 1H), 3.01 (d, J=7.3 Hz, 1H), 2.88-2.49 (m, 5H), 2.18-1.63 (m, 9H), 1.49 (d, J=6.2 Hz, 1H), 1.39 (d, J=6.2 Hz, 2H),

J=7.8 Hz, 1H), 6.63 (d, J=7.4 Hz, 1H), 6.54 (s, 1H), 4.22 (d, J=5.5 Hz, 1H), 3.83 (t, J=1.0 Hz, 1H), 3.74 (br. s., 1H), 2.87-2.72 (m, 3H), 2.71-2.60 (m, 2H), 2.50 (br. s., 1H), 2.12-2.02 (m, 1H), 1.94-1.82 (m, 3H), 1.78-1.64 (m, 3H), 1.50 (d, J=6.3 Hz, 3H), 1.10-1.00 (m, 1H), 0.87 (d, J=6.7 Hz, 3H), 0.60-0.50 (m, 1H), 0.38-0.21 (m, 2H), 0.03-0.12 (m, 1H).

TABLE 8

The compounds of Examples 40-45 were prepared according to the procedures above using the appropriate intermediates and commercially available starting materials.

| Example | Structure | M.W. | Compound Name | LC/MS (ESI) observed [M + H]+ |
|---|---|---|---|---|
| 40 | 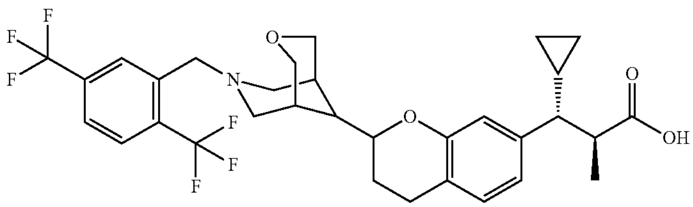 [SMILES: C[C@H](C(=O)O)[C@H](c1ccc2c(c1)OC(C1C3COCC1CN(Cc1cc(C(F)(F)F)ccc1C(F)(F)F)C3)CC2)C1CC1] | 611.6 | (2S,3R)-3-(2-((1R,5S)-7-(2,5-bis(trifluoromethyl)benzyl)-3-oxa-7-azabicyclo[3.3.1]nonan-9-yl)chroman-7-yl)-3-cyclopropyl-2-methylpropanoic acid | 612.4 |
| 41 | 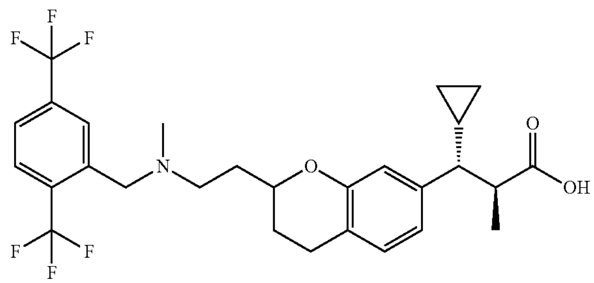 [SMILES: C[C@H](C(=O)O)[C@H](c1ccc2c(c1)OC(CCN(C)Cc1cc(C(F)(F)F)ccc1C(F)(F)F)CC2)C1CC1] | 543.6 | (2S,3R)-3-(2-(2-((2,5-bis-(trifluoromethyl)benzyl)(methyl)amino)ethyl)chroman-7-yl)-3-cyclopropyl-2-methylpropanic acid | 544.5 |
| 42 | 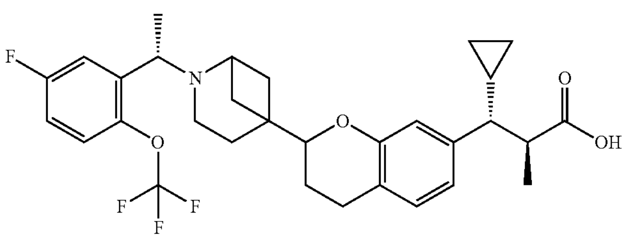 [SMILES: C[C@H](C(=O)O)[C@H](c1ccc2c(c1)OC(C13CCN([C@@H](C)c4cc(F)ccc4OC(F)(F)F)C(C1)C3)CC2)C1CC1] | 561.6 | ((2S,3R)-3-cyclopropyl-3-(2-(2-((R)-1-(5-fluoro-2-(trifluoromethoxy)phenyl)ethyl)-2-azabicyclo[3.1.1]heptan-5-yl)chroman-7-yl)-2-methylpropanoic acid | 562.3 |
| 43 | 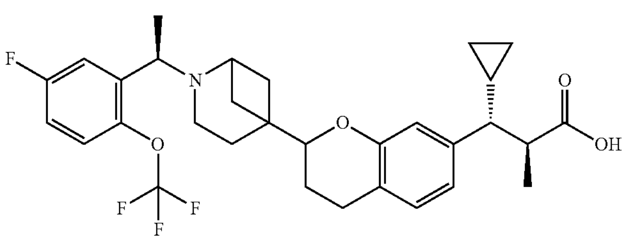 [SMILES: C[C@H](C(=O)O)[C@H](c1ccc2c(c1)OC(C13CCN([C@H](C)c4cc(F)ccc4OC(F)(F)F)C(C1)C3)CC2)C1CC1] | 561.6 | ((2S,3R)-3-cyclopropyl-3-(2-(2-((R)-1-(5-fluoro-2-(trifluoromethoxy)phenyl)ethyl)-2-azabicyclo[3.1.1]heptan-5-yl)chroman-7-yl)-2-methylpropanoic acid | 562.3 |
| 44 | 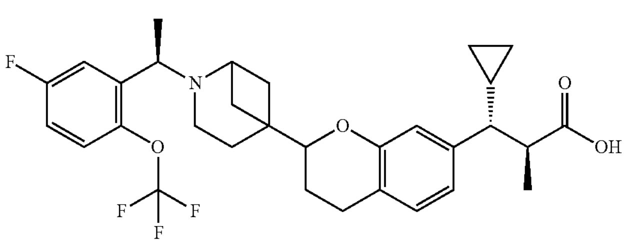 [SMILES: C[C@H](C(=O)O)[C@H](c1ccc2c(c1)OC(C13CCN([C@H](C)c4cc(F)ccc4OC(F)(F)F)C(C1)C3)CC2)C1CC1] | 561.6 | (2S,3R)-3-cyclopropyl-3-(2-(2-((R)-1-(5-fluoro-2-(trifluoromethoxy)phenyl)ethyl)-2-azabicyclo[3.1.1]heptan-5-yl)chroman-7-yl)-2-methylpropanoic acid | 562.4 |

EXAMPLE OF A PHARMACEUTICAL COMPOSITION

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

BIOLOGICAL ASSAYS

Generation of GPR40-Expressing Cells:

Human GPR40 stable cell-lines were generated in HEK cells. The expression plasmids were transfected using lipofectamine (Life Technologies) following manufacturer's instructions. Stable cell-lines were generated following drug selection and single cell cloning.

Inositol Phosphate Turnover (IP1) Assay 2:

The assay is performed in 384-well format. HEK cells stably expressing human GPR40 are plated at 15,000 cells per well in growth medium (DMEM/10% fetal calf serum). Cell plates are then incubated 16 hours at 37 degrees in a 5% $CO_2$ incubator.

Measurement of Inositol Phosphate Turnover (IP1) is performed using the CisBio IP-One kit (Part number 62IPA-PEB). After the 16 hour incubation, the cells are washed with HEPES buffer and 10 ul of stimulation buffer (prepared as described in the kit) is added to each well. In a separate plate, compounds are diluted in DMSO (400-fold over the final concentration in the assay well) and 25 nl is acoustically transferred to the appropriate well in the assay cell plate. The plates are then incubated for 60 minutes at 37 degrees. 10 ul of detection buffer (also prepared as described in the IP-One kit) is added to each well and the plates are incubated for 60 minutes in the dark. The plates are then read in a Perkin Elmer EnVision or equivalent reader able to measure FRET. Fluorescent ratio of emission at 665 and 620 nm is then converted to IP1 concentration by back calculating from an IP1 standard curve prepared at the time of the assay.

The compounds of the present invention, including the compounds in Examples 1, 2 and 40, have $EC_{50}$ values less than 6500 nanomolar (nM) in the Inositol Phophate Turnover (IP1) Assay 2 described above. Inositol Phophate Turnover (IP1) Assay 2 $EC_{50}$ values for specific compounds are listed in Table I.

TABLE I

Inositol Phophate Turnover (IP1) Assay 2 $EC_{50}$ values

| Example No. | Human IP1 (nM) | Isomer* |
|---|---|---|
| 1 | 141.4 | Isomer A |
| 2 | 156.3 | Isomer B |
| 40 | 38.51 | Mixture of 4 isomers |

Inositol Phosphate Turnover (IP1) Assay:

The assay was performed in 384-well format. HEK cells stably expressing human GPR40 were plated at 7500 cells per well in growth medium (DMEM/10% fetal calf serum). Cell plates were then incubated 16 hours at 37 degrees in a 5% $CO_2$ incubator. Measurement of Inositol Phosphate Turnover (IP1) was performed using the CisBio IP-One kit (Part number 62IPAPEB). After the 16 hour incubation, the growth media was removed by centrifugation using the BlueWasher (AusWasher GUI Ver. v1.0.1.8) Protocol #21-"Light Dry" and 10 ul of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% $CO_2$ incubator. 10 ul of detection buffer (also prepared as described in the IP-One kit) was added to each well and the plates were incubated at room temperature for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay. Data was normalized to % activity using a reference compound and $EC_{50}$s determined using a standard 4-parameter fit.

The compounds of the present invention, including the compounds in Examples 3-39 and 41 to 44, have $EC_{50}$ values less than 6000 nanomolar (nM) in the Inositol Phophate Turnover Assay 1 described above. Inositol Phophate Turnover (IP1) Assay $EC_{50}$ values for specific compounds are shown in Table II.

TABLE II

Inositol Phosphate Turnover (IP1) Assay $EC_{50}$ values

| Example No. | Human IP1 EC50 (nM) | Isomers |
|---|---|---|
| 1 | Not determined | Isomer A |
| 2 | Not determined | Isomer B |
| 3 | 20.29 | Mixture of two isomers |
| 4 | 36.64 | Mixture of two isomers |
| 5 | 33.78 | Mixture of two isomers |
| 6 | 21.54 | Mixture of two isomers |
| 7 | 11.16 | Mixture of two isomers |
| 8 | 11.21 | Mixture of two isomers |
| 9 | 63.67 | Mixture of two isomers |
| 10 | 29.28 | Isomer A |
| 11 | 14.15 | Isomer B |
| 12 | 22.26 | Mixture of two isomers |
| 13 | 11.88 | Mixture of four isomers |
| 14 | 11.08 | Mixture of four isomers |
| 15 | 17.49 | Mixture of four isomers |
| 16 | 1.283 | Mixtre of four isomers |
| 17 | 0.6875 | Mixture of four isomers |
| 18 | 4.203 | Mixture of two isomers |
| 19 | 2.619 | Mixture of two isomers |
| 20 | 13.42 | Mixture of two isomers |
| 21 | 3.139 | Mixture of two isomers |
| 22 | 45.6 | Mixture of two isomers |
| 23 | 49.82 | Mixture of two isomers |
| 24 | 9.656 | Mixture of two isomers |
| 25 | 67.28 | Mixture of two isomers |
| 26 | 9.679 | Mixture of three isomers |
| 27 | 20.21 | Mixture of two isomers |
| 28 | 28.74 | Isomer A |
| 29 | 72.80 | Mixture of two isomers |
| 30 | 452.8 | Isomer B |
| 31 | 32.62 | Isomer C |
| 32 | 170.9 | Mixture of four isomers |
| 33 | 750.2 | Mixture of four isomers |
| 34 | 29.44 | Mixture of four isomsers |
| 35 | 90.93 | Mixture of four isomers |
| 36 | 12.29 | Mixture of four isomers |
| 37 | 71.35 | Mixture of four isomers |
| 38 | 10.59 | Mixture of four isomers |
| 39 | 44.09 | Mixture of four isomers |
| 40 | Not determined | Mixture of four isomers |
| 41 | 8.724 | Mixture of two isomers |
| 42 | 2.091 | Mixture of two isomers |
| 43 | 60.61 | Isomer A |
| 44 | 2.141 | Isomer B |

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

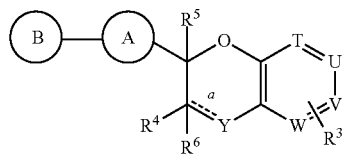

or a pharmaceutically acceptable salt thereof; wherein
"a" is a single bond;
T is CH;
U is $CR^1$;
V is $CR^2$;
W is CH;
Y is selected from the group consisting of: —$CR^gR^g$;
A is selected from the group consisting of:
(1) —$C_{1-6}$alkyl-N($R''$)—,
(2) —$C_{1-6}$alkyl-$C_{6-14}$cycloheteroalkyl, and
(3) —$C_{6-14}$cycloheteroalkyl,
wherein A is unsubstituted or substituted with one to five substituents selected from $R^a$;
B is selected from the group consisting of:
(1) hydrogen,
(2) aryl,
(3) aryl-O—,
(4) aryl-$C_{1-10}$ alkyl-,
(5) aryl-$C_{1-10}$ alkyl-O—,
(6) $C_{3-6}$cycloalkyl,
(7) $C_{3-6}$cycloalkyl-$C_{1-10}$alkyl-,
(8) $C_{3-6}$cycloalkyl-$C_{1-10}$alkyl-O—,
(9) $C_{3-6}$cycloalkenyl,
(10) $C_{3-6}$cycloalkenyl-$C_{1-10}$alkyl-,
(11) $C_{3-6}$cycloalkenyl-$C_{1-10}$alkyl-O—,
(12) $C_{2-5}$cycloheteroalkyl,
(13) $C_{3-6}$cycloheteroalkyl-$C_{1-10}$alkyl-,
(14) $C_{3-6}$cycloheteroalkyl-$C_{1-10}$alkyl-O—,
(15) heteroaryl,
(16) heteroaryl-O—,
(17) heteroaryl-$C_{1-10}$ alkyl-, and
(18) heteroaryl-$C_{1-10}$ alkyl-O—,
wherein B is unsubstituted or substituted with one to five substituents selected from $R^b$;
$R^1$ is selected from —$C_{1-6}$alkyl, wherein each alkyl is unsubstituted or substituted with one to three substituents selected from $R^L$, and wherein $R^1$ is substituted with a substituent selected from $R^7$;
$R^2$ is hydrogen;
$R^3$ is selected from the group consisting of:
(1) hydrogen,
(2) halogen,
(3) —$OR^e$,
(4) —CN,
(5) —$C_{1-6}$alkyl,
(6) —$C_{3-6}$cycloalkyl, and
(7) —$C_{3-6}$cycloalkyl-$C_{1-3}$alkyl-,
wherein each alkyl and cycloalkyl is unsubstituted or substituted with one to three substituents selected from $R^i$;
$R^4$ is selected from the group consisting of:
(1) hydrogen,
(2) halogen,
(3) $OR^e$,
(4) $C_{1-6}$alkyl,
(5) $C_{1-6}$alkyl-O—,
(6) $C_{3-6}$cycloalkyl,
(7) $C_{3-6}$cycloalkyl-O—,
(8) $C_{3-6}$cycloalkyl-$C_{1-10}$alkyl-,
(9) $C_{3-6}$cycloalkyl-$C_{1-10}$alkyl-O—,
(10) $C_{2-5}$cycloheteroalkyl,
(11) $C_{2-5}$cycloheteroalkyl-O—,
(12) $C_{2-5}$cycloheteroalkyl-$C_{1-10}$alkyl-,
(13) $C_{2-5}$cycloheteroalkyl-$C_{1-10}$alkyl-O—,
(14) aryl,
(15) aryl-O—,
(16) aryl-$C_{1-10}$alkyl-,
(17) heteroaryl,
(18) heteroaryl-O—, and
(19) heteroaryl-$C_{1-10}$alkyl-,
wherein each alkyl, cycloalkyl, cycloheteroalkyl, aryl and heteroaryl is unsubstituted or substituted with one to three substituents selected from $R^j$,
provided that when $R^4$ is selected from the group consisting of:
(1) $OR^e$,
(2) $C_{1-6}$alkyl-O—,
(3) $C_{3-6}$cycloalkyl-O—,
(4) $C_{3-6}$cycloalkyl-$C_{1-10}$alkyl-O—,
(5) $C_{2-5}$cycloheteroalkyl-O—,
(6) $C_{2-5}$cycloheteroalkyl-$C_{1-10}$alkyl-O—,
(7) aryl-O—, and
(8) heteroaryl-O—,
then Y is selected from the group consisting of: —$CR^gR^g$;

R⁵ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
R⁶ is selected from the group consisting of:
(1) hydrogen,
(2) —$C_{1-6}$alkyl, and
(3) —$C_{3-6}$cycloalkyl,
wherein each alkyl and cycloalkyl is unsubstituted or substituted with one to three substituents selected from $R^j$;
R⁷ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$alkyl-$SO_2NHCOR^m$,
(5) —$C_{1-6}$alkyl-tetrazolyl, and
(6) a cycloheteroalkyl selected from the group consisting of:

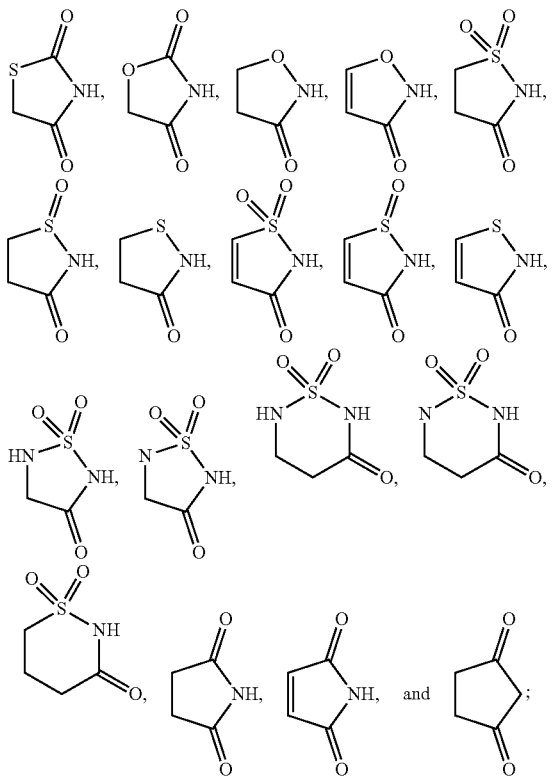

R⁸ is selected from the group consisting of:
(1) hydrogen,
(2) —$C_{1-6}$alkyl,
(3) —$C_{3-6}$cycloalkyl, and
(4) aryl-$C_{1-6}$-alkyl,
wherein each alkyl, cycloalkyl and aryl is unsubstituted or substituted with one to three substituents selected from $R^j$;
$R^a$ is selected from the group consisting of:
(1) —$C_{1-6}$alkyl,
(2) halogen,
(3) —$OR^e$,
(4) —$NR^cS(O)_nR^e$,
(5) —$S(O)_nR^e$,
(6) —$S(O)_nNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) aryl,
(20) heteroaryl,
(21) —$C_{3-6}$cycloalkyl,
(22) —$C_{3-6}$cycloalkenyl, and
(23) —$C_{2-5}$cycloheteroalkyl,
wherein each alkyl, cycloalkyl, cycloalkenyl, cycloheteroalkyl, aryl and heteroaryl is unsubstituted or substituted with —$C_{1-6}$alkyl, halogen, —O—$C_{1-6}$alkyl and —$CF_3$;
$R^b$ is independently selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)_pOC_{1-10}$alkyl,
(10) —$O(CH_2)_pC_{3-6}$cycloalkyl,
(11) —$O(CH_2)_pC_{3-6}$ cycloalkyl-$C_{1-10}$alkyl-,
(12) —$O(CH_2)_pC_{2-5}$cycloheteroalkyl,
(13) —$O(CH_2)_pC_{2-5}$cycloheteroalkyl-$C_{1-10}$alkyl-,
(14) —O-aryl,
(15) —O-heteroaryl,
(16) —O-aryl-$C_{1-10}$alkyl-,
(17) —O-heteroaryl-$C_{1-10}$alkyl-,
(18) —$O(CH_2)_pNR^cS(O)_mR^e$,
(19) —$O(CH_2)_pS(O)_mR^e$,
(20) —$O(CH_2)_pS(O)_mNR^cR^d$,
(21) —$O(CH_2)_pNR^cR^d$,
(22) —$C(O)R^e$,
(23) —$OC(O)R^e$,
(24) —$CO_2R^e$,
(25) —$C(O)NR^cR^d$,
(26) —$NR^cC(O)R^e$,
(27) —$NR^cC(O)OR^e$,
(28) —$NR^cC(O)NR^cR^d$,
(29) —$O(CH_2)_pO$—$C_{3-6}$cycloalkyl,
(30) —$O(CH_2)_pO$—$C_{2-5}$cycloheteroalkyl,
(31) —$OCF_3$,
(32) —$OCHF_2$,
(33) —$(CH_2)_pC_{3-6}$cycloalkyl,
(34) —$(CH_2)_pC_{2-5}$cycloheteroalkyl,
(35) aryl,
(36) heteroaryl,
(37) aryl-$C_{1-10}$alkyl-, and
(38) heteroaryl-$C_{1-10}$alkyl-,
wherein each CH, $CH_2$, alkyl, alkenyl, cycloalkyl, cycloheteroalkyl, aryl and heteroaryl is unsubstituted or substituted with —$C_{1-6}$alkyl, halogen, —O—$C_{1-6}$alkyl and —$CF_3$;
$R^c$ and $R^d$ are each independently selected from the group consisting of:
(1) hydrogen,
(2) $C_{1-10}$alkyl, (3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl,
(7) $C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents independently selected from $R^f$;
each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) aryl-$C_{1-10}$alkyl-,
(10) heteroaryl, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents selected from $R^h$;
each $R^f$ is selected from the group consisting of:
(1) halogen,
(2) $C_{1-10}$alkyl,
(3) —OH,
(4) —O—$C_{1-4}$alkyl,
(5) —S(O)$_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;
each $R^g$ is selected from the group consisting of:
(1) hydrogen,
(2) —C(O)$R^e$, and
(3) —$C_{1-10}$alkyl,
wherein each alkyl is unsubstituted or substituted with one to five halogens;
each $R^h$ is selected from the group consisting of:
(1) halogen,
(2) $C_{1-10}$alkyl,
(3) —OH,
(4) —O—$C_{1-4}$alkyl,
(5) —S(O)$_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;
$R^i$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —C(O)$R^e$,
(9) —OC(O)$R^e$,
(10) —$CO_2R^e$,
(11) —CN,
(12) —C(O)$NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;
$R^j$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —C(O)$R^e$,
(9) —OC(O)$R^e$,
(10) —$CO_2R^e$,
(11) —CN,
(12) —C(O)$NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$ cycloheteroalkyl;
each $R^k$ is independently selected from the group consisting of:
(1) hydrogen,
(2) —$C_{1-6}$ alkyl,
(3) —$C_{1-6}$alkyl-$SO_2C_{1-6}$alkyl,
(4) —$CF_3$, and
(5) —$CHF_2$,
wherein each alkyl is unsubstituted or substituted with one to three substituents independently selected from: —OH, —$OC_{1-6}$alkyl, halogen, cyano, and —$S(O)_2C_{1-6}$alkyl;
each $R^L$ is independently selected from the group consisting of:
(1) —$CO_2C_{1-6}$alkyl,
(2) —$C_{1-10}$alkyl,
(3) —$C_{2-10}$ alkenyl,
(4) —$C_{2-10}$alkynyl,
(5) —$C_{3-6}$cycloalkyl,
(6) —$C_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;
each $R^m$ is independently selected from the group consisting of:
(1) —$C_{1-10}$alkyl,
(2) —$C_{2-10}$ alkenyl,
(3) —$C_{3-6}$ cycloalkyl,
(4) —$C_{3-6}$ cycloalkyl-$C_{1-10}$alkyl-,
(5) —$C_{2-5}$cycloheteroalkyl, (6) —C$_{2-5}$cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;
R" is selected from the group consisting of:
(1) hydrogen, and
(2) —C$_{1-10}$alkyl,
wherein each alkyl is unsubstituted or substituted with one to five halogens;
each n is independently selected from: 0, 1 or 2;
each m is independently selected from: 0, 1 or 2; and
each p is independently selected from: 0, 1, 2, 3, 4, 5 or 6.

2. The compound according to claim 1 wherein "a" is a single bond, and R$^6$ is present; or a pharmaceutically acceptable salt thereof.

3. The compound according to claim 1 wherein Y is —CH$_2$; or a pharmaceutically acceptable salt thereof.

4. The compound according to claim 1 wherein A is selected from the group consisting of:
(1) —C$_{1-6}$alkyl-N(R")—, and
(2) —C$_{6-14}$cycloheteroalkyl,
wherein A is unsubstituted or substituted with one to five substituents selected from R$^a$; or a pharmaceutically acceptable salt thereof.

5. The compound according to claim 1 wherein B is selected from the group consisting of:
(1) aryl-C$_{1-10}$ alkyl-, and
(2) heteroaryl,
wherein B is unsubstituted or substituted with one to five substituents selected from R$^b$; or a pharmaceutically acceptable salt thereof.

6. The compound according to claim 1 wherein B is aryl-C$_{1-10}$ alkyl-, wherein B is unsubstituted or substituted with one to five substituents selected from R$^b$; or a pharmaceutically acceptable salt thereof.

7. The compound according to claim 1 wherein R$^3$ is hydrogen; R$^4$ is hydrogen; R$^5$ is hydrogen; and R$^6$ is hydrogen; or a pharmaceutically acceptable salt thereof.

8. The compound according to claim 1 wherein R$^7$ is —CO$_2$R$^8$; or a pharmaceutically acceptable salt thereof.

9. The compound according to claim 1 wherein R$^8$ is hydrogen; or a pharmaceutically acceptable salt thereof.

10. The compound according to claim 1 of structural Formula Ik:

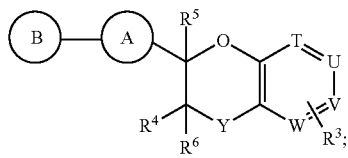

wherein
"a" is a single bond, and R$^6$ is present;
T is CH;
U is CR$^1$;
V is CR$^2$;
W is CH;
Y is selected from the group consisting of: —CR$^g$R$^g$;
A is selected from the group consisting of:
(1) —C$_{1-6}$alkyl-N(R")—,
(2) —C$_{1-6}$alkyl-C$_{6-14}$cycloheteroalkyl, and
(3) —C$_{6-14}$cycloheteroalkyl, wherein A is unsubstituted or substituted with one to five substituents selected from R$^a$;
B is selected from the group consisting of:
(1) aryl-C$_{1-10}$ alkyl-, and
(2) heteroaryl,
wherein B is unsubstituted or substituted with one to five substituents selected from R$^b$;
R$^1$ is selected from —C$_{1-6}$alkyl, wherein each alkyl is unsubstituted or substituted with one to three substituents selected from R$^L$, and wherein R$^1$ is substituted with a substituent selected from R$^7$;
R$^2$ is hydrogen;
R$^3$ is hydrogen;
R$^4$ is hydrogen;
R$^5$ is hydrogen;
R$^6$ is hydrogen;
R$^7$ is —CO$_2$R$^8$;
R$^8$ is hydrogen;
or a pharmaceutically acceptable salt thereof.

11. The compound according to claim 1 of structural formula In:

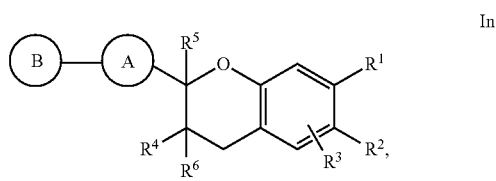

wherein
A is selected from the group consisting of:
(1) —C$_{1-6}$alkyl-N(R")—, and
(2) —C$_{6-14}$cycloheteroalkyl,
wherein A is unsubstituted or substituted with one to five substituents selected from R$^a$;
B is aryl-C$_{1-10}$ alkyl-, wherein B is unsubstituted or substituted with one to five substituents selected from R$^b$;
R$^1$ is —C$_{1-6}$alkyl, wherein each alkyl is unsubstituted or substituted with one to three substituents selected from R$^L$, and wherein R$^1$ is substituted with a substituent selected from R$^7$;
R$^2$ is hydrogen;
R$^3$ is hydrogen;
R$^4$ is hydrogen;
R$^5$ is hydrogen;
R$^6$ is hydrogen;
R$^7$ is —CO$_2$R$^8$;
R$^8$ is hydrogen;
or a pharmaceutically acceptable salt thereof.

12. The compound according to claim 11 selected from:

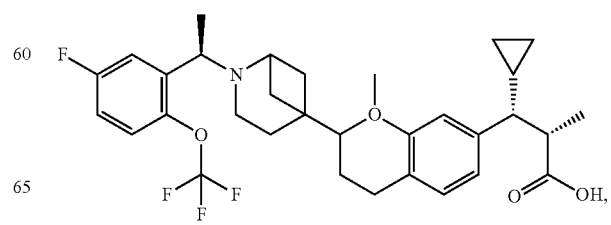

-continued

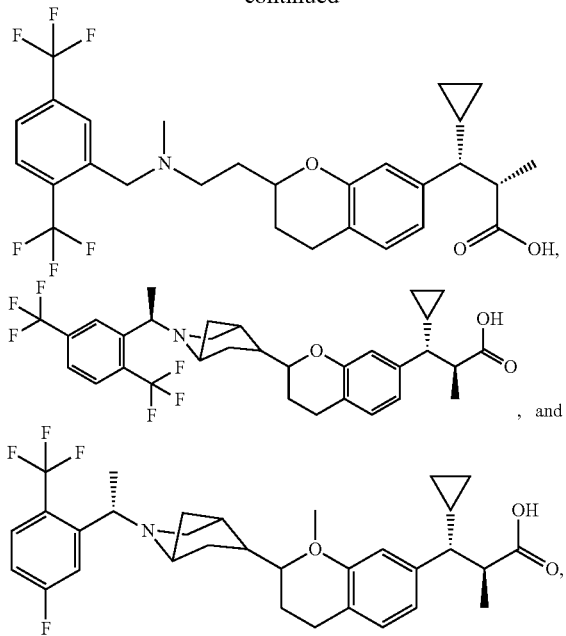

or a pharmaceutically acceptable salt thereof.

13. A pharmaceutical composition comprising a compound of claim 1, or a pharmaceutically acceptable salt thereof, and a pharmaceutically acceptable carrier.

14. A pharmaceutical composition comprising (1) a compound of claim 1, or a pharmaceutically acceptable salt thereof;

(2) one or more compounds selected from the group consisting of:
(a) PPAR gamma agonists and partial agonists;
(b) biguanides;
(c) protein tyrosine phosphatase-1B (PTP-1B) inhibitors;
(d) dipeptidyl peptidase IV (DP-IV) inhibitors;
(e) insulin or an insulin mimetic;
(f) sulfonylureas;
(g) α-glucosidase inhibitors;
(h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (viii) phenolic anti-oxidants;
(i) PPARα/γ dual agonists,
(j) PPARδ agonists,
(k) antiobesity compounds,
(l) ileal bile acid transporter inhibitors;
(m) anti-inflammatory agents;
(n) glucagon receptor antagonists;
(o) GLP-1;
(p) GIP-1;
(q) GLP-1 analogs;
(r) HSD-1 inhibitors;
(s) SGLT-2 inhibitors; and
(t) SGLT-1/SGLT-2 inhibitors; and
(3) a pharmaceutically acceptable carrier.

15. A pharmaceutical composition comprising a compound according to claim 1, or a pharmaceutically acceptable salt thereof, and a compound selected from simvastatin, ezetimibe and sitagliptin; and a pharmaceutically acceptable carrier.

* * * * *